US008728484B2

(12) United States Patent
Mundt et al.

(10) Patent No.: US 8,728,484 B2
(45) Date of Patent: May 20, 2014

(54) VACCINE FOR RUNTING-STUNTING SYNDROME

(75) Inventors: Egbert Mundt, Dessan (DE); Holly S. Sellers, Bishop, GA (US); Guillermo Zavala, Flowery Branch, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 313 days.

(21) Appl. No.: 13/107,140

(22) Filed: May 13, 2011

(65) Prior Publication Data

US 2011/0236407 A1 Sep. 29, 2011

Related U.S. Application Data

(63) Continuation-in-part of application No. PCT/US2009/065259, filed on Nov. 20, 2009.

(60) Provisional application No. 61/116,396, filed on Nov. 20, 2008.

(51) Int. Cl.
*A61K 39/12* (2006.01)
*C07K 14/08* (2006.01)
*C07H 21/04* (2006.01)
*C07K 16/10* (2006.01)
*G01N 33/53* (2006.01)
*C12Q 1/68* (2006.01)
*A61P 31/14* (2006.01)

(52) U.S. Cl.
USPC ............... 424/186.1; 530/350; 530/387.9; 536/23.72; 536/24.33; 435/320.1; 435/7.92; 435/6.12

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. | |
| 6,951,650 B1 | 10/2005 | van Loon | |
| 2006/0147464 A1* | 7/2006 | Baxendale et al. | 424/199.1 |
| 2011/0236407 A1* | 9/2011 | Mundt et al. | 424/186.1 |

FOREIGN PATENT DOCUMENTS

| | | | |
|---|---|---|---|
| WO | WO 2004/030614 A2 | | 4/2004 |
| WO | WO 2004/030614 A3 | | 8/2004 |
| WO | WO 2007/077464 | * | 7/2007 |
| WO | WO 2008/076518 A2 | | 6/2008 |
| WO | WO 2008/076518 A3 | | 9/2008 |
| WO | WO 2009/158614 A1 | | 12/2009 |
| WO | WO 2009/158618 A2 | | 12/2009 |
| WO | WO 2009/158618 A3 | | 4/2010 |
| WO | WO 2010/059899 A2 | | 5/2010 |
| WO | WO 2010/059899 A3 | | 10/2010 |

OTHER PUBLICATIONS

Sequence alignment of SEQ ID NO: 5 of Todd et al. (geneseq accession no: AGE23057, Oct. 18, 2007).*
Sequence alignment of SEQ ID NO: 4 of Todd et al. (geneseq accession no: AGE23056, Oct. 18, 2007).*
Clark and Jones, "Runting-Stunting Syndrome in Broilers," Aug. 27, 2008, *Avian Advice Spring* 2008, available online: <thepoultrysite.com/articles/1110/runtingstunting-syndrome-in-broilers>;.
Decaesstecker et al., "Significance of parvoviruses, entero-like viruses and reoviruses in the aetiology of the chicken malabsorption syndrome," 1986 *Avian Pathol.* 15:769-782.
Frazier and Reece, "Infectious stunting syndrome of chickens in Great Britain: Intestinal ultrastructural pathology," Oct. 1990 *Avian Path.* 19: 759-777.
Genbank Accession No. AAC13556: National Center for Biotechnology Information, National Library of Medicine, National Institutes of Health, GenBank Locus AAC13556, Version AAC13556.1 GI:3046974, "capsid precursor protein [Mamastrovirus 2]," [online] Bethesda, MD [retrieved on Jun. 6, 2013]. Retrieved from the Internet:<http://www.ncbi.nlm.nih.gov/protein/AAC13556>; 1 pg.
Genbank Accession No. AAV37186: National Center for Biotechnology Information, National Library of Medicine, National Institutes of Health, GenBank Locus AAV37186, Version AAV37186.1 GI:54660015, "capsid protein [Turkey astrovirus 2]," [online] Bethesda, MD [retrieved on Jun. 3, 2013]. Retrieved from the Internet: <http://www.ncbi.nlm.nih.gov/protein/AAV37186>; 1 pg.
Genbank Accession No. AAV37187: National Center for Biotechnology Information, National Library of Medicine, National Institutes of Health, GenBank Locus AAV37187, AAV37187.1 GI:54660017, "capsid protein [Turkey astrovirus 3]," [online] Bethesda, MD [retrieved on Jun. 3, 2013]. Retrieved from the Internet:<http://vvvvw.ncbi.nlm.nih.gov/protein/AAV37187>; 2 pgs.
Genbank Accession No. ABX46565: National Center for Biotechnology Information, National Library of Medicine, National Institutes of Health, GenBank Locus ABX46565, Version ABX46565.1 GI:160693733, "RDRP, partial [Avastrovirus 3]," [online]. Bethesda, MD [retrieved on Jun. 3, 2013]. Retrieved from the Internet: <http://www.ncbi.nlm.nih.gov/protein/ABX46565>; 1 pg.
Genbank Accession No. ABX46578: National Center for Biotechnology Information, National Library of Medicine, National Institutes of Health, GenBank Locus ABX46578, Version ABX46578.1 GI:160693750, "capsid precursor [Turkey astrovirus]," [online]. Bethesda, MD [retrieved on Jun. 3, 2013]. Retrieved from the Internet: <http://wwvv.ncbi.nlm.nih.gov/protein/ABX46578>; 1 pg.

(Continued)

*Primary Examiner* — Shanon A Foley
(74) *Attorney, Agent, or Firm* — Mueting, Raasch & Gebhardt, P.A.

(57) ABSTRACT

The present invention includes polypeptides, polynucleotides, antibodies, and vaccines associated with Runting Stunting Syndrome (RSS) in poultry. The present invention also includes diagnostic methods based on such polypeptides, polynucleotides, and antibodies and methods of protecting poultry, including chickens, against RSS by the administration of such polypeptides, polynucleotides, antibodies, and vaccines.

20 Claims, 26 Drawing Sheets

(56) References Cited

OTHER PUBLICATIONS

Genbank Accession No. ACN88712: National Center for Biotechnology Information, National Library of Medicine, National Institutes of Health, GenBank Locus ACN88712, Version ACN88712.1 GI:225380916, "capsid protein precursor [Bat astrovirus Tm/Guangxi/LD71/2007]," [online] Bethesda, MD [retrieved on Jun. 3, 2013]. Retrieved from the Internet: <http://www.ncbi.nlm.nih.gov/protein/ACN88712>; 1 pg.

Genbank Accession No. AY304469: National Center for Biotechnology Information, National Library of Medicine, National Institutes of Health, GenBank Locus AY304469, Version AY304469.1 GI:38565109, "Human astrovirus type 8 T8/US/KL1553/1998 capsid protein precursor, gene, partial cds," [online] Bethesda, MD [retrieved on Jun. 3, 2013]. Retrieved from the Internet: <http://www.ncbi.nlm.nih.gov/nuccore/AY304469>; 1 pg.

Genbank Accession No. BAA33721: National Center for Biotechnology Information, National Library of Medicine, National Institutes of Health, GenBank Locus BAA33721, Version BAA33721.2 GI:5731571, "capsid protein precursor [Mamastrovirus 1]," [online] Bethesda, MD [retrieved on Jun. 3, 2013]. Retrieved from the Internet:.<http://wwvv.ncbi.nlm.nih.gov/protein/BAA33721>; 1 pg.

Genbank Accession No. BAA92849: National Center for Biotechnology Information, National Library of Medicine, National Institutes of Health, GenBank Locus BAA92849, Version BAA92849.1 GI:7288157, "structural polyprotein [Avian nephritis virus 1]," [online] Bethesda, MD [retrieved on Jun. 3 2013]. Retrieved from the Internet: <http://www.ncbi.nlm.nih.gov/protein/BAA92849>; 1 pg.

Genbank Accession No. BAB21617: National Center for Biotechnology Information, National Library of Medicine, National Institutes of Health, GenBank Locus BAB21617, Version BAB21617.1 GI:12697778, "virus capsid polyprotein [Avian nephritis virus 2]," [online]. Bethesda, MD [retrieved on Jun. 3, 2013]. Retrieved from the Internet: <http://vvww.ncbi.nlm.nih.gov/protein/BAB21617>; 1 pg.

Genbank Accession No. CAB95000: National Center for Biotechnology Information, National Library of Medicine, National Institutes of Health, GenBank Locus CAB95000, Version CAB95000.1 Gi:8671341, "capsid protein precursor [Mamastrovirus 3]," [online]. Bethesda, MD [retrieved on Jun. 6, 2013]. Retrieved from the Internet: <http://www.ncbi.nlm.nih.gov/protein/CAB95000>; 2 pgs.

Genbank Accession No. NP_059946: National Center for Biotechnology Information, National Library of Medicine, National Institutes of Health, GenBank Locus NP_059946, Version NP_059946.1 GI:9635575, "capsid protein precursor [Mamastrovirus 13]," [online] Bethesda, MD [retrieved on Jun. 3, 2013]. Retrieved from the Internet: <http://www.ncbi.nlm.nih.gov/protein/NP_059946>; 2 pgs.

Genbank Accession No. NP_795336: National Center for Biotechnology Information, National Library of Medicine, National Institutes of Health, GenBank Locus NP_795336, Version NP_795336.1 GI:28867242, "capsid protein precursor [Mamastrovirus 10]," [online] Bethesda, MD [retrieved on Jun. 3, 2013]. Retrieved from the Internet <http://www.ncbi.nlm.nih.gov/protein/NP_795336>; 1 pg.

Genbank Accession No. YP_002728003: National Center for Biotechnology Information, National Library of Medicine, National Institutes of Health, GenBank Locus YP_002728003, Version YP_002728003.1 GI:225676455, "capsid protein [Duck astrovirus C-NGB]," [online]. Bethesda, MD [retrieved on Jun. 3, 2013]. Retrieved from the Internet: <http://www.ncbi.nlm.nih.gov/protein/YP_002728003>; 2 pgs.

Guy, "Virus Infection of the Gastrointestinal Tract of Poultry," Aug. 1998 *Poultry Sci.* 77: 1166-1175.

Himley et al, "The DF-1 chicken fibroblast cell line: transformation induced by diverse oncogenes and cell death resulting from infection by avian leukosis viruses," Sep. 1, 1998 *Virology* 248:295-304.

Imada et al., "Avian nephritis virus (ANV) as a new member of the family Astroviridae and construction of infectious ANV cDNA," Sep. 2000 *J Virol.* 74: 8487-8493.

Kouwenhoven et al., "Investigations into the role of reovirus in the malabsorption syndrome," 1988 *Avian Pathol.* 17:879-892.

Letzel et al. "Evidence for functional significance of the permuted C motif in $Co^{2+}$-stimulated RNA-dependent RNA polymerase of infectious bursal disease virus," Oct. 2007 *J Gen. Virol.* 88:2824-2833.

Lin et al., "Baculovirus surface display of σC or σB proteins of avian reovirus and immunogenicity of the displayed proteins in a mouse model," 2008 *Vaccine* 26:6361-6367. Available online on Sep. 20, 2008.

Mahmood et al., "H5N1 VLP vaccine induced protection in ferrets against lethal challenge with highly pathogenic H5N1 influenza viruses," Oct. 3, 2008 *Vaccine* 26:5393-9. Available online on Aug. 14, 2008.

McNulty et al., "An entero-like virus associated with the runting syndrome in broiler chickens," Jul. 1984 *Avian Path.* 13:429-439.

Reece and Frazier, "Infectious stunting syndrome of chickens in Great Britain: Field and Experimental Studies," Oct. 1990 *Avian Path.* 19:723-758.

Sellers et al., "A purified recombinant baculovirus expressed capsid protein of a new astrovirus provides partial protection to runting-stunting syndrome in chickens," Feb. 3, 2010 *Vaccine* 28(5):1253-63. Available online on Nov. 24, 2009.

Smart et al., "Experimental reproduction of the runting stunting syndrome of broiler chickens," 1988 *Avian Pathol.* 17:617-27.

Smith and Petrenko, "Phage Display," Apr. 1, 1997 *Chem. Rev.* 97:391-410.

Songserm et al., "Enteropathogenicity of Dutch and German avian reoviruses in SPF white leghorn chickens and broilers," May — Jun. 2003 *Vet. Res.* 34:285-295.

Spackman et al., "The Pathogenesis of turkey origin reoviruses in turkeys and chickens," Aug. 2005 *Avian Pathol.* 34:291-296.

vanLoon et al., "Isolation of a new serotype of avian reovirus associated with malabsorption syndrome in chickens," Jul. 2001 *Vet. Quart.* 23:129-133.

Zavala, 2006, "Runting stunting syndrome (RSS) in broilers: *in vivo* studies," slides accompanying oral presentation available online: <poultry-health.com/fora/inthelth/zavala_wpdc_06.pdf>; 59 pages.

Zavala and Barbosa, May 2006, "Runting and stunting in broiler chickens," May 2006 *Apinco-Facta*, available online: <poultry-health.com/fora/inthelth/zavala_apinco_06.pdf>; 4 pages.

Zhang et al., "Immunization of mice with dengue structural proteins and nonstructural protein NS1 expressed by baculovirus recombinant induces resistance to dengue virus encephalitis," Aug. 1988 *J. Virol.* 62:3027-31.

Zsak et al., "Partial genome sequence analysis of parvoviruses associated with enteric disease in poultry," Aug. 2008 *Avian Path.* 37: 435-41. Available online on Jul. 14, 2008.

International Preliminary Report on Patentability issued May 24, 2011, in connection with International Patent Application No. PCT/US2009/065259, filed Nov. 20, 2009.

International Search Report mailed Aug. 24, 2010, in connection with International Patent Application No. PCT/US2009/065259, filed Nov. 20, 2009.

Written Opinion mailed Aug. 24, 2010, in connection with International Patent Application No. PCT/US2009/065259, filed Nov. 20, 2009.

\* cited by examiner

*Figure 1*
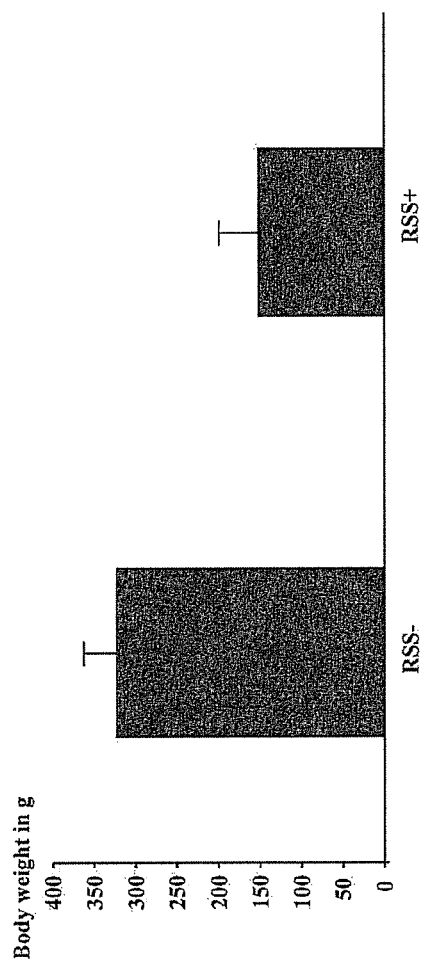
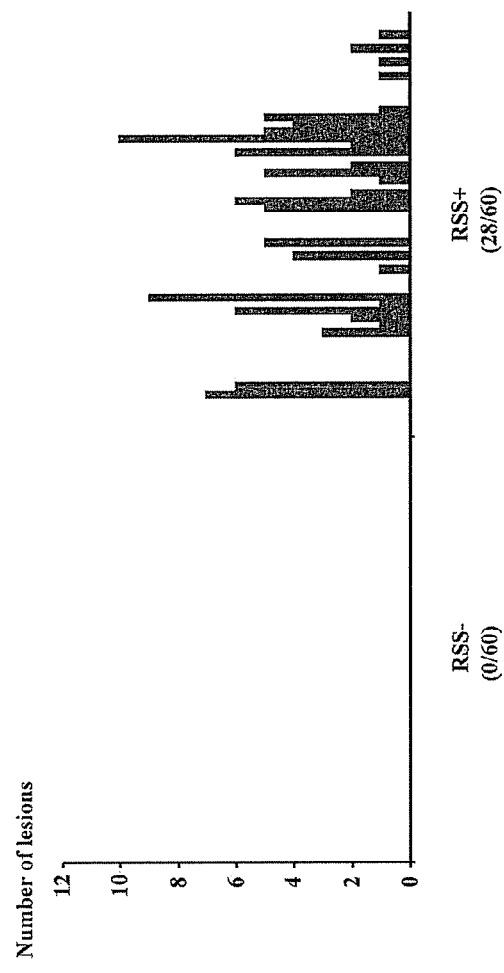

A
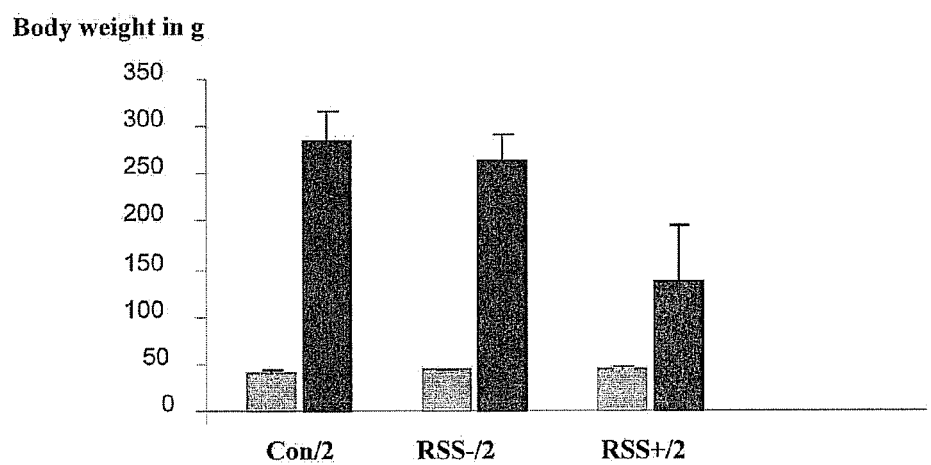
B
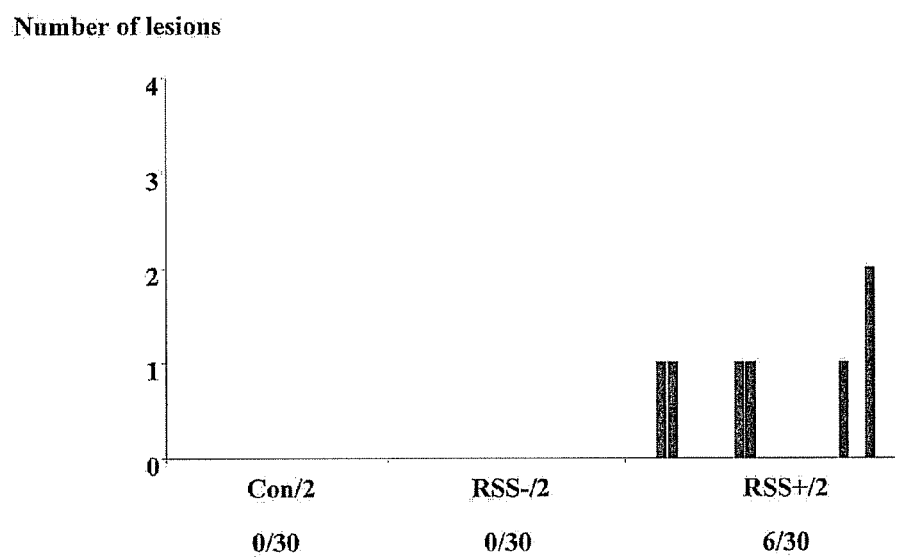
Figure 2

```
  1  Met Ala Asp Lys Ala Gly Pro Gln Lys Arg Arg Val Ser Arg Arg Gly   16
  1  ATG GCC GAT AAG GCT GGG CCG CAG AAG AGG AGG GTA TCT AGG CGC GGT   48

17  Arg Gly Arg Ser Arg Ser Arg Ser Arg Ser Arg Ser Arg Ser Arg Asn   32
 49  CGT GGC CGC TCT CGG TCA AGG TCG CGC TCA CGT TCT CGA TCA AGA AAT   96

33  Arg Val Lys Lys Thr Val Thr Ile Val Glu Thr Lys Lys Thr Pro Ser   48
 97  CGT GTA AAG AAA ACA GTC ACG ATC GTT GAA ACA AAA AAG ACC CCA AGT  144

49  Lys Ser Ile Leu Lys Lys Glu Leu Asp Asn His Glu Arg Lys Asp Arg   64
145  AAG TCA ATC CTG AAA AAG GAG TTG GAC AAT CAT GAG AGG AAA GAT AGA  192

65  Lys Arg Phe Arg Lys Leu Glu Lys Lys Leu Asn Gly Pro Lys Ile His   80
193  AAA AGG TTC AGA AAA TTG GAA AAG AAA TTA AAT GGA CCA AAA ATT CAC  240

81  Asp Arg Met Ala Val Thr Thr Thr Leu Gly Val Leu Thr Gly Asn Ser   96
241  GAT CGC ATG GCG GTT ACA ACC ACT CTT GGT GTT CTC ACC GGC AAT TCT  288

97  Asp Asn Asn Leu Glu Arg Lys Met Arg Ala Leu Leu Asn Pro Leu Leu  112
289  GAC AAT AAT TTG GAA AGG AAG ATG AGG GCA TTG CTT AAT CCC TTA CTC  336

113  Leu Lys Ser Gln Asn Thr Gly Ala Ser Ala Ser Pro Leu Ser Leu Arg  128
337  TTG AAA TCC CAG AAC ACT GGA GCA TCG GCA TCA CCA CTC TCC CTT AGA  384

129  Ala Ser Gln Tyr Ser Met Trp Lys Ile Gln Arg Cys Val Val Lys Phe  144
385  GCC TCA CAG TAT TCA ATG TGG AAA ATA CAG CGG TGT GTT GTT AAA TTT  432

145  Val Pro Leu Val Gly Ala Ala Asn Val Ala Gly Ser Val Ser Phe Val  160
433  GTA CCG CTG GTG GGA GCA GCA AAT GTT GCT GGA AGT GTG TCA TTC GTG  480

161  Ser Leu Asp Gln Asp Ala Thr Ser Ser Gln Pro Glu Ser Pro Asp Thr  176
481  TCG CTG GAC CAA GAT GCA ACA TCC TCT CAA CCT GAA TCA CCT GAT ACC  528

177  Ile Lys Ala Lys Val His Ala Glu Val Ser Ile Gly Gln Arg Phe Asn  192
529  ATA AAG GCG AAG GTG CAT GCC GAG GTG TCC ATT GGC CAG AGG TTC AAC  576

193  Trp Asn Val Gln Ser Arg Tyr Leu Val Gly Pro Arg Ser Gly Trp Trp  208
577  TGG AAT GTG CAA TCT AGA TAC CTT GTT GGA CCG CGG TCT GGC TGG TGG  624

209  Gly Met Asp Thr Gly Glu Ser Pro Thr Asp Thr Val Gly Pro Ala Leu  224
625  GGT ATG GAC ACC GGA GAG TCA CCA ACT GAC ACA GTT GGT CCA GCA CTT  672

225  Asp Phe Trp Asn Leu Tyr Arg Thr Val Asn Thr Leu Gln Thr Gly Thr  240
673  GAC TTC TGG AAT TTA TAT AGG ACA GTA AAT ACT CTC CAA ACT GGC ACA  720

241  Thr Ser Gln Val Tyr Thr Ala Pro Leu Phe Ser Ile Glu Val Phe Thr  256
721  ACA TCT CAG GTT TAC ACC GCT CCA CTA TTT TCT ATA GAA GTA TTC ACC  768

257  Val Tyr Val Phe Ser Gly Tyr Glu Pro Lys Pro Ala Leu Ala Thr Met  272
769  GTC TAT GTA TTT TCA GGG TAC GAA CCC AAG CCT GCC CTT GCC ACA ATG  816

273  Thr Asn Ser Thr Phe Glu Ser Gln Gln Gly Val Thr Ile Thr Asn Gly  288
817  ACA AAT TCA ACT TTT GAA AGT CAG CAG GGG GTG ACT ATA ACA AAT GGC  864
```

*Figure 12-1*

```
 289  Thr Asn Gly Glu Leu Leu Leu Asn Val Pro Gln Arg Ser Ala Leu Ser   304
 865  ACA AAT GGT GAA CTA CTT CTT AAT GTC CCA CAA CGT TCA GCC CTT TCA   912

305  Glu Arg Leu Arg Glu Lys Glu Val Pro His Arg Val Gln Asn Gln Thr   320
 913  GAA AGG CTT CGC GAA AAA GAG GTT CCA CAC CGT GTA CAA AAT CAA ACG   960

321  Gly Gly Val Gly Glu Val Leu Trp Ala Val Ala Ser Gly Ala Val Glu   336
 961  GGT GGT GTT GGA GAA GTA TTA TGG GCA GTT GCA TCA GGA GCG GTG GAG  1008

337  Gly Ala Ala Glu Ala Leu Gly Pro Trp Gly Trp Leu Leu Arg Gly Gly   352
1009  GGG GCT GCA GAA GCT TTA GGA CCC TGG GGG TGG CTA CTA AGA GGT GGT  1056

353  Trp Trp Val Ile Lys Lys Leu Phe Gly Arg Thr Gly Glu Asp Ala Asn   368
1057  TGG TGG GTC ATT AAA AAA CTT TTT GGC AGA ACC GGA GAA GAT GCA AAT  1104

369  Asp Val Tyr Val Met Tyr Ser Ser Ile Glu Asp Ala Asn Lys Asp Ser   384
1105  GAT GTG TAC GTA ATG TAC TCT TCA ATT GAA GAT GCA AAC AAG GAC AGT  1152

385  Arg Ile Tyr Gln Thr Val Thr Gly Ser Val Gln Ile Gln Gln Gly Pro   400
1153  AGA ATA TAT CAA ACT GTC ACT GGA TCG GTG CAA ATA CAA CAA GGC CCA  1200

401  Leu Val Leu Thr Gln Ile Ser Ser Pro Asn Val Asn Thr Ser Gly Gly   416
1201  CTC GTT CTA ACA CAA ATC TCA TCG CCG AAT GTG AAT ACA TCC GGA GGG  1248

417  Val Val Gln Val Asn Ser Thr Thr Pro Asn Asp Tyr Leu Pro Leu Ser   432
1249  GTT GTT CAG GTA AAT TCA ACT ACT CCA AAT GAC TAC TTG CCC CTC TCT  1296

433  Gln Glu Ser Tyr Ala Glu Thr Pro Leu Lys Lys Tyr Val Leu Tyr Asp   448
1297  CAA GAA AGT TAT GCA GAG ACA CCA TTG AAA AAA TAT GTA CTT TAT GAC  1344

449  Ser Thr Gly Asn Pro Val Asp Ser Asn Met Ser His Thr Met Arg Ile   464
1345  AGC ACC GGG AAC CCC GTT GAT AGC AAT ATG AGC CAC ACC ATG AGG ATA  1392

465  Thr Gly Tyr Pro Glu Ser Lys Leu Val Thr Ser Ser Ser Val Trp Leu   480
1393  ACA GGG TAT CCT GAG TCA AAA CTA GTG ACA TCA AGC TCA GTC TGG CTC  1440

481  Gly Thr Thr Gly Lys Ser Val Gln Ser Thr Lys Trp Leu Met Ser Asp   496
1441  GGT ACA ACT GGT AAG AGC GTA CAA TCA ACT AAA TGG CTG ATG TCC GAT  1488

497  Tyr Thr Asn Thr Gly Val Ile Phe Gly Phe Pro Tyr Thr Ser Ala Pro   512
1489  TAC ACA AAT ACA GGG GTC ATA TTT GGT TTT CCT TAT ACG AGC GCA CCA  1536

513  Pro Gly Ala Thr Val Gly Asn Ile Gly Val Ile His Thr Ala Lys Ser   528
1537  CCG GGA GCA ACT GTC GGC AAC ATT GGT GTC ATT CAT ACT GCA AAA TCA  1584

529  Leu Ile Lys Thr Ile Arg Tyr Arg Arg Gln Asn His Leu Pro Thr Thr   544
1585  TTA ATT AAG ACA ATC AGA TAC AGA AGA CAA AAC CAT CTT CCA ACA ACA  1632

545  Pro Phe Glu Ser Ser Leu Ile Pro Ser Ala Ser Lys Gly Pro Ser Gln   560
1633  CCT TTT GAA TCT TCC CTG ATA CCG TCA GCG TCA AAA GGA CCC AGT CAA  1680

561  Met Leu Gly Cys Phe Asp Thr Pro Tyr Val Trp Cys Arg Val Cys Asp   576
1681  ATG CTA GGA TGT TTT GAC ACC CCA TAC GTA TGG TGT AGA GTT TGT GAT  1728
```

*Figure 12-2*

```
577   Asn Thr Cys Ser Thr Lys Pro Thr Asp Gly Ala Val Thr Gln Arg Tyr    592
1729  AAT ACA TGC TCC ACC AAG CCT ACT GAT GGT GCA GTT ACA CAG AGG TAC   1776

593   Asn Ala Trp Gly Leu Leu Val Val Ser Leu Ala His Asp Lys Val Tyr    608
1777  AAT GCA TGG GGC CTG CTG GTG GTT AGC CTT GCC CAT GAT AAG GTG TAT   1824

609   Val Leu Ala Gly Tyr Pro Asn Ser Gln Thr Ala Val Pro Val Gln Gln    624
1825  GTA CTA GCA GGC TAT CCA AAT TCA CAA ACA GCA GTA CCA GTG CAA CAA   1872

625   Leu Val Trp Asp Thr Phe Asp Trp Asp Ala Asn Phe Ser Thr Gly Arg    640
1873  TTG GTT TGG GAT ACT TTT GAC TGG GAT GCA AAT TTT TCC ACT GGC AGA   1920

641   Ile Tyr Ser Ala Val Trp Pro Gly Glu Asp Gly Ala Glu Gln Glu Gly    656
1921  ATT TAT AGC GCA GTA TGG CCA GGT GAA GAT GGT GCT GAA CAG GAA GGT   1968

657   Ser Asp Thr Asp Asp Ala Asp Ser Asp Ile Ser Ser Leu Phe Asp Pro    672
1969  TCA GAC ACT GAT GAT GCT GAC TCT GAC ATT TCC AGT CTT TTT GAC CCA   2016

673   Met Asn Glu Val Glu Lys Asp Phe His Phe Gln Cys Ser Leu Lys Thr    688
2017  ATG AAT GAG GTG GAA AAG GAC TTC CAT TTC CAG TGT AGT CTC AAA ACT   2064

689   Ser Asp Tyr Leu Lys Glu Glu Ala Asp Phe Trp Lys Ala Lys Ala Gln    704
2065  TCT GAC TAC TTA AAA GAG GAG GCT GAC TTT TGG AAA GCA AAG GCG CAA   2112

705   Gln Leu Leu Met Glu Lys Ala Met Glu Lys Pro Ser Ala Asn Pro Pro    720
2113  CAG CTA CTC ATG GAG AAG GCA ATG GAA AAA CCA AGT GCT AAT CCT CCT   2160

721   Leu Val Arg Phe Glu Lys Gly Gly Pro Glu Gln Gln Lys Gln Pro Ala    736
2161  CTT GTC CGC TTC GAG AAG GGT GGA CCT GAG CAG CAA AAA CAA CCT GCT   2208

737   Ser Ser Arg Gly His Ala Glu His His His His His His ***            750
2209  AGC AGC CGC GGC CAC GCC GAG CAT CAC CAT CAC CAT CAC TAG            2250
```

*Figure 12-3*

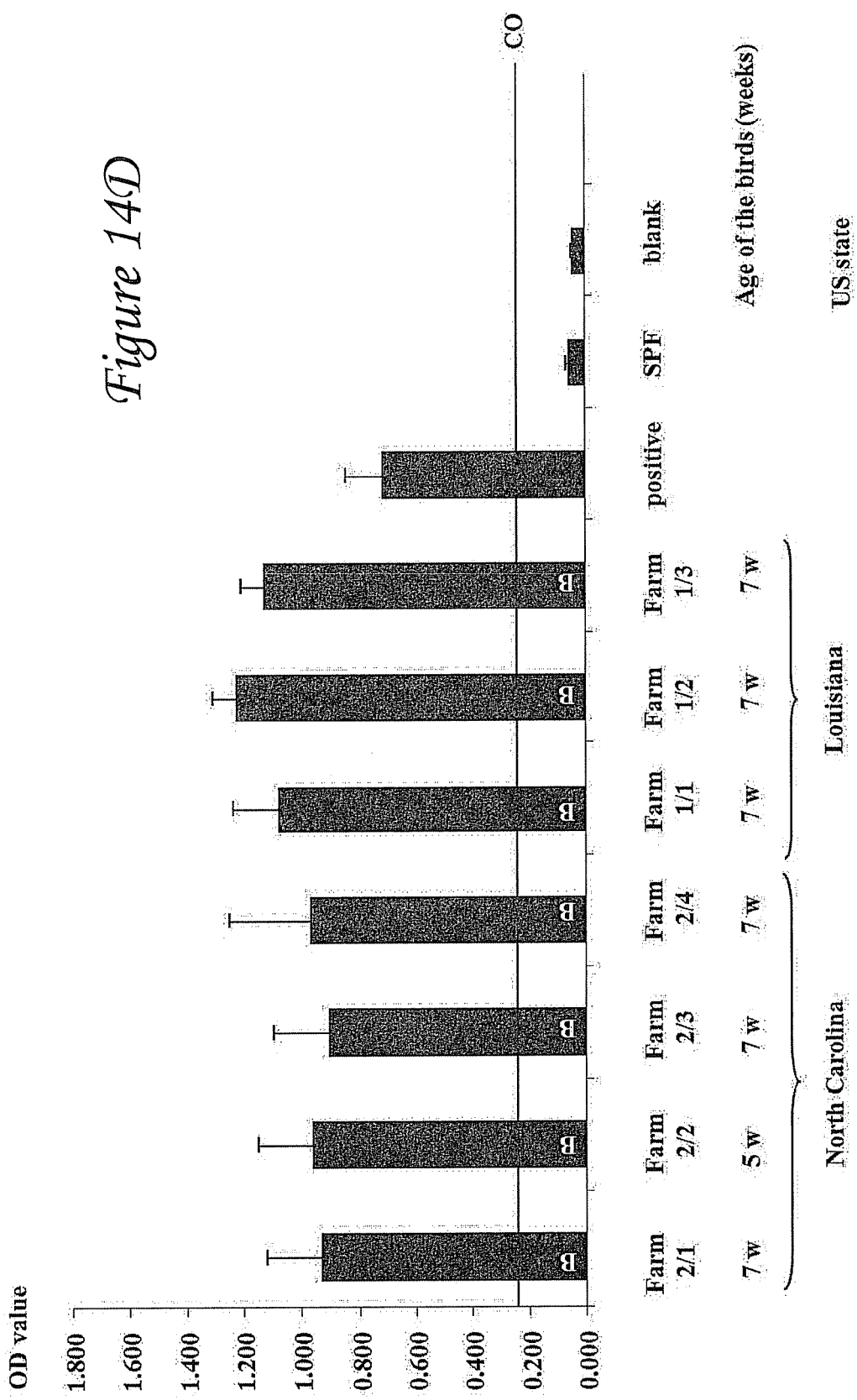

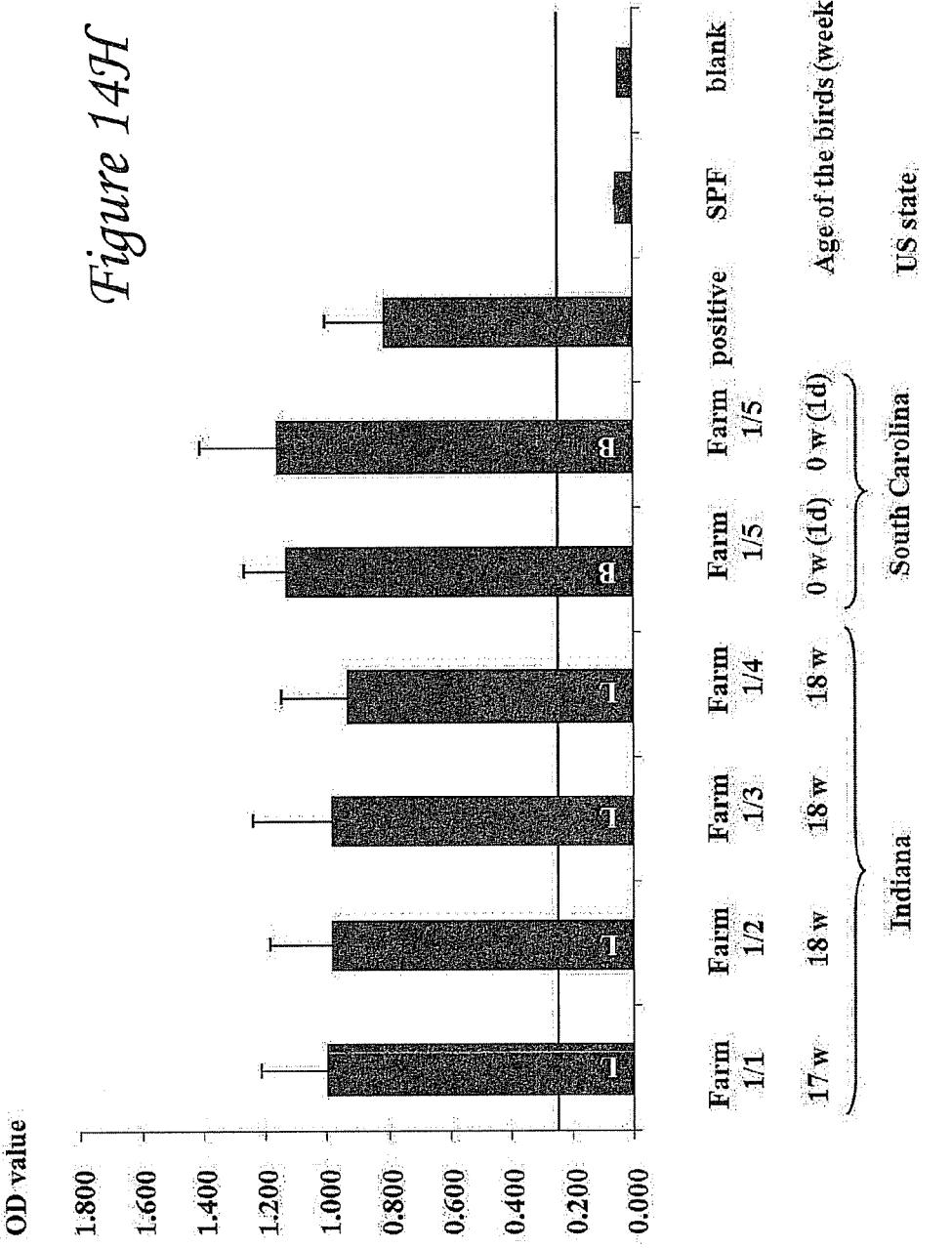

SEQUENCE LISTING

```
<160> NUMBER OF SEQ ID NOS: 19

<210> SEQ ID NO 1
<211> LENGTH: 2250
<212> TYPE: DNA
<213> ORGANISM: astrovirus

<400> SEQUENCE: 1
atggccgata aggctgggcc gcagaagagg agggtatcta ggcgcggtcg tggccgctct      60
cggtcaaggt cgcgctcacg ttctcgatca agaaatcgtg taaagaaaac agtcacgatc     120
gttgaaacaa aaaagacccc aagtaagtca atcctgaaaa aggagttgga caatcatgag     180
aggaaagata gaaaaaggtt cagaaaattg gaaaagaaat taaatggacc aaaaattcac     240
gatcgcatgg cggttacaac cactcttggt gttctcaccg gcaattctga caataatttg     300
gaaaggaaga tgagggcatt gcttaatccc ttactcttga aatcccagaa cactggagca     360
tcggcatcac cactctccct tagagcctca cagtattcaa tgtggaaaat acagcggtgt     420
gttgttaaat ttgtaccgct ggtgggagca gcaaatgttg ctggaagtgt gtcattcgtg     480
tcgctggacc aagatgcaac atcctctcaa cctgaatcac ctgataccat aaaggcgaag     540
gtgcatgccg aggtgtccat tggccagagg ttcaactgga atgtgcaatc tagataccgt     600
gttggaccgc ggtctggctg gtggggtatg gacaccggag agtcaccaac tgacacagtt     660
ggtccagcac ttgacttctg gaatttatat aggacagtaa atactctcca aactggcaca     720
acatctcagg tttacaccgc tccactatt tctatagaag tattcaccgt ctatgtattt      780
tcagggtacg aacccaagcc tgcccttgcc acaatgacaa attcaacttt tgaaagtcag     840
```

```
cagggggtga ctataacaaa tggcacaaat ggtgaactac ttcttaatgt cccacaacgt    900 tcagccctt  cagaaaggct tcgcgaaaaa gaggttccac accgtgtaca aaatcaaacg    960
ggtggtgttg agaagtatt  atgggcagtt gcatcaggag cggtggaggg ggctgcagaa   1020
gctttaggac cctgggggtg gctactaaga ggtggttggt gggtcattaa aaaactttt   1080 ggcagaaccg gagaagatgc aaatgatgtg tacgtaatgt actcttcaat tgaagatgca   1140
aacaaggaca gtagaatata tcaaactgtc actggatcgg tgcaaataca acaaggccca   1200
ctcgttctaa cacaaatctc atcgccgaat gtgaatacat ccggagggt  tgttcaggta   1260 aattcaacca ctccaaatga ctacttgccc ctctctcaag aaagttatgc agagacacca   1320
ttgaaaaaat atgtacttta tgacagcacc gggaaccccg ttgatagcaa tatgagccac   1380
accatgagga taacagggta tcctgagtca aaactagtga catcaagctc agtctggctc   1440
ggtacaactg gtaagagcgt acaatcaact aaatggctga tgtccgatta cacaaataca   1500
ggggtcatat ttggttttcc ttatacgagc gcaccaccgg gagcaactgt cggcaacatt   1560
ggtgtcattc atactgcaaa atcattaatt aagacaatca gatacagaag acaaaaccat   1620
cttccaacaa caccttttga atcttccctg ataccgtcag cgtcaaaagg acccagtcaa   1680
atgctaggat gttttgacac cccatacgta tggtgtagag tttgtgataa tacatgctcc   1740
accaagccta ctgatggtgc agttacacag aggtacaatg catggggcct gctggtggtt   1800
agccttgccc atgataaggt gtatgtacta gcaggctatc caaattcaca acagcagta   1860 ccagtgcaac aattggtttg ggatactttt gactgggatg caaatttttc cactggcaga   1920
atttatagcg cagtatggcc aggtgaagat ggtgctgaac aggaaggttc agacactgat   1980
gatgctgact ctgacatttc cagtcttttt gacccaatga atgaggtgga aaaggacttc   2040
catttccagt gtagtctcaa aacttctgac tacttaaaag aggaggctga cttttggaaa   2100
gcaaaggcgc aacagctact catggagaag gcaatggaaa aaccaagtgc taatcctcct   2160
cttgtccgct tcgagaaggg tggacctgag cagcaaaaac aacctgctag cagccgcggc   2220
cacgccgagc atcaccatca ccatcactag                                    2250
```

<210> SEQ ID NO 2
<211> LENGTH: 749
<212> TYPE: PRT
<213> ORGANISM: astrovirus

<400> SEQUENCE: 2

Met Ala Asp Lys Ala Gly Pro Gln Lys Arg Arg Val Ser Arg Gly
1               5                   10                  15

Met Ala Asp Lys Ala Gly Pro Gln Lys Arg Arg Val Ser Arg Gly
                20                  25                  30

Arg Val Lys Lys Thr Val Thr Ile Val Glu Thr Lys Lys Thr Pro Ser
        35                  40                  45

Lys Ser Ile Leu Lys Lys Glu Leu Asp Asn His Glu Arg Lys Asp Arg
    50                  55                  60

Lys Arg Phe Arg Lys Leu Glu Lys Lys Leu Asn Gly Pro Lys Ile His
65                  70                  75                  80

Asp Arg Met Ala Val Thr Thr Thr Leu Gly Val Leu Thr Gly Asn Ser
                85                  90                  95

Asp Asn Asn Leu Glu Arg Lys Met Arg Ala Leu Leu Asn Pro Leu Leu
            100                 105                 110

Leu Lys Ser Gln Asn Thr Gly Ala Ser Ala Ser Pro Leu Ser Leu Arg
        115                 120                 125

```
Ala Ser Gln Tyr Ser Met Trp Lys Ile Gln Arg Cys Val Val Lys Phe
    130                 135                 140

Val Pro Leu Val Gly Ala Asn Val Ala Gly Ser Val Ser Phe Val
145                 150                 155                 160

Ser Leu Asp Gln Asp Ala Thr Ser Ser Gln Pro Glu Ser Pro Asp Thr
                    165                 170                 175

Ile Lys Ala Lys Val His Ala Glu Val Ser Ile Gly Gln Arg Phe Asn
                180                 185                 190

Trp Asn Val Gln Ser Arg Tyr Leu Val Gly Pro Arg Ser Gly Trp Trp
        195                 200                 205

Gly Met Asp Thr Gly Glu Ser Pro Thr Asp Thr Val Gly Pro Ala Leu
210                 215                 220

Asp Phe Trp Asn Leu Tyr Arg Thr Val Asn Thr Leu Gln Thr Gly Thr
225                 230                 235                 240

Thr Ser Gln Val Tyr Thr Ala Pro Leu Phe Ser Ile Glu Val Phe Thr
                245                 250                 255

Val Tyr Val Phe Ser Gly Tyr Glu Pro Lys Pro Ala Leu Ala Thr Met
                260                 265                 270

Thr Asn Ser Thr Phe Glu Ser Gln Gln Gly Val Thr Ile Thr Asn Gly
            275                 280                 285

Thr Asn Gly Glu Leu Leu Leu Asn Val Pro Gln Arg Ser Ala Leu Ser
290                 295                 300

Glu Arg Leu Arg Glu Lys Glu Val Pro His Arg Val Gln Asn Gln Thr
305                 310                 315                 320

Gly Gly Val Gly Glu Val Leu Trp Ala Val Ala Ser Gly Ala Val Glu
                325                 330                 335

Gly Ala Glu Ala Leu Gly Pro Trp Gly Trp Leu Leu Arg Gly Gly
            340                 345                 350

Trp Trp Val Ile Lys Lys Leu Phe Gly Arg Thr Gly Glu Asp Ala Asn
            355                 360                 365

Asp Val Tyr Val Met Tyr Ser Ser Ile Glu Asp Ala Asn Lys Asp Ser
        370                 375                 380

Arg Ile Tyr Gln Thr Val Thr Gly Ser Val Gln Ile Gln Gln Gly Pro
385                 390                 395                 400

Leu Val Leu Thr Gln Ile Ser Ser Pro Asn Val Asn Thr Ser Gly Gly
                405                 410                 415

Val Val Gln Val Asn Ser Thr Thr Pro Asn Asp Tyr Leu Pro Leu Ser
                420                 425                 430

Gln Glu Ser Tyr Ala Glu Thr Pro Leu Lys Lys Tyr Val Leu Tyr Asp
            435                 440                 445

Ser Thr Gly Asn Pro Val Asp Ser Asn Met Ser His Thr Met Arg Ile
450                 455                 460

Thr Gly Tyr Pro Glu Ser Lys Leu Val Thr Ser Ser Val Trp Leu
465                 470                 475                 480

Gly Thr Thr Gly Lys Ser Val Gln Ser Thr Lys Trp Leu Met Ser Asp
                485                 490                 495

Tyr Thr Asn Thr Gly Val Ile Phe Gly Phe Pro Tyr Ser Ala Pro
                500                 505                 510

Pro Gly Ala Thr Val Gly Asn Ile Gly Val Ile His Thr Ala Lys Ser
            515                 520                 525

Leu Ile Lys Thr Ile Arg Tyr Arg Arg Gln Asn His Leu Pro Thr Thr
            530                 535                 540

Pro Phe Glu Ser Ser Leu Ile Pro Ser Ala Ser Lys Gly Pro Ser Gln
545                 550                 555                 560
```

```
Met Leu Gly Cys Phe Asp Thr Pro Tyr Val Trp Cys Arg Val Cys Asp
                565                 570                 575

Asn Thr Cys Ser Thr Lys Pro Thr Asp Gly Ala Val Thr Gln Arg Tyr
            580                 585                 590

Asn Ala Trp Gly Leu Leu Val Val Ser Leu Ala His Asp Lys Val Tyr
        595                 600                 605

Val Leu Ala Gly Tyr Pro Asn Ser Gln Thr Ala Val Pro Val Gln Gln
    610                 615                 620

Leu Val Trp Asp Thr Phe Asp Trp Asp Ala Asn Phe Ser Thr Gly Arg
625                 630                 635                 640

Ile Tyr Ser Ala Val Trp Pro Gly Glu Asp Ala Glu Gln Glu Gly
                645                 650                 655

Ser Asp Thr Asp Asp Ala Asp Ser Asp Ile Ser Ser Leu Phe Asp Pro
                660                 665                 670

Met Asn Glu Val Glu Lys Asp Phe His Phe Gln Cys Ser Leu Lys Thr
                675                 680                 685

Ser Asp Tyr Leu Lys Glu Glu Ala Asp Phe Trp Lys Ala Lys Ala Gln
            690                 695                 700

Gln Leu Leu Met Glu Lys Ala Met Glu Lys Pro Ser Ala Asn Pro Pro
705                 710                 715                 720

Leu Val Arg Phe Glu Lys Gly Gly Pro Glu Gln Gln Lys Gln Pro Ala
                725                 730                 735

Ser Ser Arg Gly His Ala Glu His His His His His
            740                 745

<210> SEQ ID NO 3
<211> LENGTH: 21
<212> TYPE: DNA
<213> ORGANISM: artificial
<220> FEATURE:
<223> OTHER INFORMATION: synthetic oligonucleotide primer

<400> SEQUENCE: 3 gggtttaca aacctgtgat g                                            21

<210> SEQ ID NO 4
<211> LENGTH: 19
<212> TYPE: DNA
<213> ORGANISM: artificial
<220> FEATURE:
<223> OTHER INFORMATION: synthetic oligonucleotide primer

<400> SEQUENCE: 4
ccgcacacgg cgttcaccc                                              19

<210> SEQ ID NO 5
<211> LENGTH: 20
<212> TYPE: DNA
<213> ORGANISM: artificial
<220> FEATURE:
<223> OTHER INFORMATION: synthetic oligonucleotide primer

<400> SEQUENCE: 5
taaggacttt gtggtctatg                                             20

<210> SEQ ID NO 6
<211> LENGTH: 20
<212> TYPE: DNA
<213> ORGANISM: artificial
<220> FEATURE:
<223> OTHER INFORMATION: synthetic oligonucleotide primer
```

-continued

```
<400> SEQUENCE: 6
catagaccac aaagtcctta                                              20

<210> SEQ ID NO 7
<211> LENGTH: 20
<212> TYPE: DNA
<213> ORGANISM: artificial
<220> FEATURE:
<223> OTHER INFORMATION: synthetic oligonucleotide primer

<400> SEQUENCE: 7
ggcctcgatg cttgggagcc                                              20

<210> SEQ ID NO 8
<211> LENGTH: 20
<212> TYPE: DNA
<213> ORGANISM: artificial
<220> FEATURE:
<223> OTHER INFORMATION: synthetic oligonucleotide primer

<400> SEQUENCE: 8
ggctcccaag catcgaggcc                                              20

<210> SEQ ID NO 9
<211> LENGTH: 24
<212> TYPE: DNA
<213> ORGANISM: artificial
<220> FEATURE:
<223> OTHER INFORMATION: synthetic oligonucleotide primer

<400> SEQUENCE: 9
agattgattg aagcctccag tttg                                         24

<210> SEQ ID NO 10
<211> LENGTH: 29
<212> TYPE: DNA
<213> ORGANISM: artificial
<220> FEATURE:
<223> OTHER INFORMATION: synthetic oligonucleotide primer
<220> FEATURE:
<221> NAME/KEY: misc_feature
<222> LOCATION: (9)..(9)
<223> OTHER INFORMATION: n is a, c, g, or t

<400> SEQUENCE: 10
atgswdgtnc chgarcabcc ygadggcat                                    29

<210> SEQ ID NO 11
<211> LENGTH: 22
<212> TYPE: DNA
<213> ORGANISM: artificial
<220> FEATURE:
<223> OTHER INFORMATION: synthetic oligonucleotide primer

<400> SEQUENCE: 11
ggaaaggaag atgagggcat tg                                           22

<210> SEQ ID NO 12
<211> LENGTH: 22
<212> TYPE: DNA
<213> ORGANISM: artificial
<220> FEATURE:
<223> OTHER INFORMATION: synthetic oligonucleotide primer

<400> SEQUENCE: 12
caatgccctc atcttccttt cc                                           22
```

<210> SEQ ID NO 13
<211> LENGTH: 21
<212> TYPE: DNA
<213> ORGANISM: artificial
<220> FEATURE:
<223> OTHER INFORMATION: synthetic oligonucleotide primer

<400> SEQUENCE: 13
gccagtttgg agagtattta c                                        21

<210> SEQ ID NO 14
<211> LENGTH: 21
<212> TYPE: DNA
<213> ORGANISM: artificial
<220> FEATURE:
<223> OTHER INFORMATION: synthetic oligonucleotide primer

<400> SEQUENCE: 14
gtaaatactc tccaaactgg c                                        21

<210> SEQ ID NO 15
<211> LENGTH: 30
<212> TYPE: DNA
<213> ORGANISM: artificial
<220> FEATURE:
<223> OTHER INFORMATION: synthetic oligonucleotide primer

<400> SEQUENCE: 15
ccgaattcat ggccgataag gctgggccgc                               30

<210> SEQ ID NO 16
<211> LENGTH: 57
<212> TYPE: DNA
<213> ORGANISM: artificial
<220> FEATURE:
<223> OTHER INFORMATION: synthetic oligonucleotide primer

<400> SEQUENCE: 16
gggcggccgc tagtgatggt gatggtgatg ctcggcgtgg ccgcggctgc tagcagg  57

<210> SEQ ID NO 17
<211> LENGTH: 19
<212> TYPE: DNA
<213> ORGANISM: artificial
<220> FEATURE:
<223> OTHER INFORMATION: synthetic oligonucleotide primer

<400> SEQUENCE: 17
gcgcgcgctt tttttttt                                            19

<210> SEQ ID NO 18
<211> LENGTH: 27
<212> TYPE: DNA
<213> ORGANISM: artificial
<220> FEATURE:
<223> OTHER INFORMATION: synthetic oligonucleotide primer

<400> SEQUENCE: 18
gataaggctg ggccgcagaa gaagagg                                  27

<210> SEQ ID NO 19
<211> LENGTH: 23
<212> TYPE: DNA
<213> ORGANISM: artificial
<220> FEATURE:
<223> OTHER INFORMATION: synthetic oligonucleotide primer

```
<400> SEQUENCE: 19
acaaatttaa caacacaccg ctg                                              23
```

VACCINE FOR RUNTING-STUNTING SYNDROME

This application is a continuation-in-part of International Application No. PCT/US2009/065259, filed Nov. 20, 2009, which claims the benefit of U.S. Provisional Application Ser. No. 61/116,396, filed Nov. 20, 2008; each of which are incorporated herein by reference in their entireties.

BACKGROUND

The ranting stunting syndrome (RSS) in chickens is an economically devastating disease with an unknown causative agent. The disease, also known as MAS, infectious stunting syndrome, broiler runting syndrome, pale bird syndrome, and helicopter syndrome, is characterized by a stunted growth of chickens, an increased feed conversion rate, and poor flock uniformity in the size of the chickens. With RSS, chickens develop diarrhea and show a higher susceptibility to other diseases. Furthermore, cystic enteropathic lesions have been described as one of the hallmarks of the disease. See, for example, Zalvala and Sellers, 2005, "Runting-stunting syndrome," The Informed Poultry Professional Issue 85:1-4; Zavala, 2006, "Ranting stunting syndrome (RSS) in broilers: In vivo studies;" available on the worldwide web at poultry-health.com/fora/inthelth/zavala_wpdc__06.pdf; Zavala and Barbosa, May 2006, "Ranting and stunting in broiler chickens," Apinco-Facta, May 2006, available on the worldwide web at poultry-health.com/fora/inthelth/zavala_apinco__06.pdf; Clark and Jones "Runting-Stunting Syndrome in Broilers," University of Arkansas, Division of Agriculture and published in Avian Advice, Spring 2008, available on the worldwide web at thepoultrysite.com/articles/1110/runting-stunting-syndrome-in-broilers; and Rebel et al., 2006, *World's Poultry Sci.* J. 62:17-29.

RSS is an economically devastating disease for the poultry industry. The causative agent is unknown, available diagnostic tests are very limited, and there is no vaccine to prevent or mitigate the disease. There is a need for improved diagnostic and therapeutic reagents and methods for the detection, treatment, and prevention of RSS.

SUMMARY OF THE INVENTION

The present invention includes a polypeptide including an amino acid sequence with at least about 75% sequence identity to the amino acid sequence of SEQ ID NO:2, a truncation, or fragment thereof.

The present invention includes a polypeptide including an amino acid sequence of SEQ ID NO:2, a truncation, or fragment thereof.

The present invention includes a polypeptide including at least ten consecutive amino acids of SEQ ID NO:2 or at least ten consecutive amino acids of residues 1 to 743 of SEQ ID NO:2.

The present invention includes a polypeptide having at least fifteen consecutive amino acids of SEQ ID NO:2 or at least ten consecutive amino acids of residues 1 to 743 of SEQ ID NO:2.

The present invention includes a polynucleotide sequence encoding a polypeptide of the present invention.

The present invention includes a polynucleotide sequence having at least about 75% sequence identity to the nucleotide sequence of SEQ ID NO:1, or a fragment thereof.

The present invention includes a polynucleotide sequence including the nucleotide sequence SEQ ID NO:1.

The present invention includes a polynucleotide sequence that hybridizes to the polynucleotide sequence of SEQ ID NO:1, or a complement thereof, at high stringency.

The present invention includes a polypeptide encoded by the polynucleotide sequence of the present invention.

The present invention includes a vector including a polynucleotide sequence of the present invention. In some embodiments, the vector may be an expression vector.

The present invention includes a host cell including a vector of the present invention.

The present invention includes an oligonucleotide primer selected from SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or a complement thereof.

The present invention includes a primer pair, wherein the primer pair is SEQ ID NO:3/SEQ ID NO:4; SEQ ID NO:9/SEQ ID NO:10; SEQ ID NO:5/SEQ ID NO:7; SEQ ID NO:5/SEQ ID NO:12; SEQ ID NO:5/SEQ ID NO:13; SEQ ID NO:8/SEQ ID NO:12; SEQ ID NO:8/SEQ ID NO:13; SEQ ID NO:11/SEQ ID NO:13, or SEQ ID NO:18/SEQ ID NO:19.

The present invention includes a primer pair, wherein a first primer is an oligonucleotide primer selected from SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or a complement thereof.

The present invention includes a primer pair, wherein a first primer is an oligonucleotide primer selected from SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or a complement thereof, and a second primer is an oligonucleotide primer selected from SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or a complement thereof.

The present invention includes a composition including one or more polypeptides of the present invention. In some embodiments, the composition further includes an adjuvant. In some embodiments, the composition further includes an antigenic determinant from one or more additional pathogens infectious to poultry.

The present invention includes an immunological composition for raising antibodies in poultry, the composition including one or more polypeptides of the present invention. In some embodiments, the composition further includes an adjuvant. In some embodiments, the composition further includes an antigenic determinant from one or more additional pathogens infectious to poultry.

The present invention includes a vaccine including one or more polypeptides of the present invention. In some embodiments, the vaccine further includes an adjuvant. In some embodiments, the vaccine further includes an antigenic determinant from one or more additional pathogens infectious to poultry.

The present invention includes an antibody that binds to a polypeptide of the present invention. In some embodiments, the antibody may be a monoclonal antibody. The present invention includes a host cell producing a monoclonal antibody of the present invention.

The present invention includes a diagnostic kit including one or more polypeptides of the present invention, one or more polynucleotides of the present invention, one or more primers or primer pairs of the present invention, and/or one or more antibodies of the present invention.

The present invention includes a recombinant virus including one or more polypeptides of the present invention.

The present invention includes a recombinant virus including one or more of the polynucleotides of the present invention.

The present invention includes a method of detecting exposure to runting-stunting syndrome (RSS) in a bird, the method including determining that an antisera sample obtained from the bird specifically binds to a polypeptide of the present invention.

The present invention includes a method of mitigating the symptoms of runting-stunting syndrome (RSS) in poultry, the method including administering one or more of the polypeptides of the present invention, a composition of the present invention, a vaccine of the present invention, one or more antibodies of the present invention, and/or one or more polynucleotide sequences of the present invention.

The present invention includes a method of producing anti-RSS antibodies in poultry, the method including administering one or more of the polypeptides of the present invention, a composition of the present invention, a vaccine of the present invention, and/or one or more polynucleotide sequences of the present invention.

The present invention includes a method of preventing runting-stunting syndrome (RSS) in poultry, the method including administering one or more of the polypeptides of the present invention, a composition of the present invention, a vaccine of the present invention, one or more antibodies of the present invention, and/or one or more polynucleotide sequences of the present invention.

The present invention includes a method of producing immunity to runting-stunting syndrome (RSS) in poultry, the method including administering one or more of the polypeptides of the present invention, a composition of the present invention, a vaccine of the present invention, and/or one or more polynucleotide sequences of the present invention.

The present invention includes poultry produced by a method of the present invention.

In some embodiments of the methods of the present invention, the polypeptide, composition, vaccine, or polynucleotide sequence is administered to a breeder hen. The present invention includes a breeder hen produced by such a method. The present invention includes the offspring of the breeder hen. In some embodiments, the offspring of the breeder hen may demonstrate serum antibodies that bind to a polypeptide having SEQ ID NO:2, a truncation, or fragment thereof, and/or reduced symptoms of RSS.

The present invention includes a method of making the polypeptide, composition, vaccine, polynucleotide sequence, vector, primer, antibody, host cell, diagnostic kit, or recombinant virus of the present invention.

The present invention includes a method of detecting a runting stunting syndrome (RSS) infectious agent in a sample, the method including detecting the hybridization of a polynucleotide as described herein to the sample.

The present invention includes a method of detecting a runting stunting syndrome (RSS) infectious agent in a sample, the method including producing a polymerase chain reaction (PCR) amplification product with one or more oligonucleotide primer as described herein or a primer pair as described herein.

The terms "comprises" and variations thereof do not have a limiting meaning where these terms appear in the description and claims.

Unless otherwise specified, "a," "an," "the," and "at least one" are used interchangeably and mean one or more than one.

BRIEF DESCRIPTION OF THE FIGURES

FIGS. 1A-1B. RSS caused a severe weight depression and cystic enteropathy in young broiler chickens. In FIG. 1A, 150 one-day-old commercial broiler chickens were placed on chicken litter from a RSS affected farm (RSS+) or on fresh shavings (RSS−). Twelve days after placement chicken were weight and average of the body weights in gram (g) is shown. The standard deviation is depicted by bars. In FIG. 1B, the presence of cystic enteropathy was histological examined by the analysis of two cross sections of the duodenal loop of each bird. The number of sections which showed lesion out of the total number of analyzed sections is shown in parenthesis. The number of lesions per affected cross section is indicated at the left axis.

FIGS. 2A-2B. Gut content of RSS negative chickens did not induce lesion or weight depression. One-day old chickens (15 in each group) were inoculated either with PBS (Con/2) or gut content of RSS negative chickens (RSS−/2). As positive control the same numbers of chickens were inoculated with gut content of chickens showing retarded growth and typical lesions in the gut (RSS+/3). In FIG. 2A, the body weight of the chickens was determined before (grey columns) or after (black columns) inoculation. The standard deviation is depicted by bars. In FIG. 2B, the duodenal loop was evaluated for the presence of enteropathic lesions. The number of lesions per section is shown at the left axis. The total number of affected section is showed below the horizontal axis.

In FIG. 3A, 15 one-day-old commercial broiler chickens were inoculated either with PBS (Con), with either gut content of RSS+ affected chicken (RSS+/3) or filtered gut content (RSS+/3filt) or filtered and chloroform treated gut content (RSS+/3filtCF). Before (grey box) and after the experiment (black box) the chicken were weight and the average of the weight in gram is shown. The standard deviation is show by error bars. In FIG. 3B, two cross sections of the duodenal loop of each bird was histological examined for the presence of signs of cystic enteropathy. The number of sections which showed enteropathic lesions out of the total number of analyzed sections is shown in parenthesis. The number of enteropathic lesions per affected cross section is indicated at the right axis.

In FIG. 8A, one-day-old progeny from the vaccinated (VACC) and non-vaccinated (NON-VAC) broiler breeders were divided randomly in groups 12 chickens each. The body weight was determined before (grey column) and after challenge (black column). The body weight is shown in gram (g) and the scale is shown at the left axis. The standard deviations are indicated by error bars. In FIG. 8B, 12 days after challenge the duodenal loop was taken during necropsy from chickens of all groups and a cross section was histological examined. The presence of enteropathic lesions in the non-vaccinated/challenged and vaccinated/challenged groups are shown by columns. The number of enteropathic lesions per section is indicated at the left axis.

In FIG. 9A, one-day-old progeny from vaccinated (VACC) and non-vaccinated (NON-VAC) broiler breeders were divided randomly into two groups of 15 chickens each. The body weight was determined before (grey column) and after challenge (black column) and is shown in gram (g) as indicated at the left axis. Calculated standard deviations are indicated by error bars. The weight difference was calculated between the control group and the challenged group within the non-vaccinated and vaccinated hatch mates. The weight gain was calculated between day of hatch and day 12 within each group. In FIG. 9B, 12 days after challenge the duodenal loop was taken during necropsy from chickens of all groups and a cross section was histological examined. The presences of histological lesions in the non-vaccinated/challenged and vaccinated/challenged groups are shown by columns. The number of enteropathic lesions per section is indicated at the left axis.

In FIG. 11A, one-day-old progeny from vaccinated (VACC) and non-vaccinated (NON-VAC) broiler breeders were divided randomly into two groups of 12 chickens each. The body weight was determined before (grey column) and after challenge (black column) and is shown in gram (g) as indicated at the left axis. Calculated standard deviations are indicated by error bars. The weight difference was calculated between the control group and the challenged group within the non-vaccinated and vaccinated hatch mates. The weight gain was calculated between day of hatch and day 12 within each group. In FIG. 11B, 12 days after challenge the duodenal loop was taken during necropsy from chickens of all groups and a cross section was histological examined. The presences of histological enteropathic lesions in the non-vaccinated/challenged and vaccinated/challenged groups are shown by columns. The number of lesions per section is indicated at the left axis.

FIG. 12. The nucleotide (SEQ ID NO:1) and deduced amino acid (SEQ ID NO:2) sequences of the astrovirus capsid protein ORF.

FIG. 14A-14I. Determination of the presence of antibodies specific for the capsid protein of the new chicken astrovirus using the recombinant antigen. Serum samples from chickens of different ages (in weeks) and different US states were investigated for the presence of antibodies directed against the capsid protein of the new chicken astrovirus in a dilution of 1:100. Each time five positive (specific for the astrovirus capsid protein) and SPF chicken serum samples were used as controls. Serum samples from broiler (B), broiler breeder (BB), and layer (L) were investigated. FIG. 14A presents data for Farm 1, Georgia and Farm 1, North Carolina. FIG. 14B presents data for Farm 2, Georgia. FIG. 14C presents data for Farm 3, Georgia. FIG. 14D presents data for Farm 2, North Carolina and Farm 1, Louisiana (7 weeks of age). FIG. 14E presents data for Farm 1, Virginia and Farm 1, Alabama. FIG. 14F presents data for Farm 3, North Carolina, Farm 1, Maine, and Farm 1, Louisiana (49 weeks of age). FIG. 14G presents data for Farms 1 and 2, Alabama. FIG. 14H presents data for Farm 1, Indiana and Farm 1, South Carolina. And, FIG. 14I presents data for Farm 4, North Carolina, Farm 1, New Hampshire, and Farm 1, California.

FIG. 15. Reverse transcription-polymerase chain reaction (RT-PCR) to detect RNA of the new chicken astrovirus. RNA was purified from gut samples from chickens exposed to RSS-contaminated litter and used for RT-PCR using astrovirus specific primer. The annealing temperature during the PCR step varied from 50° C. to 55° C. The reactions products were separated on a 1.5% agarose gel. As negative control (con) an in parallel treated PBS sample was used. An 100 bp DNA ladder was used as marker (M).

DETAILED DESCRIPTION OF ILLUSTRATIVE EMBODIMENTS OF THE INVENTION

Figure 3:
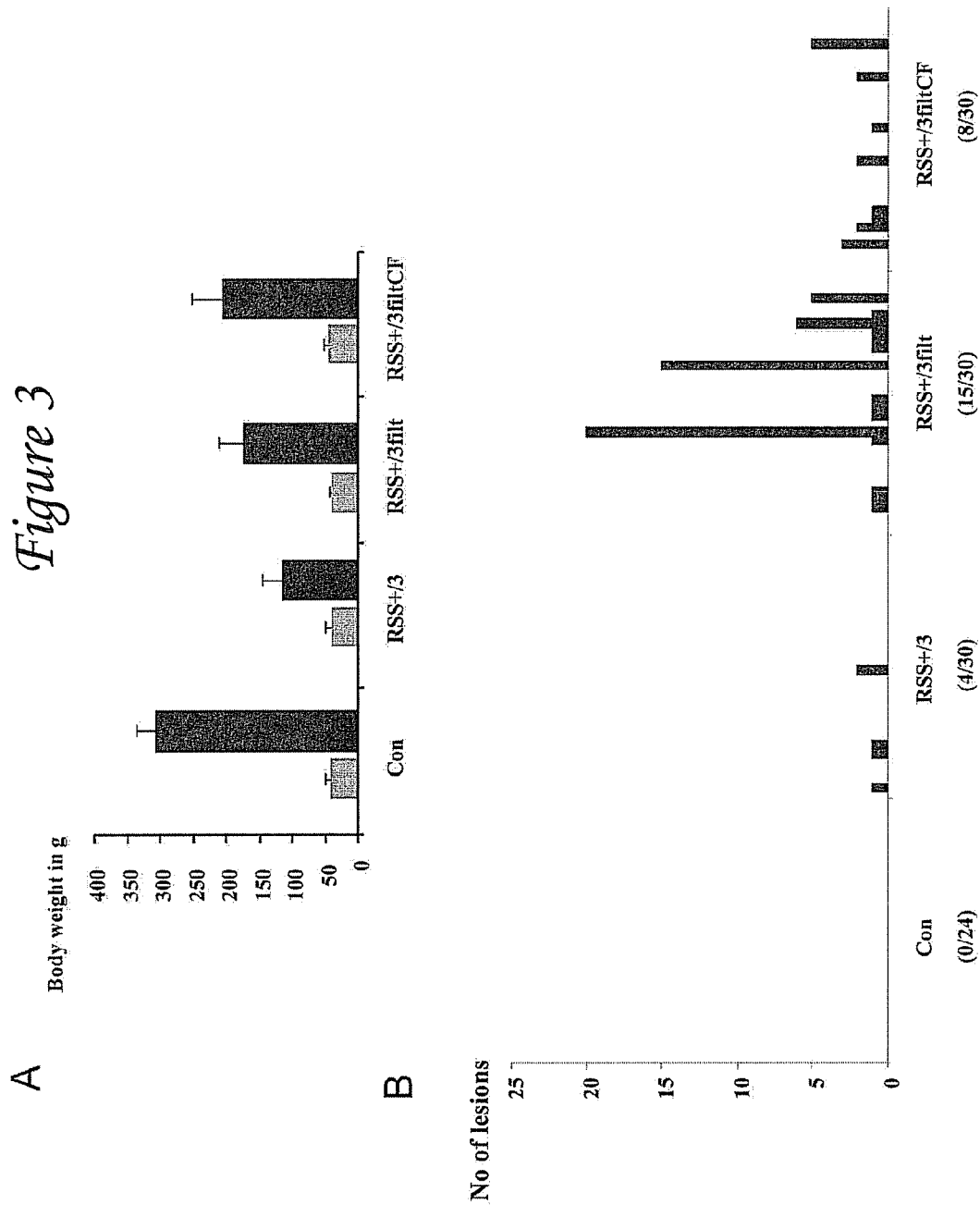
FIGS. 3A-3B. RSS is caused by a non-enveloped virus.
Figure 4:
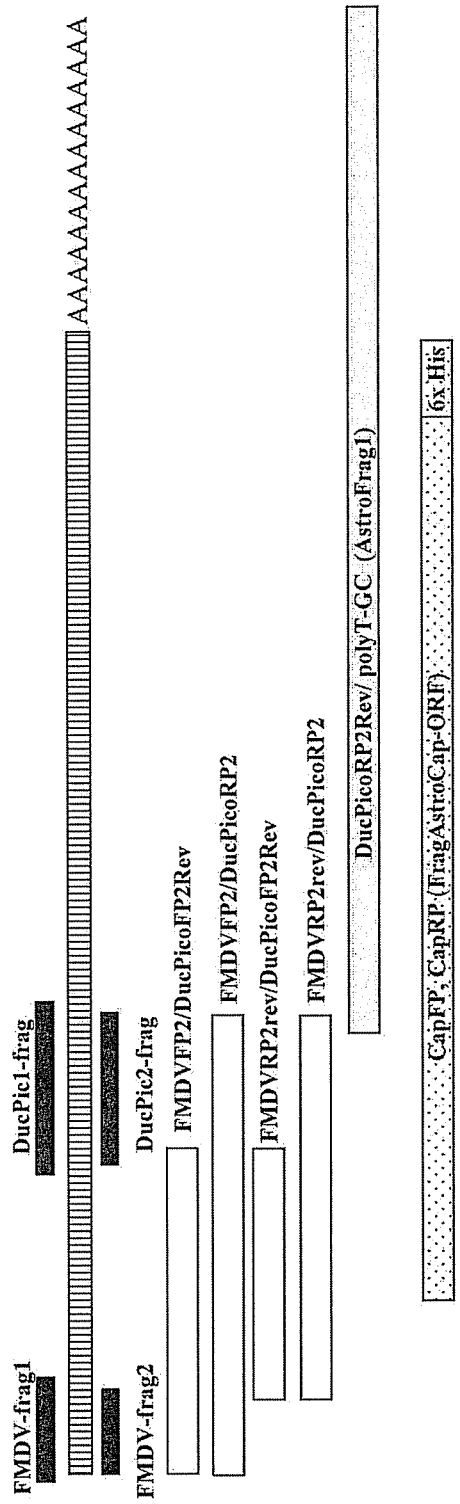
FIG. 4. Cloning of the open reading frame of the astrovirus capsid protein. The obtained RT-PCR fragments and the determined astrovirus sequence are shown. The determined astrovirus sequence is shown as a striped box. The initially amplified RT-PCR fragments are shown as black boxes. RT-PCR fragments amplified with different primer pair combinations (in parenthesis) are depicted as open box. The amplified RT-PCR fragment encompassing the open reading frame of the astrovirus capsid protein with a 6×His at its C-terminus are indicated as dotted box.
Figure 5:
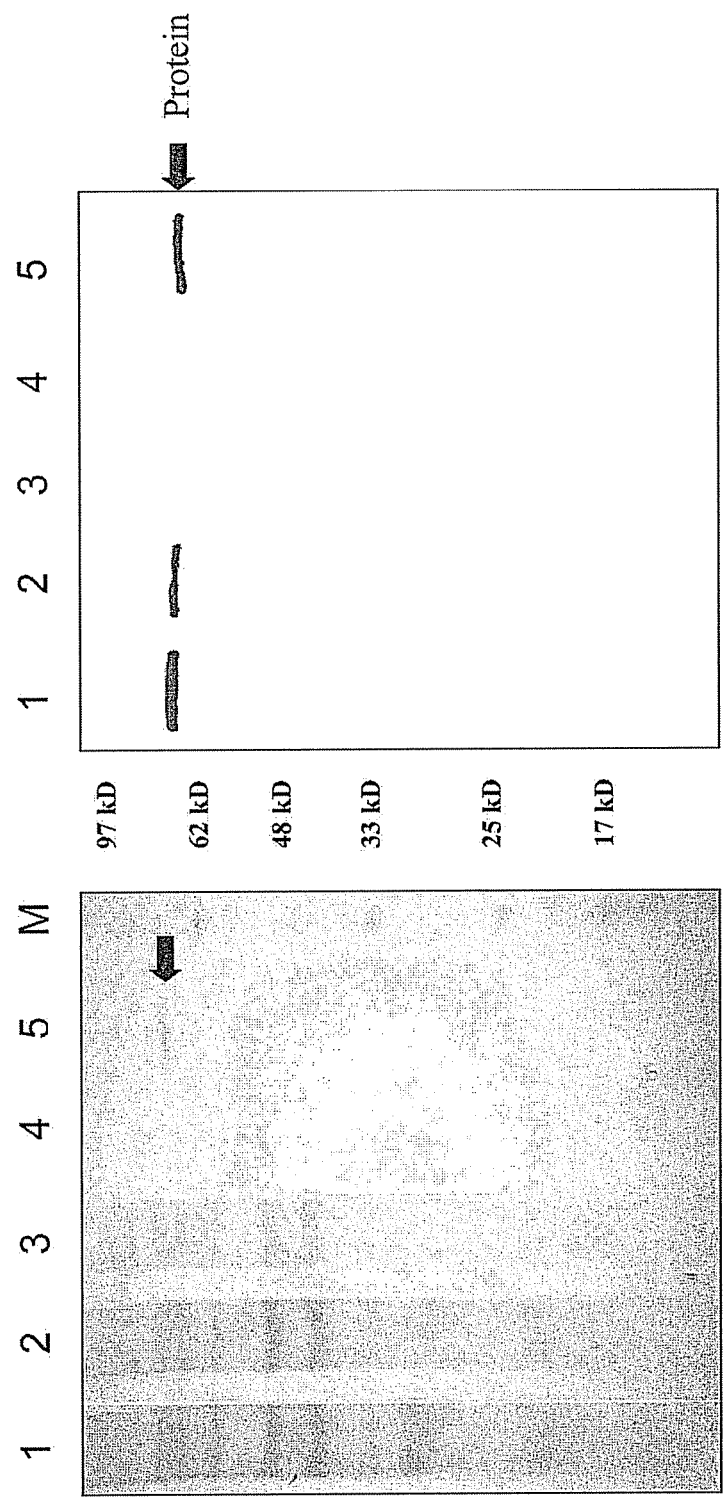
FIG. 5. Purification of the recombinant astrovirus capsid protein. Samples of lysed cells (1), of a lysate after centrifugation (2), of the centrifugation supernatant incubation with Talon (3), the flow through after the wash (4) and the eluate (5) were separated in 12% polyacrylamide gel by SDS-PAGE. The gels were either stained or a Western blot analysis was performed using an anti His mAb. The binding of the mAbs was visualised by chemoluminiscence using a peroxidase-labeled anti-mouse goat serum. A molecular mass marker (M) is shown and the position of the recombinant protein is marked by an arrow.
Figure 6:
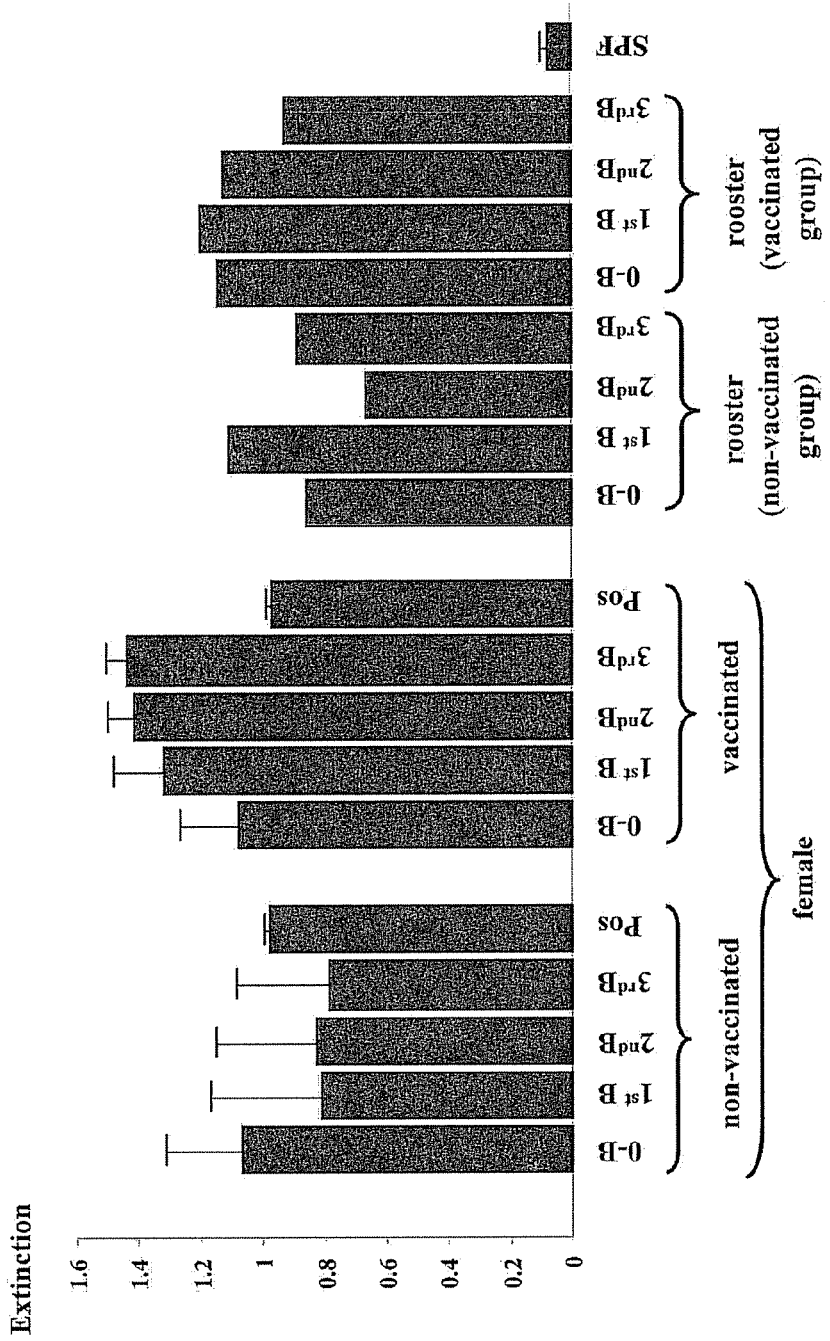
FIG. 6. Vaccination of broiler breeders with the recombinant astrovirus capsid protein induced an immune response in broiler breeder. A group of fifteen 22-week old commercial broiler breeder hens were vaccinated with an oil-emulsion vaccine containing the recombinant protein intramuscularly. One group of 15 hens and three roosters in both groups served as non-vaccinated control. All chickens were bled before the first (0-B) and 14 days after each of the three vaccinations (1st B, 2nd B, and 3rd B). The serum samples were analyzed in the astrovirus capsid protein ELISA along with the positive and negative (SPF) control serum. The extinction at a wave length of 405 nm is shown at the left axis.

With the present invention, a new viral sequence likely belonging to a virus of the family Astroviridae has been identified using the gut content of chickens affected with the runting stunting syndrome and the open reading frame of the viral capsid protein was cloned and a recombinant baculovirus generated. A purified protein was used as a vaccine in broiler breeders to provide maternal derived antibodies for the protection of the offspring. The presence of specific antibodies was monitored by an ELISA assay. The offspring of vaccinated breeder hens were partially protected in a RSS challenge model.

The present invention includes diagnostic and therapeutic reagents and methods for the detection, treatment, and prevention of RSS. Molecular methods were employed to identify novel polynucleotide sequences and deduced polypeptide sequences associated with Runting Stunting Syndrome (RSS) which are capable of protecting poultry, including chickens, against RSS. As used herein, poultry includes domesticated birds that are kept for the purpose of collecting their eggs, or killing for their meat and/or feathers. These most typically are members of the superorder *Galloanserae* (fowl), especially the order *Galliformes* (which includes, for example, chickens, quail, turkeys, and grouse) and the family Anatidae (in order *Anseriformes*), commonly known as "waterfowl" (including, for example, ducks, geese, and swans). Poultry may also include other birds which are killed for their meat, such as pigeons or doves or birds considered to be game, like pheasants.

With the present invention, a cloning approach targeting small round viruses (Picornaviridae) was used. The nucleotide sequences of the RNA dependent RNA polymerases (RdRp) are the most conserved sequence within RNA virus families. Using degenerate primers based on RdRp sequences of several members of the Picornaviridae family, RT-PCR fragments were amplified and sequenced. Using several approaches, a 1.8 kilobase pair (kbp) fragment was amplified. A blastn search in the NCBI database did not identify any similar sequences. The blastn search of the in silico translated amino acid sequence showed a 34% similarity to a turkey astrovirus capsid amino acid sequence and a 37% similarity to a turkey astrovirus 3 amino acid sequence. The sequence likely encodes a capsid protein of an astrovirus.

The coding sequences of the open reading frame (ORF) of the capsid protein were amplified, cloned and sequenced using molecular techniques. The open reading frame of the encoding sequence was amplified again to clone the ORF encoding a C-terminal located 6×His tag sequence into the plasmid vector pFastBacDual (Invitrogen). A recombinant baculovirus was generated using the Bac-To-Bac technology (Invitrogen). The recombinant baculovirus was used to infect insect cells (Sf9). The His-tagged protein representing the astrovirus capsid protein was purified using affinity-chromatography. The purified recombinant protein was used to vaccinate broiler breeder hens along with non-vaccinated controls. The experimental vaccine contained the recombinant protein in an oil emulsion vaccine based on Freund's incomplete adjuvant. In addition, an indirect ELISA was established to detect antibodies in serum following vaccination and in serum samples from the field. The broiler breeder hens were vaccinated three times, and antibody titers monitored using the ELISA system as described above. The offspring of the vaccinated and non-vaccinated broiler breeders were challenged using our previously described RSS challenge model. Twelve days after challenge it was observed that the offspring of vaccinated breeder hens showed a 27% decreased weight gain in comparison to their unchallenged hatch mates.

In contrast, the challenged offspring of the non-vaccinated hens showed about 50% lower weight gain in comparison to their unchallenged hatch mates. Histological examination of the duodenal loop of the challenged and non-challenged offspring showed that in the non-challenged controls of both groups (vaccinated as well as non-vaccinated) no cystic enteropathy was observed. In the duodenum of the challenged offspring from vaccinated breeder hens, a significantly lower number of cystic enteropathic lesions was observed compared to the challenged offspring of the non-vaccinated controls.

After two vaccinations, the vaccinated broiler breeders showed a significant increase in antibody titers against the recombinant protein compared to the non-vaccinated control birds as measured by ELISA. Similarly, elevated antibody titers against the recombinant protein were observed in the offspring the vaccinated breeders. In challenge experiments using the offspring from hens receiving three vaccinations, a level of protection was observed against RSS. Progeny from vaccinated/challenged hens gained significantly more weight compared to offspring from the non-vaccinated/challenged controls. In addition, the number and size of enteropathic cystic lesions in the small intestine was significantly reduced in the offspring from vaccinated hens. Thus, the vaccine of the present invention will be useful in efforts to control RSS.

The present invention includes polypeptides having the amino acid sequence shown in SEQ ID NO:2, truncations and fragments thereof. Truncations include, but are not limited to, amino acid sequences in which one, two, three, four, five, six, seven, eight, nine, ten, or more amino acids are removed from the amino terminus of the amino acid sequence SEQ ID NO:2 and/or one, two, three, four, five, six, seven, eight, nine, ten, or more amino acids are removed from the carboxy terminus of the amino acid sequence SEQ ID NO:2. Truncations may include the amino acid sequence of SEQ ID NO:2 in which the one, two, three, four, five, six, seven, eight, nine, ten, or more of the C terminal His residues have been removed, including, but not limited to the fragment of amino acid 1 to 743 of SEQ ID NO:2. Truncations of the present invention may include further C- and N-terminal truncations of the polypeptide including amino acids residues 1 to 743 of SEQ ID NO:2.

Fragments include, but are not limited to, for example, fragments having about 5, about 10, about 15, about 20, about 25, about 50, about 75, about 100, about 150, about 200, about 250, about 300, about 350, about 400, about 450, about 500, about 550, about 600, about 650, and about 700 consecutive amino acid residues of the sequence of SEQ ID NO:2 or of residues 1 to 743 of SEQ ID NO:2. Fragments also include, for example, fragments of a size range of any combination of the above fragment sizes.

Fragments include, but are not limited to, for example, fragments having at least 5, at least 10, at least 15, at least 20, at least 25, at least 50, at least 75, at least 100, at least 150, at least 200, at least 250, at least 300, at least 350, at least 400, at least 450, at least 500, at least 550, at least 600, at least 650, and at least 700 consecutive amino acid residues of SEQ ID NO:2 or of a polypeptide including residues 1 to 743 of SEQ ID NO:2.

The present invention includes polypeptides having an amino acid sequence with at least about 75% sequence identity with the amino acid sequence of SEQ ID NO:2, polypeptides having an amino acid sequence with at least about 75% sequence identity with amino acids 1 to 743 of SEQ ID NO:2, polypeptides having an amino acid sequence with at least about 80% sequence identity with the amino acid sequence of SEQ ID NO:2, polypeptides having an amino acid sequence with at least about 80% sequence identity with amino acids 1 to 743 of SEQ ID NO:2, polypeptides having an amino acid sequence with at least about 85% sequence identity with the amino acid sequence of SEQ ID NO:2, polypeptides having an amino acid sequence with at least about 85% sequence identity with amino acids 1 to 743 of SEQ ID NO:2, polypeptides having an amino acid sequence with at least about 90% sequence identity with the amino acid sequence of SEQ ID NO:2, polypeptides having an amino acid sequence with at least about 90% sequence identity with amino acids 1 to 743 of SEQ ID NO:2, polypeptides having an amino acid sequences with at least about 95% sequence identity with the amino acid sequence of SEQ ID NO:2, polypeptides having an amino acid sequence with at least about 95% sequence identity with amino acids 1 to 743 of SEQ ID NO:2, polypeptides having an amino acid sequences with at least about 96% sequence identity with the amino acid sequence of SEQ ID NO:2, polypeptides having an amino acid sequence with at least about 96% sequence identity with amino acids 1 to 743 of SEQ ID NO:2, polypeptides having an amino acid sequences with at least about 97% sequence identity with the amino acid sequence of SEQ ID NO:2, polypeptides having an amino acid sequence with at least about 97% sequence identity with amino acids 1 to 743 of SEQ ID NO:2, polypeptides having an amino acid sequences with at least about 98% sequence identity with the amino acid sequence of SEQ ID NO:2, polypeptides having an amino acid sequence with at least about 98% sequence identity with amino acids 1 to 743 of SEQ ID NO:2, polypeptides having an amino acid sequences with at least about 99% sequence identity to the amino acid sequence of SEQ ID NO:2, and polypeptides having an amino acid sequence with at least about 99% sequence identity with amino acids 1 to 743 of SEQ ID NO:2, truncations, or fragments thereof.

The present invention includes polypeptides having an amino acid sequence with one, two, three, four, five, six, seven, eight, nine, ten, eleven, twelve, thirteen, fourteen, fifteen, sixteen, seventeen, eighteen, nineteen, twenty, or more amino acid changes from the amino acid sequence of SEQ ID NO:2, truncations, or fragments thereof. Such amino acid changes include, but are not limited to, conservative amino acid changes.

The present invention includes polypeptides encoded by a polynucleotide that hybridizes to the nucleotide sequence of SEQ ID NO:1 under stringent hybridization conditions, and fragments thereof. Stringent hybridization conditions may be, for example, 6×SSC, 5×Denhardt, 0.5% sodium dodecyl sulfate (SDS), and 100 µg/ml fragmented and denatured salmon sperm DNA hybridized overnight at 65° C. and washed in 2×SSC, 0.1% SDS at least one time at room temperature for about 10 minutes followed by at least one wash at 65° C. for about 15 minutes followed by at least one wash in 0.2×SSC, 0.1% SDS at room temperature for at least 3 to 5 minutes. Such polypeptides may be bound by an antibody that specifically binds to a polypeptide including amino acid residues 1 to 743 of SEQ ID NO:2.

Also included in the present invention are compositions including one or more of the polypeptides described herein. Such a composition may include pharmaceutically acceptable carriers or diluents. Carriers include, for example, stabilizers, preservatives and buffers. Suitable stabilizers include, for example, SPGA, carbohydrates (such as sorbitol, mannitol, starch, sucrose, dextran, glutamate or glucose), proteins (such as dried milk serum, albumin or casein) or degradation products thereof. Suitable buffers include, for example, alkali metal phosphates. Suitable preservatives include, for example, thimerosal, merthiolate and gentamicin. Diluents, include, but are not limited to, water, aqueous buffer (such as buffered saline), alcohols, and polyols (such as glycerol).

The present invention includes immunogenic compositions and vaccines including one or more of the polypeptides described herein. Such a compositions and vaccine may be administered as the active component to immunize a bird to elicit an antibody response to RSS and/or induce immunity against RSS. Immunity may include the induction of a significant higher level of protection in a population of birds after vaccination compared to an unvaccinated group.

An immunogenic composition or vaccine of the present invention may also include one or more compounds with adjuvant activity. Suitable compounds or compositions for this purpose include aluminum hydroxide, aluminum phosphate, aluminum oxide, plant oils, animal oils, oil-in-water or water-in-oil emulsion based on, for example a mineral oil, such as Bayol F™ or Marcol 52™, Complete Freund's adjuvant, incomplete Freund's adjuvant, or a vegetable oil such as vitamin E acetate, and saponins.

An immunogenic composition or vaccine of the present invention may also contain one or more stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

An immunogenic composition or vaccine of the present invention may further include one or more immunogens derived from other pathogens infectious to poultry. Such immunogens may be derived from, for example, Marek's disease virus (MDV), infectious bronchitis virus (IBV), Newcastle disease virus (NDV), egg drop syndrome (EDS) virus, turkey rhinotracheitis virus (TRTV), poxvirus, or reovirus.

An immunogenic composition or vaccine of the present invention may be administered by any suitable known method of inoculating poultry including nasally, ophthalmically, by injection, in drinking water, in the feed, by exposure, in ovo, maternally, and the like. The immunogenic composition or vaccine may be administered by mass administration techniques such as by placing the vaccine in drinking water or by spraying the animals' environment. When administered by injection, the immunogenic composition or vaccine may be administered parenterally. Parenteral administration includes, for example, administration by intravenous, subcutaneous, intramuscular, or intraperitoneal injection.

The immunogenic compositions or vaccines of the present invention may be administered to poultry, and although vaccines according to the present invention may be used effectively in chickens, other poultry, such as, for example, turkeys, guinea fowl, ducks, and partridges may be successfully inoculated. Chickens include, but are not limited to, hens, roosters, broilers, roasters, breeder, the offspring of breeder hens, and layers. The vaccine of the present invention may be administered to poultry before or after hatching. Poultry may receive a vaccine at a variety of ages. For example, broilers may be vaccinated in ovo, at one-day-old, in ovo, or at 2-3 weeks of age. Laying stock or reproduction stock may be vaccinated, for example, at about 6-12 weeks of age and boosted at about 16-20 weeks of age. Such laying stock or reproduction stock may be vaccinated at about 6, at about 7, at about 8, at about 9, at about 10, at about 11, or at about 12 weeks of age. Such laying stock or reproduction stock may be boosted at about 16, at about 17, at about 18, at about 19, or at about 20 weeks of age. The offspring of such laying stock or reproduction stock may demonstrate an antibody titer to a polypeptide including amino acid residues 1 to 743 of SEQ ID NO:2, which may prevent or mitigate the symptoms of an RSS infection in the offspring.

The present invention includes polynucleotide sequences that encode the various, polypeptides described herein, truncations, or fragments thereof. For example, the present invention includes polynucleotide sequences that encode the amino acid sequence of SEQ ID NO:2, a polypeptide including amino acid residues 1 to 743 of SEQ ID NO:2, truncations, or fragments thereof. The present invention includes the polynucleotide sequence of SEQ ID NO:1, truncation, or fragments thereof.

The present invention includes polynucleotide sequences with at least about 60% sequence identity, polynucleotide sequences with at least about 65% sequence identity, polynucleotide sequences with at least about 70% sequence identity, polynucleotide sequences with at least about 75% sequence identity, polynucleotide sequences with at least about 80% sequence identity, polynucleotide sequences with at least about 85% sequence identity, polynucleotide sequences with at least about 90% sequence identity, polynucleotide sequences with at least about 95% sequence identity, polynucleotide sequences with at least about 96% sequence identity, polynucleotide sequences with at least about 97% sequence identity, polynucleotide sequences with at least about 98% sequence identity, and polynucleotide sequences with at least about 99% sequence identity to the polynucleotide sequence of SEQ ID NO:1, truncations, or fragments thereof. Such a polynucleotide may encode a polypeptide that is bound by an antibody that specifically binds to a polypeptide including amino acid residues 1 to 743 of SEQ ID NO:2.

The present invention includes polynucleotide sequences that hybridize to the nucleotide sequence of SEQ ID NO:1 under various stringency conditions, and fragments thereof. Stringency conditions include, but are not limited to, moderate and high stringency. High stringency hybridization conditions may be, for example, 6×SSC, 5×Denhardt, 0.5% sodium dodecyl sulfate (SDS), and 100 µg/ml fragmented and denatured salmon sperm DNA hybridized overnight at 65° C. and washed in 2×SSC, 0.1% SDS at least one time at room temperature for about 10 minutes followed by at least one wash at 65° C. for about 15 minutes followed by at least one wash in 0.2×SSC, 0.1% SDS at room temperature for at least 3 to 5 minutes. Such a polynucleotide may encode a polypeptide that binds to an antibody that specifically binds to a polypeptide including amino acid residues 1 to 743 of SEQ ID NO:2.

The present invention includes polynucleotide sequences having a substitution of one, two, three, four, five, six, seven, eight, nine, ten, or more nucleotides from that of SEQ ID NO:1. The present invention also includes the polynucleotide sequences described herein in which codon usage has been adapted to optimize expression in a given host cell. For example, codon usage may be adapted to optimize for expression in host cells including, but not limited to, baculovirus, yeast, E. coli, poultry, or human cells. Such adaptation can be carried out by techniques know in the art. Such a polynucleotide may encode a polypeptide that binds to an antibody that binds to a polypeptide including residues 1 to 743 of SEQ ID NO:2.

The present invention includes primers, including, but not limited to, any of the primers described herein, and primers that can be used to generate the sequence of SEQ ID NO:1, or a fragment thereof, in a PCR reaction. In some embodiments, a primer may include at least 5, at least 10, at least 15, at least 20, at least 25, at least 30, at least 35, or at least 40 nucleotide residues. In some embodiments, a primer may include no more than 10, no more that 15, no more than 20, no more than 25, no more than 30, no more than 35, no more than 40, no more than 45, no more than 50, no more that 55, or no more than 60 nucleotide residues. Such nucleotides residues may be consecutive sequences of SEQ ID NO:1 or its complement. Such nucleotides residues may hybridize to SEQ ID NO:1 or its complement. Such primers may include, for example, SEQ ID NO:3, SEQ ID NO:4, SEQ ID NO:5, SEQ ID NO:6, SEQ ID NO:7, SEQ ID NO:8, SEQ ID NO:9, SEQ ID NO:10. SEQ ID NO:11, SEQ ID NO:12, SEQ ID NO:13, SEQ ID NO:14, SEQ ID NO:15, SEQ ID NO:16, SEQ ID NO:18, or SEQ ID NO:19, complements thereof, and primers derived from such sequences. Also included are primer pairs including at least one of the primers described herein. Such primer pairs may include, for example, SEQ ID NO:3/SEQ ID NO:4; SEQ ID NO:9/SEQ ID NO:10; SEQ ID NO:5/SEQ ID NO:7; SEQ ID NO:5/SEQ ID NO:12; SEQ ID NO:5/SEQ ID NO:13; SEQ ID NO:8/SEQ ID NO:12; SEQ ID NO:8/SEQ ID NO:13; SEQ ID NO:11/SEQ ID NO:13; or SEQ ID NO:18/SEQ ID NO:19, complements thereof, or primers derived from such sequences. Also included in the present invention are the amplification products produced by such primers.

The present invention provides a recombinant vector containing one or more of the nucleotide sequences described herein. Such a recombinant vector may be an expression vector. Such a recombinant vector may also include other sequences such as expression control sequences, markers, amplifying genes, signal sequences, promoters, and the like, as is known in the art. Useful vectors for this purpose are plasmids, and viruses such as baculoviruses, paramyxovirus, coronavirus, herpes virus (for example, herpes virus of turkeys (HVT)) and pox viruses, for example, fowl pox virus, and the like.

The present invention also includes host cells transformed with a polynucleotide sequence described herein and host cells transformed with a recombinant vector described herein. The host cell may be, for example, a eukaryotic or a prokaryotic host cell. Suitable examples are E. coli, insect cell lines such as Sf-9, chicken embryo fibroblast (CEF) cells, chicken embryo kidney (CEK) cells, African green monkey Vero cells and the like.

The present invention includes antibodies that bind to a polypeptide as described herein, and various antibody fragments, also referred to as antigen binding fragments, which include only a portion of an intact antibody, generally including an antigen binding site of the intact antibody and thus retaining the ability to bind antigen. Such an antibody, or antigen binding fragment thereof, may, for example, bind to the polypeptide of SEQ ID NO:2. Such an antibody, or antigen binding fragment thereof, may bind to a polypeptide including residues 1 to 743 of SEQ ID NO:2. Such an antibody, or antigen binding fragment thereof, may bind to a polypeptide including at least five, at least ten, at least eleven, at least twelve, at least thirteen, at least fourteen, at least fifteen, at least twenty, at least twenty five, at least thirty, at least forty, at least fifty, at least seventy-five, at least one hundred, at least two hundred, at least three hundred, at least four hundred, at least five hundred, at least six hundred, or at least seven hundred consecutive amino acid residues of SEQ ID NO:2 and/or residues 1 to 743 of SEQ ID NO:2. In some embodiments, an antibody of the present invention does not bind to a 6×His peptide. Such antibodies may be used to detect or isolate a polypeptide as described herein, or an RSS-associated polypeptide or virus from a sample.

Examples of antibody fragments include, for example, Fab, Fab', Fd, Fd', Fv, dAB, and F(ab')2 fragments produced by proteolytic digestion and/or reducing disulfide bridges and fragments produced from an Fab expression library. Antibodies include, but are not limited to, polyclonal antibodies and monoclonal antibodies. The antibodies of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins can have both heavy and light chains. An array of IgG, IgE, IgM, IgD, IgA, and IgY heavy chains can be paired with a light chain of the kappa or lambda form.

An intact antibody molecule has two heavy (H) chain variable regions (abbreviated herein as VH) and two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined. Each VH and VL is composed of three CDR's and four FRs, arranged from amino-terminus to carboxy-terminus in the following order: FR1, CDR1, FR2, CDR2, FR3, CDR3, FR4. The present invention includes an antibody with the heavy chain, the light chain, the heavy chain variable region, the light chain variable region, and/or one or more complementarity determining regions of a monoclonal antibody of the present invention. The present invention includes bispecific or bifunctional antibodies. A bispecific or bifunctional antibody is an artificial hybrid antibody having two different heavy/light chain pairs and two different binding sites. Bispecific antibodies can be produced by a variety of methods including fusion of hybridomas or linking of F(ab') fragments.

The antibodies of the invention can be from any animal origin, including birds and mammals. In some embodiments, the antibodies are human, murine, rat, donkey, sheep, rabbit, goat, guinea pig, camel, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins.

Monoclonal antibodies of the present invention can be obtained by various techniques familiar to those skilled in the art. For example, spleen cells from an animal immunized with a desired antigen are immortalized, commonly by fusion with a myeloma cell. Monoclonal antibodies can be isolated and purified from hybridoma cultures by techniques well known in the art. Other known methods of producing transformed B cell lines that produce monoclonal antibodies may also be used. In some embodiments, the antibody can be recombinantly produced, for example, produced by phage display or by combinatorial methods. Such methods can be used to generate human monoclonal antibodies.

Also included in the present invention are phage display libraries expressing one or more hypervariable regions from a monoclonal antibody of the present invention, and clones obtained from such a phage display library. A phage display library is used to produce antibody derived molecules. Gene segments encoding the antigen-binding variable domains of antibodies are fused to genes encoding the coat protein of a bacteriophage. Bacteriophage containing such gene fusions are used to infect bacteria, and the resulting phage particles have coats that express the antibody-fusion protein, with the antigen-binding domain displayed on the outside of the bacteriophage. Phage display libraries can be prepared, for example, using the Ph.D.™-7 Phage Display Peptide Library Kit (Catalog No. E8100S) or the Ph.D.™-12 Phage Display Peptide Library Kit (Catalog No. E8110S) available from New England Biolabs Inc., Ipswich, Mass. See also, Smith and Petrenko, 1997, Chem Rev; 97:391-410.

The present invention includes antibodies and binding proteins that include one or more of the complementarity determining regions (CDR) of a monoclonal antibody of the present invention. Such an antibody or binding protein may bind to a polypeptide including amino acid resides 1 to 743 of SEQ ID NO:2, or a fragment thereof.

The antibodies of the present invention may be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}$I, $^{123}$I, $^{125}$I, $^{131}$I), carbon ($^{14}$C), sulfur ($^{35}$S), tritium ($^{3}$H), indium ($^{111}$In, $^{112}$In, $^{113m}$In, $^{115m}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru. Techniques for conjugating such moieties to antibodies are well-known. Antibodies of the present invention include derivatives of antibodies that are modified or conjugated by the covalent attachment of any type of molecule to the antibody. Such antibody derivatives include, for example, antibodies that have been modified by glycosylation, acetylation, pegylation, phosphorylation, amidation, derivatization by known protecting/blocking groups, proteolytic cleavage, or linkage to a cellular ligand or other protein. Any of numerous chemical modifications can be carried out by known techniques, including, but not limited to, specific chemical cleavage, acetylation, formylation, and metabolic synthesis of tunicamycin. Additionally, the derivatives can contain one or more non-classical amino acids.

The present invention includes isolated polypeptides, polynucleotides, and antibodies. As used herein, "isolated" refers to material removed from its original environment (e.g., the natural environment if it is naturally occurring), and thus is altered "by the hand of man" from its natural state.

The antibodies of the present invention may "specifically bind to" or be "specific for" a particular polypeptide or an epitope on a particular polypeptide. Such an antibody is one that binds to that particular polypeptide or epitope on a particular polypeptide without substantially binding to any other polypeptide or polypeptide epitope.

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells.

The present invention includes kits employing one or more of the polypeptides, polynucleotides, and/or antibodies described herein. Such kits may provide for the administration of a polypeptide of the present invention to an animal in order to elicit an immune response. Such kits may provide for the detection of a polypeptide, antibody or polynucleotide, for example, for the detection of RSS infection or exposure of a subject to an RSS agent. Kits of the present invention may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by well known methods, preferably to provide a sterile, contaminant-free environment. As used herein, the term "package" refers to a solid matrix or material such as glass, plastic, paper, foil, and the like, capable of holding within fixed limits a polypeptide. Kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

The present invention includes a variety of methods employing one or more of the polypeptides, polynucleotides, compositions, vaccines, vectors, host cells, recombinant viruses, and/or antibodies described herein.

For example, the polypeptides, polynucleotides, vectors, host cells, recombinant viruses, vaccines, and compositions thereof, may be administered to elicit an immune response in poultry or other animals. The immune response may or may not confer protective immunity. An immune response may include, for example, a humoral response and/or a cell mediated response. Such an immune response may result in a reduction or mitigation of the symptoms of future RSS infection. Such an immune response may prevent a future RSS infection in poultry. Such an immune response may be a humoral immune response, a cellular immune response, and/or a mucosal immune response. A humoral immune response may include an IgG, IgM, IgA, IgD, and/or IgE response. The determination of a humoral, cellular, or mucosal immune response may be determined by any of a variety of methods, including, but not limited to, any of those described herein.

The induction of an immune response may include the priming and/or the stimulation of the immune system of poultry to respond to a future challenge with a RSS infectious agent, providing immunity to future RSS infections. The induction of such an immune response may serve as a protective response, generally resulting in a reduction of the symptoms of RSS in poultry, receiving a challenge with an RSS infectious agent. Preferably, the poultry will display either a therapeutic or protective immunological response such that resistance to new infection will be enhanced and/or the clinical severity of the disease reduced. Such protection may be demonstrated by either a reduction or lack of the symptoms associated with RSS, including, but not limited to, any of those described herein. In some embodiments, a method of the present invention may be used as a vaccination method, vaccinating poultry for the treatment and/or prophylaxis of infection by an RSS infectious agent or a related organism. Any of a wide variety of available assays may be used to determine the effectiveness of the vaccination method of the present invention, including, but not limited to, any of those described herein. For example, clinical scores (including, but not limited to, fecal color, diarrhea, abdominal gut fill, and attitude), histopathology, lesion index (including, but not limited, to size and/or number of cystic enteropathic lesions in the small intestine), percent mortality, or weight gain measurement may be used. Such determinations may be in comparison to non-immunized/RSS challenged, non-immunized/non-RSS challenged, and/or immunized/non-RSS challenged control animals.

The polypeptides, polynucleotides, vectors, host cells, recombinant viruses, vaccines, and compositions thereof, may be administered to poultry to prevent RSS. The polypeptides, polynucleotides, vectors, host cells, recombinant viruses, vaccines, and compositions thereof, may be administered to poultry at any of a variety of life stages and/or ages; for example, to a breeder hen. The breeder hen may demonstrate serum antibodies that bind to a polypeptide including amino acid residues 1 to 743 of SEQ ID NO:2, or a fragment thereof, and/or reduced symptoms of RSS. The offspring of the breeder hen may demonstrate such antibodies and/or reduced symptoms of RSS.

The polypeptides, polynucleotides, vectors, host cells, recombinant viruses, vaccines, and compositions thereof may be administered to poultry or other animals, to produce antibodies. Other animals include, but are not limited to, mice, rat, donkey, sheep, rabbit, goat, guinea pig, camel, and horse.

The present invention also includes methods for the detection of RSS agents and antibodies to RSS, including the detection of an RSS infection, detection of previous exposure of an animal to an RSS agent, and/or a determination of the effectiveness of an RSS vaccination effort, or other RSS-control effort, in an animal or a population of animals. The present invention includes methods of detecting or determining exposure of a subject to an RSS infectious agent, the method including detecting the presence of an antibody that binds to a polypeptide as described herein. Antibodies may be detected in samples obtained from the subject, including a biological sample, such as, for example, a tissue or fluid sample isolated from a subject, including but not limited to, for example, blood, plasma, serum, fecal matter, urine, bone marrow, bile, spinal fluid, lymph tissue and lymph fluid, samples of the skin, external secretions of the skin, respiratory, intestinal, and genitourinary tracts, tears, saliva, milk, blood cells, organs, biopsies, or eggs. One or more polypeptides as described herein may be labeled with one or more of the detectable markers known to the skilled artisan. In some aspects, a polypeptide may be bound to a solid substrate. A polypeptide may be included as positive and/or negative controls in antibody based detection methods and kits. In some embodiments, sera from specific pathogen free (SPF) poultry may serve as a negative control.

The present invention includes methods of detecting an RSS infectious agent in a biological or environmental sample by contacting the sample with one or more of the antibodies described herein. As used herein, a biological sample refers to a sample of tissue or fluid isolated from a subject, including but not limited to, for example, blood, plasma, serum, fecal matter, urine, bone marrow, bile, spinal fluid, lymph tissue and lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

Antibodies may be detected by any of a variety of methods, including, but not limited to, the methods described herein and any suitable method available to the skilled artisan. Immunoassays that can be used include, but are not limited to, competitive and non-competitive assay systems using techniques such as BIAcore analysis, FACS (Fluorescence activated cell sorter) analysis, immunofluorescence, immunocytochemistry, Western blots, radio-immunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art. With any of the methods of the present invention, the intensity of a signal from an anti-RSS antibody may be indicative of the relative amount of the anti-RSS antibody in a sample when compared to a positive and negative control reading.

Methods of the present invention may employ detecting the hybridization of a polynucleotide of the present invention to a sample. Such a method may employ producing a polymerase chain reaction (PCR) amplification utilizing at one or more of the oligonucleotide primers described herein. Such primers include, for example, SEQ ID NO:3, SEQ ID NO:4, SEQ ID NO:5, SEQ ID NO:6, SEQ ID NO:7, SEQ ID NO:8, SEQ ID NO:9, SEQ ID NO:10. SEQ ID NO:11, SEQ ID NO:12, SEQ ID NO:13, SEQ ID NO:14, SEQ ID NO:15, SEQ ID NO:16, SEQ ID NO:18, or SEQ ID NO:19, complements thereof, and primers derived from such sequences. Such a method may employ producing a polymerase chain reaction (PCR) amplification utilizing a primer pair described herein. Such primer pairs include, for example, SEQ ID NO:3/SEQ ID NO:4; SEQ ID NO:9/SEQ ID NO:10; SEQ ID NO:5/SEQ ID NO:7; SEQ ID NO:5/SEQ ID NO:12; SEQ ID NO:5/SEQ ID NO:13; SEQ ID NO:8/SEQ ID NO:12; SEQ ID NO:8/SEQ ID NO:13; SEQ ID NO:11/SEQ ID NO:13; or SEQ ID NO:18/SEQ ID NO:19, complements thereof, or primers derived from such sequences. Such methods may be used for detecting an RSS infectious agent in a biological or environmental sample.

The polypeptides, polynucleotides, and/or antibodies may be labeled with one or more of the detectable markers known to the skilled artisan. In some aspects, the polypeptides, polynucleotides, and/or antibodies may be bound to a solid substrate. Any of the diagnostic methods of the present invention may include the additional step of providing a report or print out of the results. The sample may be any sample in which RSS antibodies, antigens, or nucleotides are present, for example, a blood, serum or tissue sample. Such methods and kits may provide for the detection of exposure of one or more birds to an RSS infectious agent or an RSS vaccine. Such methods and kits may provide for the determination of the effectiveness of a anti-RSS vaccination or immunization effort or other type of RSS control effort including determining if a sera sample from an individual binds to a polypeptide as described herein, for example, binds to a polypeptide including SEQ ID NO:2 and/or a fragment thereof, and/or binds to a polypeptide including amino acid residues 1 to 743 of SEQ ID NO:2, and/or a fragment thereof. Such methods and kits may provide for the detection of infectious RSS agents in environmental samples.

The present invention is illustrated by the following examples. It is to be understood that the particular examples, materials, amounts, and procedures are to be interpreted broadly in accordance with the scope and spirit of the invention as set forth herein.

Example 1

Development of a Recombinant Vaccine Against Runting and Stunting Syndrome in Chickens Runting and stunting syndrome (RSS) has been recognized since the late 1970s. RSS has also been referred to as mal adsorption syndrome (MAS), infectious stunting syndrome, broiler runting syndrome, pale bird syndrome and helicopter syndrome. All associations to this disease manifestation have been based on clinical signs and microscopical lesions in organs of the small intestine. Clinical signs are growth retardation (stunted chickens), ruffled feathers, and slight diarrhea. Histopathologic changes of the stunted chicks include villous atrophy of the small intestine and a distention of crypts of Lieberkühn (Nili et al., 2007, *Comp Clin Pathol;* 16:161-6; and Otto et al., 2006, Avian Dis; 50:411-8). Although environmental, nutritional and management issues play an important role in the manifestation of this syndrome, infectious agents, namely viruses have been implicated as etiologic agent(s). Specifically, reoviruses, rotaviruses, enteroviruses, astroviruses and other small round viruses have been observed in the intestines and contents of clinically affected birds by virus isolation and/or electron microscopy. See, for example, McNulty et al., 1984, Avian Path; 13:429-439; Reece and Frazier, 1990, *Avian Path;* 19:723-758; Frazier and Reece, 1990, *Avian Path;* 19:759-777; Goodwin Davis, and Player, 1993, *Avian Dis;* 37:229-233; and Goodwin et al., 1993, *Avian Dis;* 37:451-458. A similar enteric syndrome has been described for young turkey poults, Poult Enteritis and Mortality Syndrome (PEMS). Viral etiologies associated with this disease are Turkey coronavirus (TCV), Turkey Astrovirus (TAstV) and turkey reovirus (Guy, 1998, *Poultry Sci;* 77:1166-1175; Heggen-Pey et al., 2002, *Avian Dis;* 46:32-47; Kapczynski et al., 2002, *Virus Genes;* 25:95-100; Sellers et al., 2004, *Avian Dis;* 48:531-539; and Spackman et al., 2005, *Avian Pathol;* 34:291-296).

Avian reoviruses (ARV) are commonly isolated from healthy chickens but are also associated with several diseases, namely viral arthritis and MAS. The relationship of reoviruses in cases of MAS is not well understood. Reoviruses isolated from cases of MAS have been shown to cause lesions in the duodenum, jejunum and ilieum with (Decaesstecker et al., 1986, *Avian Pathol;* 15:769-782; Kouwenhoven et al., 1988, *Avian Pathol;* 17:879-892) or without an associated weight suppression (Songserm et al., 2003, *Vet. Res;* 34:285-

295). In addition, reovirus antigen staining was observed in intestinal lesions of experimentally infected broilers with an MAS homogenate. However, the intestinal lesions associated with avian reovirus MAS isolates nor antigen staining was present in the crypt of the Lieberkuhn (Songserm et al., 2000, *Avian Dis;* 44:556-567), where numerous cysts have been observed in affected birds. Other studies performed by researchers in Europe (Meulemanns et al., 1986, "Runting syndrome in broiler chickens. Experimental reproduction studies," In: Acute virus infections of poultry. J. B. McFerran and M. S. McNulty, eds. Martinus Nijhoff, Dordrecht, The Netherlands. pp. 115-124; and McFerran and McNulty, 1986, "Recent advances in enterovirus infections of birds," In: Acute virus infections of poultry. J. B. McFerran and M. S. McNulty, eds. Martinus Nijhoff, Dordrecht, The Netherlands. pp. 195-201) and Australia (Pass et al., 1982, Vet. Rec; 110: 386-387) found little evidence that avian reovirus played a significant role in RSS.

Avian nephritis virus (ANV), a recently classified astrovirus has also been implicated in RSS. This virus was initially classified as a picornavirus (entero- and entero-like virus), based on morphological features, until the full length genome was sequenced in 2000 (Imada et al., 2000, *J. Virol;* 74:8487-8493). At this time, ANV was re-classified as a new genus in the family Astroviridae. Early investigations into the etiologies of RSS identified entero-like viruses in young chicks. A crude inoculum containing this virus and a reovirus consistently produced slow feathering, fecal changes and depressed weight gains in broilers inoculated at one day of age (McNulty et al., 1984, *Avian Path;* 13:429-439). Co-infection of avian reovirus and ANVs isolated from broilers exhibiting a runting syndrome has been examined in two lines of SPF chickens (Shirai et al., 1990, *Avian Dis;* 34:295-303). In single challenge with the reovirus resulted in weight suppression in both lines of chickens. However, single challenge with the ANY resulted in growth depression and nephritis in only one of the two lines. Challenge of the same line with ANV at day of age and avian reovirus at three days of age resulted in growth depression less severe than the single avian reovirus challenge. These results suggest a breed-related susceptibility for ANY.

Diagnostic tools available for detecting enteric viruses of poultry were previously limited to electron microscopy. However, advancements in molecular technology have made RT-PCR and PCR valuable tools for detecting these viruses which are typically difficult to culture. We previously developed a multiplex RT-PCR for detection of TAstV, coronavirus and reovirus (Spackman et al., 2004, *Avian Dis;* 49:86-91) in feces of turkey poults experiencing PEMS. In TAstV experimentally inoculated turkey poults, viral replication was limited to cells along the base and sides of the villi, primarily in the distal small intestine and cecum.

Material and Methods

Establishment of a Challenge Model for RSS.

Chicken litter was collected and transported from a farm with clinical signs of RSS to experimental isolation houses (colony houses). The chicken litter was distributed onto the floor of a colony house with an approximate area of 10 m$^2$ (RSS+). In parallel, fresh shavings were distributed onto the floor of another colony house (RSS-). In each house, 150 one-day-old broiler chickens from a commercial farm were raised. Water and feed was provided ad libitum. Twelve days after placing the birds in the colony houses, the birds were removed and humanely euthanized with $CO_2$ and body weights recorded. Post mortem necropsy was performed, the small intestine was removed and tissue samples from the duodenal loop were harvested and fixed in neutral buffered formalin for subsequent histological examination. The remaining sections of the small intestine were homogenized in a Waring blender, diluted 1:1 with sterile PBS and aliquots were stored frozen at −80 C. In subsequent experiments, 15 one-day-old commercial broiler chickens were gavaged by feeding tube with 1 ml of the homogenized gut of either RSS+ or RSS− birds. One group was left untreated to serve as true negative controls. All three groups were held in HEPA filtered Horsfal Bauer units with forced air positive pressure. Water and feed was provided ad libitum. Twelve days after inoculation the birds were euthanized with $CO_2$ and the duodenal loop was harvested, fixed in neutral buffered formalin and examined for histological lesions.

Based on the assumption that RSS has a viral etiology, commercial broiler chickens were gavaged as described above infected with three different inocula, non-treated gut content, filtered gut content and filtered/chloroform treated gut content. The gut content was obtained from RSS+ chickens. Before filtration, the gut content was centrifuged at 3500×g for 30 minutes (min) at 4 C. The supernatant was obtained and centrifuged at 16000×g for 10 minutes at 4 C. Supernatant was subsequently filtered through a 0.45 μm filter using a 10 ml syringe. The obtained filtrate was filtered again using a 0.22 μm filter. The final filtrate was left untreated or was mixed with 0.5 volume of chloroform, repeatedly vortexed for 15 seconds (s) in a one minute interval over 15 minutes. The suspension was centrifuged at 3500×g for 30 minutes at 4 C and the upper phase was removed and used for further experiments. In next experiments, one-day-old broiler commercial broiler chickens were held in Horsfal Baur units with positive pressure HEPA filtered air. Water and food was supplied ad libitum. The chickens were gavaged with one of the following treatments: 1) 1 ml of the non-treated RSS+ gut content, 2) filtered RSS+-gut content, 3) filtered/chloroform treated RSS+-gut content or 4) no treatment. The chickens were monitored daily. At day 12 after infection, the chickens were euthanized with $CO_2$ and body weights recorded. During necropsy, the duodenal loop was harvested, fixed in neutral buffered formalin and histologically examined. The tissue samples of all experiments were fixed in 10% buffered formalin and routinely processed, embedded, sectioned and stained with hematoxylin and eosin (H&E).

Delineation of Oligonucleotides.

Based on the results from the experiments described above and the hypothesis that the infectious agent is a small round virus, available sequences of RNA-dependent RNA polymerases (RdRp) of the virus family Picornaviridae were aligned using the ClustalW (available on the worldwide web at ebi.ac.uk/Tools/clustalw2/index.html), due to a possibly existing higher similarity between the single nucleotide sequences of the RdRp. Based on the similarities, two groups of viruses were fowled and the sequences investigated, one, polioviruses, coxsackieviruses including duck picornaviruses (DuckPico), and, two, aphtoviruses (FMDV). The requirement for a possible primer pair was that the resulting RT-PCR fragment should not be larger than 350 bp. The resulting primer pairs (FMDVFP1 (SEQ ID NO:3)/FMDVRP1 (SEQ ID NO:4); DucpicoFP1 (SEQ ID NO:9)/DucpicoRP1 (SEQ ID NO:10)) were used for RT-PCR (see Table 1).

TABLE 1

Oligonucleotides used for cloning of the Astrovirus sequences

| Name | Sequence | Orientation | Location[a] | Genbank No[b] | Virus |
|------|----------|-------------|-------------|---------------|-------|
| FMDVFP1 | GGGTTTTACAAACCTGTGATG (SEQ ID NO: 3) | sense | 7786-7806 | DQ248888 | FMDV |
| FMDVRP1 | CCGCACACGGCGTTCACCC (SEQ ID NO: 4) | antisense | 7982-7920 | DQ248888 | FMDV |
| FMDVFP2 | TAAGGACTTTGTGGTCTATG (SEQ ID NO: 5) | sense | | | |
| FMDVFP2Rev | CATAGACCACAAAGTCCTTA (SEQ ID NO: 6) | antisense | | | |
| FMDVRP2 | GGCCTCGATGCTTGGGAGCC (SEQ ID NO: 7) | antisense | | | |
| FMDVRP2Rev | GGCTCCCAAGCATCGAGGCC (SEQ ID NO: 8) | antisense | | | |
| Ducpico FP1 | AGATTGATTGAAGCCTCCAGTTTG (SEQ ID NO: 9) | sense | 6505-6528<br>7113-7136 | AY278552<br>AY563023 | Human poliovirus 2<br>Duck picornavirus |
| Ducpico RP1 | ATGSWDGTNCCHGARCABCCYGADGGCAT (SEQ ID NO: 10) | antisense | 6841-6869<br>7458-7486 | AY278552<br>AY563023 | Human poliovirus 2<br>Duck picornavirus |
| DucPicoFP2 | GGAAAGGAAGATGAGGGCATTG (SEQ ID NO: 11) | sense | | | |
| DucPicoFP2rev | CAATGCCCTCATCTTCCTTTCC (SEQ ID NO: 12) | antisense | | | |
| DucPicoRP2 | GCCAGTTTGGAGAGTATTTAC (SEQ ID NO: 13) | antisense | | | |
| DucPicoRP2Rev | GTAAATACTCTCCAAACTGGC (SEQ ID NO: 14) | sense | | | |
| poly-T-GC | GCGCGCGCTTTTTTTTTTT (SEQ ID NO: 17) | antisense | | | |
| CapFP | EcoRI<br>ccGAATTCATGGCCGATAAGGCTGGGCCGC (SEQ ID NO: 15) | sense | | | |
| CapRP | Not I<br>ggGCGGCCGCTAGTGATGGTGATGGTGATGCTCGGCGTGGCCGCGGCTGCTAGCAGG (SEQ ID NO: 16) | antisense | | | |

[a] Location of the oligonucleotides in agreement with the sequences of FMDV (foot and mouth disease virus), duck picornavirus, and human poliovirus 2
[b] NCBI genbank RNA Purification and RT-PCR.

Ten milliliters (ml) of the homogenized tissue samples were clarified by low speed centrifugation (3500×g for 20 min) and the supernatant was filtered using a 0.45 μM filter. The resulting fluid was ultracentrifuged at 174899×g for one hour. The resulting pellet was resuspended in 200 microliter (μl) sterile PBS. The RNA was purified by using the High-Pure-RNA-Isolation-Kit (Roche, Applied-Science). Reverse transcription-polymerase chain reaction (RT-PCR) was performed using SuperScript™ III One-Step RT-PCR System with Platinum® Taq (Invitrogen) following the standard protocol as provided by the manufacturer. For the amplification of the 3'end of the genomic RNA a RAMP-RT-PCR was performed. To this end the time from the annealing step to the extension step during PCR was set with an increment of 30% of the normal RAMP using the Eppendorf Mastercycler ep (Eppendorf, Hamburg, Germany).

Cloning and Sequence Analysis.

Amplified PCR fragments were cloned into the vector pCR2.1 using the TopoTA cloning kit (Invitrogen). Purified plasmid DNA was sequenced using the BigDye Terminator v3.1 Cycle Sequencing Kit (Applied Biosystems, Lincoln, Calif., USA). Resulting sequences were compared using the computer program Gene-Runner Version 3.1 (Hastings Software, Hudson, N.Y., USA). Subsequent data analysis was performed using online computer programs available on the worldwide web at expasy.org/tools/dna.html and ebi.ac.uk/Tools/clustalw2.

Generation of Recombinant Baculovirus Expressing the Astrovirus Capsid Protein.

For expression of the astrovirus capsid protein a recombinant baculovirus was generated based on the baculovirus transfer vector pFastBac™ Dual and the Bac-to-Bac® Baculovirus Expression System (Invitrogen, Carlsbad, Calif., USA). To construct an appropriate plasmid, a 2267 bp fragment was amplified by RT-PCR using a pair of oligonucleotides (CAP-FP (SEQ ID NO:15); CAP-RP (SEQ ID NO:16), see Table 1). The resulting RT-PCR fragment was eluted from a 1% agarose gel, cloned into pCR2.1 (CAP-pCR2.1) using the TopoTA cloning Kit (Invitrogen). After verification by sequencing, CAP-pCR2.1 was cleaved with EcoR I/Not I and the eluted DNA fragment encompassing the capsid protein coding region and a 6×His encoding region at its C-terminus was ligated into EcoR I/Not I cleaved baculovirus transfer vector pFastBac™ Dual to obtain pFAST-CAP. After verification of the nucleotide sequence a recombinant bacmid containing the ORF of the astrovirus capsid protein was generated using the Bac-to-Bac® Baculovirus Expression System (Invitrogen) following the protocols as provided by the manufacturer. Transfection and subsequent propagation of recombinant baculovirus was performed in Sf9 cells as recommended by the manufacturer using Cellfectin® (Invitrogen). Sf9 cells were cultivated in serum free medium (HyClone SFX-Insect, ThermoFisher) containing ampicillin (100 IU/ml) and streptomycin (100 ng/ml). The baculovirus expressing the astrovirus capsid protein (Cap-Bac) was used for infection of Sf9 cells at a MOI of 1. 72 h p.i. infected Sf9 cells were harvested by centrifugation at 1000×g for 10 min at 4° C. The sedimented cells were used either immediately for protein purification or stored at −20 C until purification. Protein purification was performed as previously described by Letzel et al. (2007).

Determination of the Virus Titer.

The $TCID_{50}$ was determined by indirect immunofluorescence. To this end, tenfold dilutions of the viral stock were performed in serum-free medium (HyClone SFX-Insect, ThermoFisher). 100 μl of Sf9 cells (300.000 cells/ml) were seeded into each well of a 96 well cell culture plate and infected with 100 μl of the appropriate virus dilution. Three days after inoculation, the cells were fixed with ice-cold ethanol and indirect immunofluorescence was performed using a monoclonal antibody (mAb) directed against Baculovirus V5 protein (mAb-V5, Sigma-Aldrich, St. Louis, Mo.) as primary antibody. As a secondary antibody, a FITC labeled goat anti-mouse IgG antibody (Jackson ImmunoResearch, West Grove, Pa.) was used. The $TCID_{50}$ was calculated using the formula of Reed and Muench (Reed and Muench, 1938, *Am. J. Epidemiol;* 27:493-497).

Detection of Recombinant Protein.

For Western blot analysis, samples were separated by sodium dodecylsulphate-12% polyacrylamide gel electrophoresis (SDS-PAGE) and transferred onto a nitrocellulose membrane. The membrane was incubated with blocking solution using 5% non-fat dry milk in TBST (150 mM NaCL, 10 mM Tris, pH 8.0, 0.05% Tween 20) for one hour. After washing in TBST the membranes were incubated with the anti-6× His mAb (Clone His-1, Sigma-Aldrich, ST. Louis, Mo., USA) as primary antibodies and peroxidase-labeled goat anti-mouse IgG (Jackson ImmunoResearch, West Grove, Pa.) as secondary antibody. The binding of the antibodies was monitored using a chemiluminescent substrate, Immobilon Western (Millipore, Billerca, Mass.) and Gel Logic 2200 (Carestream Health, New Haven, Conn.). For monitoring of the recombinant protein purification, samples were separated by sodium dodecylsulphate-12% polyacrylamide gel electrophoresis (SDS-PAGE) and stained with Imperial Protein Stain (ThermoScientific, Rockford, Ill., USA) following the manufacturers instructions.

Development of ELISA for the Detection of Astrovirus Capsid Specific Antibodies in Chicken Sera.

For ELISA, the protein detector ELISA kit (KPL, Gaithersburg, Md.) was used. The antigen was diluted in coating buffer to a final concentration of 500 ng/ml and 50 μl were added in each well of a 96-well flat bottom plate (FisherBrand, Santa Clara, Calif.). After incubation over night at 4° C., non-bound antigen was removed, wells were rinsed three times with wash solution (KPL, Gaithersburg, Md.) and 100 μl blocking solution were added (KPL, Gaithersburg, Md.). The plate was incubated for 45 min at 37° C. Following the washing procedure, 50 μl of diluted sera (1:100) were pipetted into the wells and incubated for one hour at 37° C. and rinsed three times with wash solution. Finally 50 μl of 1:1000 diluted peroxidase conjugated goat anti-chicken serum (KPL, Gaithersburg, Md.) were added. After incubation for one hour at 37° C., the plate was washed three times, 50 μl of peroxidase substrate solution (KPL, Gaithersburg, Md.) were added and the plate incubated for 15 min at room temperature. The enzymatic reaction was stopped by adding 50 μl of stop solution per well (KPL, Gaithersburg, Md.). The optical density (OD) values were measured at 405 nanometers (nm) using an ELISA reader (ELX 808, BioTek, Winooski, Vt.).

To obtain a standard serum from chicken, five 21-day-old SPF leghorn chicken were bleed and vaccinated as described below. Per chicken, 500 μl of the purified protein (250 μg) were mixed with Freund's incomplete adjuvant and a stabile emulsion was obtained by ultrasonic using Branson Sonifier 150 at level 2. Appropriate controls were left unvaccinated. The chickens were vaccinated three times at intervals of four weeks. At each time point prior to vaccination and three weeks following final vaccination, the chickens were bled and the serum was tested for reactivity in the described ELISA system. Four weeks following the final vaccination, a final bleed was obtained from the chickens and euthanized with $CO_2$.

Vaccination of Broiler Breeders.

One group of fifteen 21-week-old broiler breeder hens was vaccinated with the purified recombinant protein and a second group was left non-vaccinated. In both groups three broiler roosters were present. One group of hens was vaccinated three times (week 22, 26, 30) intramuscularly in the breast muscle with the experimental vaccine produced as described above. The roosters were not vaccinated and held as sentinel controls. No adverse effect in the breast muscle was observed during the duration of the experiments. Before vaccination and two weeks after each vaccination, blood was drawn from the brachial vein to obtain serum samples. The serum samples were monitored by the recombinant protein ELISA.

Challenge Experiments in Commercial Broiler Chicken.

Starting at fourteen days following the second and third vaccination, eggs were collected from both groups and chickens were hatched separately. From each hatch, two groups of fifteen chickens were weighed and placed into a Horsfal Bauer isolation unit and given water and food ad libitum. One group of chickens from each vaccination group was challenged by a gavage of filtered gut content from RSS affected chickens. One group was mock-challenged with PBS. The chickens were monitored daily. From additional progeny not used for the experiments, blood samples were taken and evaluated by the recombinant protein ELISA. Twelve days after infection chickens were euthanized by $CO_2$ and weighed. At necropsy the duodenal loop was taken for histopathological examination. The tissue sample taken was a cross section of the duodenal loop just above the tip of the pancreas including the ascending and descending portions of the loop.

Results

Runting-Stunting-Syndrome is Caused by Non-Enveloped Viruses.

In order to establish a challenge model for RSS in commercial broilers, chicken litter from an affected farm was transported to a colony house and 150 one-day-old commercial broiler chickens were placed on that litter (RSS+/1). In parallel 150 commercial broiler chickens were placed on fresh shavings (RSS−/1). During the experiment RSS+/1 chickens developed slight diarrhea, ruffled and dirty feathers, and lassitude. The control chickens (RSS−/1) showed no clinical signs. Twelve days after infection, chickens were euthanized, weighed and necropsy was performed. The macroscopic inspection of the RSS+/1 chickens revealed a difference in size compared to the RSS−/1 control chickens. The ventral abdomen of the RSS+/1 chicken was swollen in a number of chickens. Macroscopic lesions during necropsy of the RSS+/1 chickens consisted of a thinning of small intestines, gaseous ceacae, swollen and dark liver, massive filled bile, and enlarged spleen. Comparison of body weights showed that RSS+/1 chickens showed an approximate 50% weight depression in comparison to the RSS− chicken (FIG. 1). For histological examination from each duodenal loop, two sections were cut and following H&E staining, scored for the presence and number of lesions per section. In 28 out of 60 sections, lesions typical for cystic enteropathy in the RSS+/1 group were observed (FIG. 1). The number of lesions per section varied between 1 and 10.

Based on the results obtained, we performed the next experiment where fifteen one-day-old commercial broiler chickens were inoculated with minced gut content of either RSS+/1 chickens (RSS+/2) or RSS−/1 chickens (RSS−/2). One group was mock inoculated with PBS (Con/2). All three groups were held in Horsfal Bauer units with positive pressure. Twelve days after inoculation the chickens were evaluated. The macroscopic inspection of the RSS+/2 chickens showed distention of the abdomen, retarded growth, dirty feathers, and signs of diarrhea. At RSS−/2 chickens as well as Con/2 chickens, no clinical signs were observed. The average weight of the RSS+/2 chickens was 53% below the control chickens (Con/2) whereas the weight of the RSS−/2 chickens showed a not significant weight reduction of 8% in comparison to the controls (FIG. 2A). Macroscopic lesions of the abdominal organs of RSS+/2 chickens were consistent with the signs of RSS+/1 chickens. Abdominal organs of the RSS−/2 and the control chickens (Con/2) showed no macroscopic lesions. The histological examination of the duodenal loop showed the presence of cystic enteropathy and shorter gut villi of RSS+/2 chickens in comparison to RSS−/2 and control chickens (Con/2) where no microscopical lesions were observed (FIG. 2B). These results show that using a small group of chickens the macroscopic and microscopic lesions could be observed in RSS+ chickens.

This challenge model was further refined. To this end the gut content of RSS+/1 chicken was centrifuged and filtered, as described in the Material and Methods section. Fifteen one-day-old broiler chickens were orally inoculated with either the untreated gut content (RSS+/3), the filtered gut content (RSS+/3filt), or the filtered and chloroform treated gut content (RSS+/3filtCF). One group was mock inoculated with PBS (Con). The chickens were weighed before inoculation and 12 days after inoculation (FIG. 3A). The weight depression of the group receiving the non-treated material (RSS+/3) was 64% in comparison to the non-treated control group. In this group three out of 15 chickens died during the experiment. The group which was inoculated with the filtered material showed a weight depression of 45% whereas the filtered and CHCL3-treated material caused a weight depression of 33%. The difference in body weight between the RSS+/3filt group and the RSS+/3filtCF group was not statistically significant. Macroscopic lesions were not observed in the control group whereas in the group inoculated with the non-treated material, the filtered, and the filtered/chloroform treated material, macroscopic lesions were observed as described above. The data resulting from the histology showed that microscopic lesions in the duodenal loop were observed even after treatment with chloroform (FIG. 3B). Based on this data it was concluded that the causative agent for RSS is a non-enveloped virus whereas the presence of other agents (such as bacteria, fungi) might have an impact on the severity of the disease.

Cloning of the Open Reading Frame of the Astrovirus Capsid Protein.

Based on the above performed experiments we decided to clone nucleotide sequences which might be the genomic information of a virus which might cause the clinical picture of the RSS. Since it has been described that small round viruses were found consistently in the gut content of RSS affected chicken, oligonucleotides focusing on RdRp sequences of picornaviruses were delineated. For RNA purification filtered gut content of RSS+/1 and RSS−/1 was used in standard RT-PCR using two primer sets of primer pairs (FMDVFP1 (SEQ ID NO:3)/FMDVRP1 (SEQ ID NO:4); and Ducpico FP1 (SEQ ID NO:9)/Ducpico RP1 (SEQ ID NO:10)). The RT-PCR using the primer pair FMDVFP1/FMDVRP1 revealed an cDNA fragment of approximately 280 bp (FMDV-frag1) whereas by using the second primer pair a cDNA fragment of approximately 500 bp was amplified (DucPic1-frag). The RT-PCR using RNA from the gut content of RSS−/1 resulted in no fragment. In parallel, PCR was performed without an RT step and no fragment was amplified which indicated that the template for the cDNA fragments was RNA. Both fragments resulting from the RT-PCR were eluted from the gel and cloned using the Topo TA cloning system. Sequence analysis using Blastn search (NCBI database) showed no similarities with any nucleotide sequence present in the database. The next experiments were performed to elucidate if both fragment belong to one RNA molecule or to different RNA's. To this end, nested, internal primer were delineated which should amplify a cDNA fragment if both previous RT-PCR fragments belonged to one RNA (see Table 1) and RT-PCR were performed using RNA from RSS+/1. As expected the primer pairs FMDVFP2 (SEQ ID NO:5)/FMDVRP2 (SEQ ID NO:7) and DucpicoFP2 (SEQ ID NO:11)/DucpicoRP2 (SEQ ID NO:13) resulted in RT-PCR fragments of the expected size, 232 bp (FMDV-frag2) and 418 bp (DucPic-frag2), respectively. Sequence analysis confirmed the identity of the sequence of the amplified fragments with the previous sequences of the appropriate fragments DucPic1-frag and FMDV-frag1.

Next, a number of RT-PCR's were performed. Each primer of each fragment was used for an RT-PCR using the primer of the other fragment. In addition, the reverse-complementary sequences of each primer (see Table 1) were also used since the location of each RT-PCR fragment to each other was unknown. Only four combinations resulted in amplification of fragments (FMDVFP2 (SEQ ID NO:5)/DucPicoFP2Rev (SEQ ID NO:12), FMDVFP2 (SEQ ID NO:5)/DucPicoRP2 (SEQ ID NO:13); FMDVRP2rev (SEQ ID NO:8)/DucPicoFP2Rev (SEQ ID NO:12), FMDVRP2rev (SEQ ID NO:8)/DucPicoRP2 (SEQ ID NO:13)). All fragments were cloned and sequenced. The sequence of the longest fragment (FMDVFP2 (SEQ ID NO:5)/DucPicoRP2 (SEQ ID NO:13)) comprised all sequences of the other three fragments.

Based on this result, it was concluded that both sequence fragments which were amplified during our first RT-PCR were part of a single RNA molecule. The sequence was used for a blastn search in the NCBI database but no similarities were found. The nucleotide sequence was now in silico translated in all six open reading frames using a software program available on the worldwide web at expasy.org/tools/dna.html. The highest similarity (53%) at the amino acid level was found with the capsid precursor protein of a turkey astrovirus 2 (GENBANK Accession Number AAV37186) and the RNA dependent RNA polymerase of turkey astrovirus 2 (61%, GENBANK Accession Number ABX46565) using a blastp search using all six proteins sequences resulting form the in silico translation. Thus the amplified sequence likely belonged to an astrovirus which has not been described yet. From the probable capsid protein open reading frame (ORF) the start codon was already determined.

To amplify the complete ORF a RAMP-RT-PCR was performed. Since it is known that the genomic RNA of astroviruses contain an poly-A tail at its 3' end an oligonucleotide was delineated which contained an poly T tail with an GC-clamp sequence (see Table 1, polyT-GC). The Ramp-RT-PCR was performed with a primer pair (DucPicoRP2Rev (SEQ ID NO:14), polyT-GC) and yielded a faint fragment of 1846 bp. The fragment was cloned and sequenced and a probable ORF was determined by the use of the previously determined nucleotide sequences (Astro-Frag1), as shown in FIG. 12. The location of the single RT-PCR fragments is depicted in FIG. 4.

A blast search using blastn (NCBI database) showed no similarities with any nucleotide sequence. Only a small portion of the sequence (34 nucleotides) showed a 96% identity with human astroviruses (e.g Human astrovirus type 8 T8/US/KL1553/1998 capsid protein precursor, GENBANK Accession Number AY304469). The similarities with amino acid sequences of turkey astrovirus 2 (TAV 2) (Genbank accession number AAV37186, similarity: 46.2%), TAV 3 (AAV37187, 38.5%), TAV (ABX46578, 37.5%), duck astrovirus (YP_002728003, 36.3%), avian nephritis virus 1 (BAA92849, 33.0%), avian nephritis virus 2 (BAB21617, 30.8%), human astrovirus (BAA33721, 29.8%), bat astrovirus (ACN88712, 29.0%), ovine astrovirus (NP_059946, 28.6%), mink astrovirus (NP_795336, 28.5%), feline astrovirus (AAC13556, 28.0%), and porcine astrovirus (CAB95000, 27.5%). This showed that this new astrovirus had a limited similarity to other astroviruses and seemed indeed a new member of the family Astroviridae. The low similarities to other chicken astroviruses were somewhat surprising, since avian nephritis virus 1 showed a similarity of 70% to avian nephritis virus 2. Also the similarities between turkey astroviruses were comparable high. The amino acid sequence of TAV showed a similarity to TAV 2 and TAV 3 of 85% and 81%, respectively.

Generation of a Recombinant Baculovirus Expressing the Astrovirus Capsid Protein.

Using the determined nucleotide sequence of 2951 nucleotide (nt), an open reading frame (ORF) of 2250 nucleotides (SEQ ID NO:1) was deduced which encoded a protein of 743 aa (amino acids 1-743 of SEQ ID NO:2). The ORF of the capsid protein was amplified by RT-PCR using two oligonucleotides, CapFP (SEQ ID NO:15) and CapRP (SEQ ID NO:16). CapRP also encoded a 6×His sequence to obtain a His-tag at the C-terminus of the capsid protein for subsequent purification procedures. The obtained RT-PCR fragment (FragAstroCap-ORF) using RNA prepared from purified gut content of RSS+/1 chicken was cloned and sequenced. The fragment was cleaved from the cloning vector pCR2.1 with EcoRI/NotI and ligated into the appropriately cleaved baculovirus transfer vector pFASTDUAL (Invitrogen). The resulting plasmid (pFAST-AstroBac) was used for the generation of a recombinant baculovirus using the Bac-to-Bac system (Invitrogen) as described by the manufacturer. The existence of a recombinant baculovirus was confirmed by PCR using the primer pair which was used for the amplification of the ORF from the RNA (CapFP, CapRP). This PCR fragment was cloned and the identity of the sequence was verified by sequencing. The recombinant virus (AstCap-Bac) was propagated in Sf9 cells and used for infection of Sf9 cells for protein purification with an MOI of 1. Three days after infection the protein was purified as previously published (Letzel et al., 2007, J Gen Virol; 88:2824-2833). The protein purification was monitored by SDS-PAGE followed by staining of the proteins and Western Blot (FIG. 5). The stained protein gel showed no prominent band in the lysate of infected cells. In the eluate, a single band with an approximate molecular weight of 80 kDa was observed. This molecular weight was in accordance with the theoretical molecular weight of 82.91 kDa. By Western blot analysis using a 6×His specific mAb, a band with a similar molecular weight was observed in the lysate before and after centrifugation and after elution of the protein from the Talon matrix. The identity of the protein was confirmed by MALDI-TOF MS/MS analysis using the single stained protein band after the purification process.

Generation of Tools for the Detection of Antigens and Antibodies.

In order to detect antibodies raised against the protein, three-week-old SPF birds were immunized with the purified protein. The chicken serum was used to establish an ELISA system. First a checker-board titration was performed to obtain the best ratio between the positive and negative chicken serum at a certain antigen dilution. The antigen was diluted 1:10 in binding buffer and the chicken serum was diluted 1:100 in dilution buffer prior adding to the plate. Using these parameters we used 100 sera from one-day-old SPF chickens and determined the cut off point as defined by the average of the adsorption plus three-times the standard deviation. The average adsorption was 0.064 with a standard deviation of 0.009 which resulted in a cut off of 0.091. The cut-off point used for the ELISA was set at 0.1.

Vaccination of Broiler Breeder and Challenge of the Progeny.

For the study, 30 broiler breeder hens and six broiler breeder rooster were obtained at 21 weeks of age. The animals were divided into two groups of 15 breeder hens and three roosters each. After one week of adaptation to the new facility, hens and rooster were bled to obtain a pre-immunserum. One group of hens was vaccinated with the experimental vaccine of Incomplete Freund's adjuvant and the recombinant protein. The roosters were not vaccinated and served as sentinel controls in each group. Development of the serum antibody titer was measured by an indirect ELISA using the recombinant antigen (FIG. 6). Two weeks after each immunization the birds were bled and the serum antibody level specific for this antigen was determined. At 21 weeks of age both groups showed a similar antibody titer, as measured by ELISA. In the non-vaccinated group the antibody titer declined over the duration of the experiment with the lowest titer at the time of the third bleed. Interestingly, a high standard deviation was observed which indicates that the antibody titers varied between the single hens. In contrast, in the group of hens vaccinated with the recombinant antigen the average antibody titer increased and reached a plateau 14 days after the second vaccination. Moreover, the standard deviation within this group was lower than in the non-vaccinated group. The non-vaccinated roosters were bled in parallel with the breeder hens. The ELISA data showed that the titer of the rooster's sera fluctuated over the tested time but stayed below the titer of the vaccinated group independent of whether or not the serum was taken from roosters in the non-vaccinated group or the vaccinated group.

Vaccination with the Recombinant Antigen Protects Against RSS.

Figure 7:
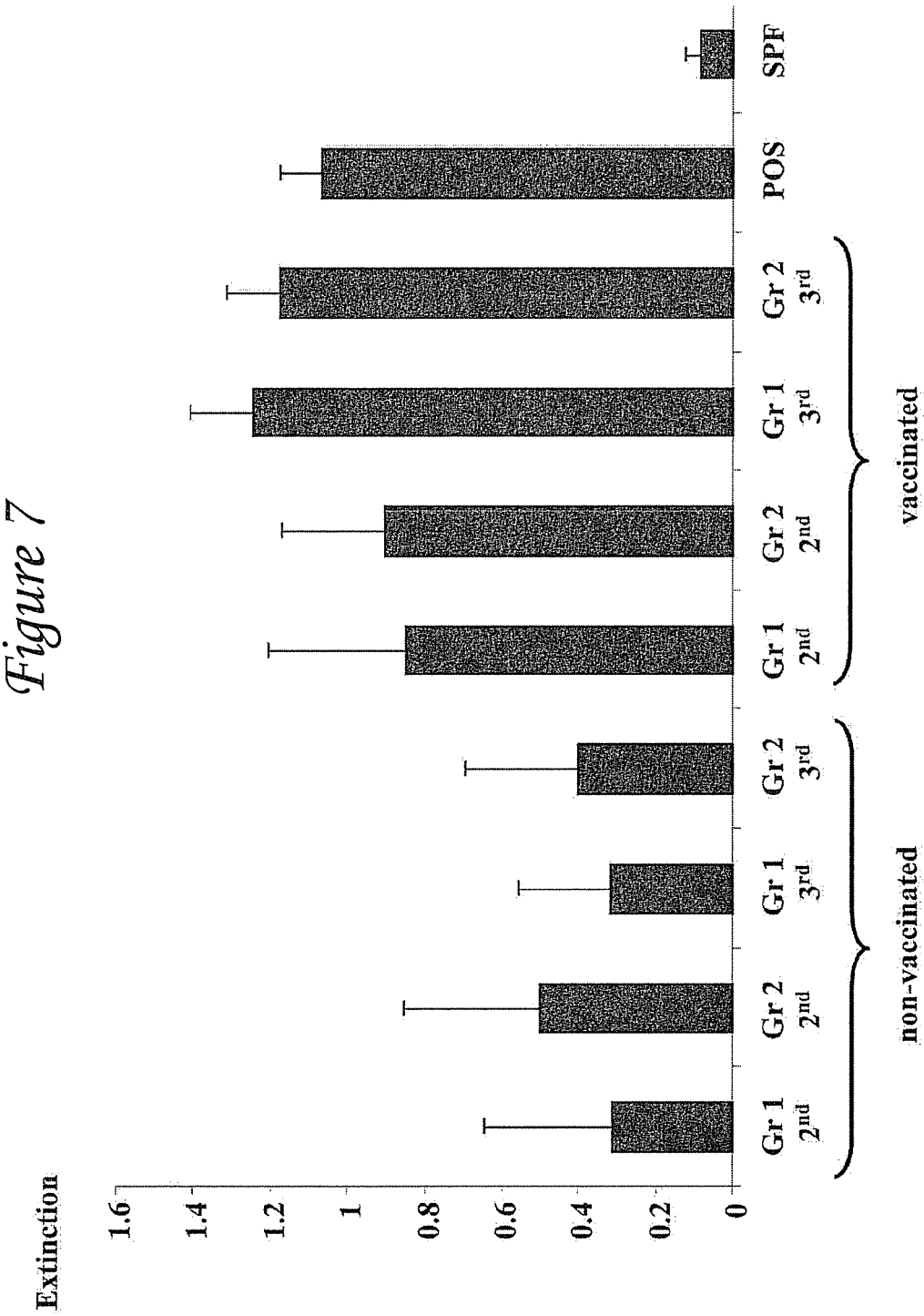
FIG. 7. Maternal derived antibodies raised against the astrovirus protein are transferred to the progeny of vaccinated hens. The progeny from vaccinated and non-vaccinated broiler hen groups were hatched two times (Gr 1, Gr 2) after each vaccination. The collection of eggs started 14 days after the 2nd and 3rd vaccination. Blood samples were taken at day of hatch and serum samples were investigated using the astrovirus capsid protein ELISA. Positive and negative (SPF) control serum was analyzed in parallel. The extinction at a wave length of 405 nm is shown at the left axis.

Chickens were hatched after the second and third vaccination and serum samples were obtained at day of hatch. The serum samples were analyzed in the ELISA (FIG. 7). The antibody titer of chickens in the non-vaccinated group did not increase but a certain level of antibodies raised against the recombinant capsid protein was present. This is not surprising since the non-vaccinated breeder hens also showed reactivity with this particular antigen. Is has to be mentioned that single chicken sera in this group showed an ELISA optical density (OD) of greater than 1, but most sera were below an OD of 0.5. In the group of progeny from the vaccinated breeder hens, the titer was higher after the second vaccination which is in agreement with the ELISA data obtained from the sera of the broiler breeder. The titer in broiler chickens elevated further after the third vaccination. ELISA titer in the broiler breeder group increased not significantly after the third vaccination probably because the immune response likely reached a plateau against this particular antigen. Furthermore it was observed that the standard deviation in the offspring of the non-vaccinated group was very high but was comparably low in the vaccinated group indicating a more uniform antibody titer in the latter group.

Figure 8:
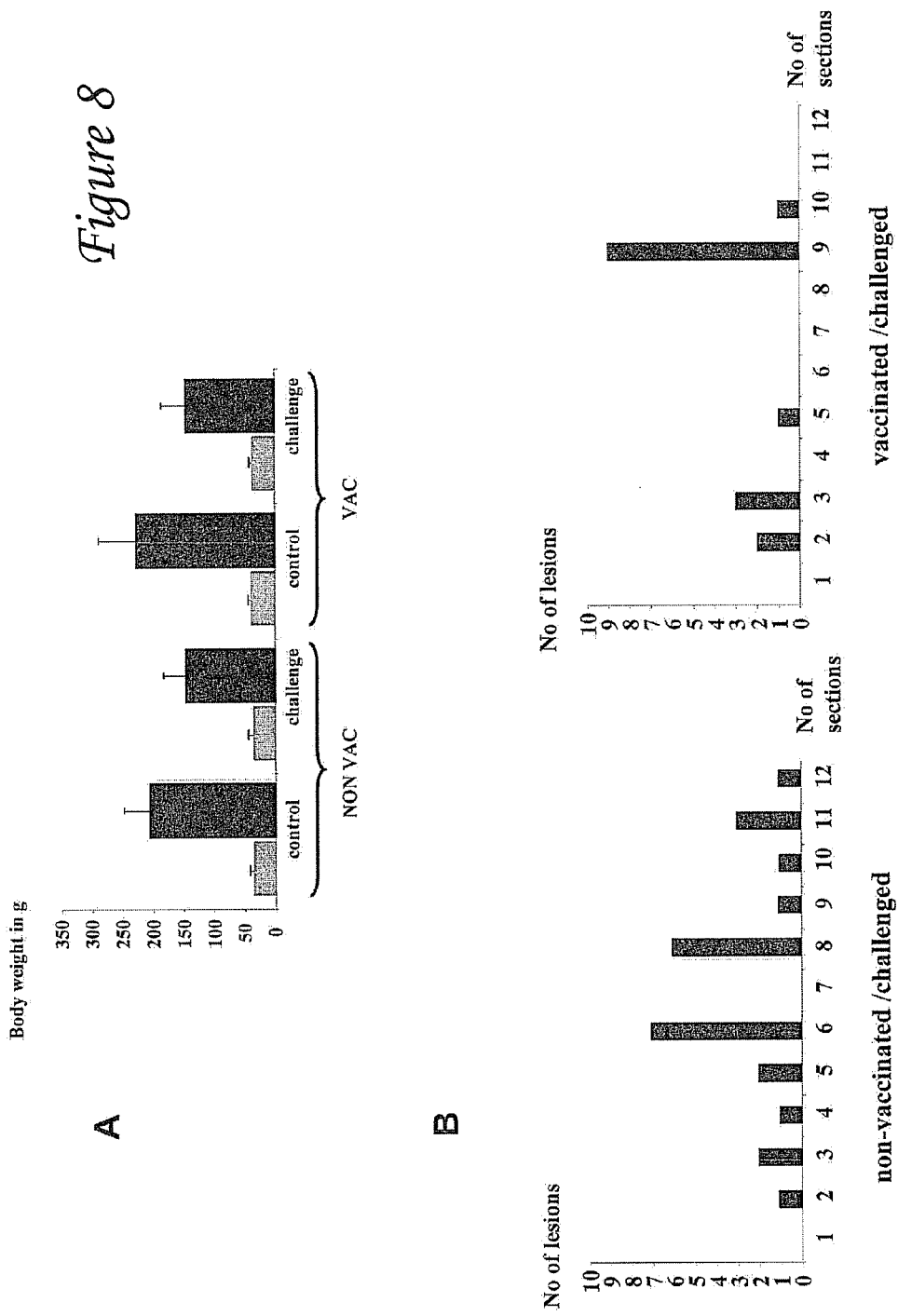
FIGS. 8A-8B. Two vaccinations with the recombinant astrovirus capsid protein decreases enteropathic lesions in the gut of the offspring.
Figure 9:
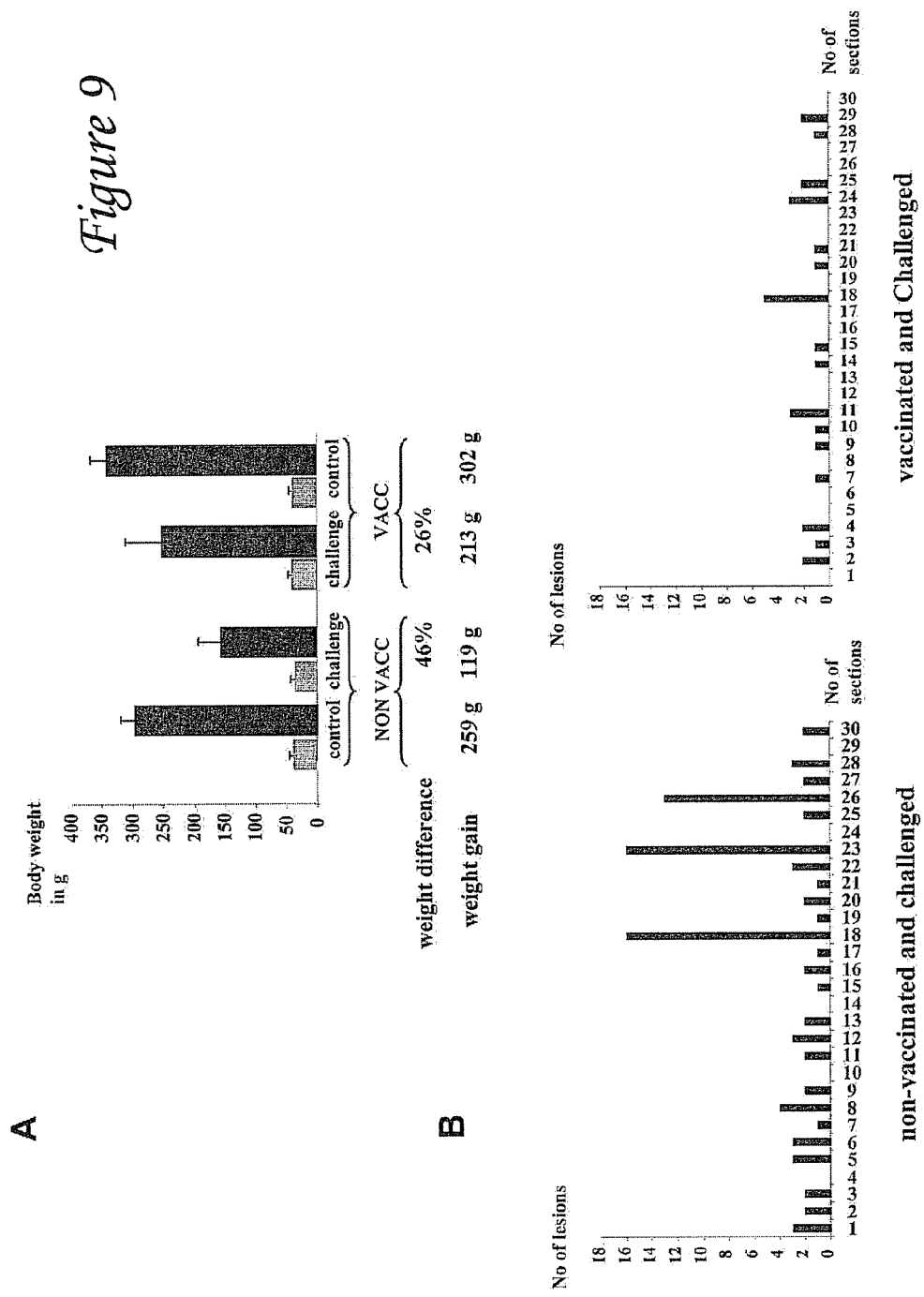
FIGS. 9A-9B. Three vaccinations with the recombinant astrovirus capsid protein decreases enteropathic lesions in the gut and mitigates weight depression in the offspring.

To test if this antibody response was sufficient to protect from RSS challenge, experiments were performed using 15 chickens hatched from eggs collected beginning at 14 days following the vaccination time point. The offspring from both groups were randomly divided into two groups each and weighed individually before infection by gavage. The chickens were either gavaged with filtered gut content or mock-infected with PBS. The results of the experiments demonstrated that two vaccinations were not sufficient to prevent the differences in weight 12 days after infection (FIG. 8A). Both challenge groups showed macroscopic as well as microscopic lesions. Microscopic lesions were present in fewer gut sections in the vaccinated group in comparison to the off spring of the non-vaccinated group (FIG. 8B). The first infection experiment using the one-day-old progeny after the third vaccination indicated that presence of maternal derived antibodies were able to reduce the difference in weight between the non-inoculated control birds and the challenged birds (FIG. 9A). During the experiment the chickens of the non-vaccinated/challenged group showed slight diarrhea and lassitude. In the chickens of the other three groups no signs of disease were observed. In addition, only the chickens in the non-vaccinated/challenged group showed macroscopic lesions of RSS. The weight difference between non-challenged control birds and their challenged hatch mates was 26% in the vaccinated group whereas a difference of 46% was observed between the non-challenged and challenged chicken of the non-vaccinated group.

Figure 10:
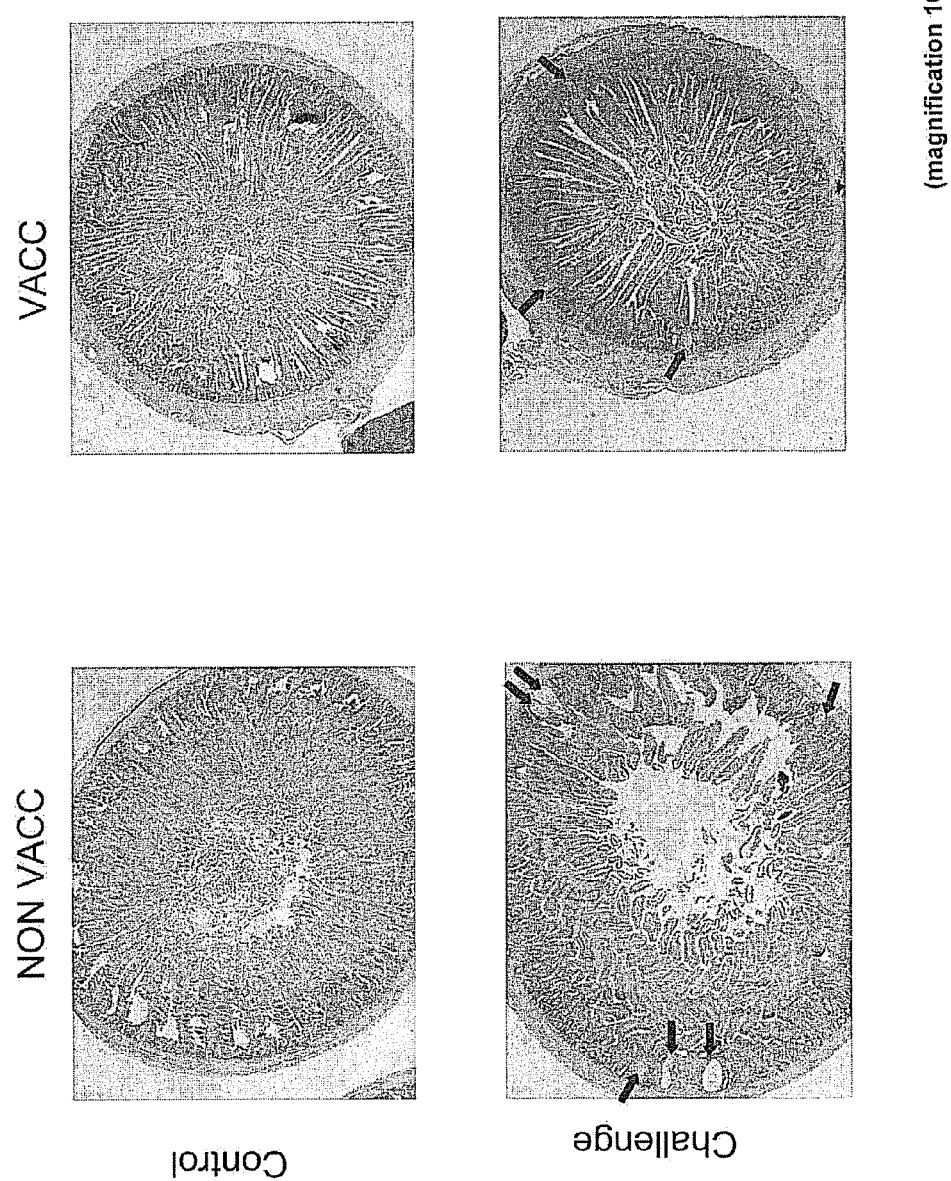
FIG. 10. Representative enteropathic lesions of cross section of the duodenal loop of experimentally RSS affected chicken. Haematoxylin and eosin stained section of the duodenal loop of progeny of vaccinated (VACC) and non-vaccinated (NON-VACC) which has been RSS challenged (challenge) or not-challenged (control) are shown. The chickens were euthanized at day 12 after challenge. The presence of enteropathic cysts are indicated by an arrow (magnification 16×).
Figure 11:
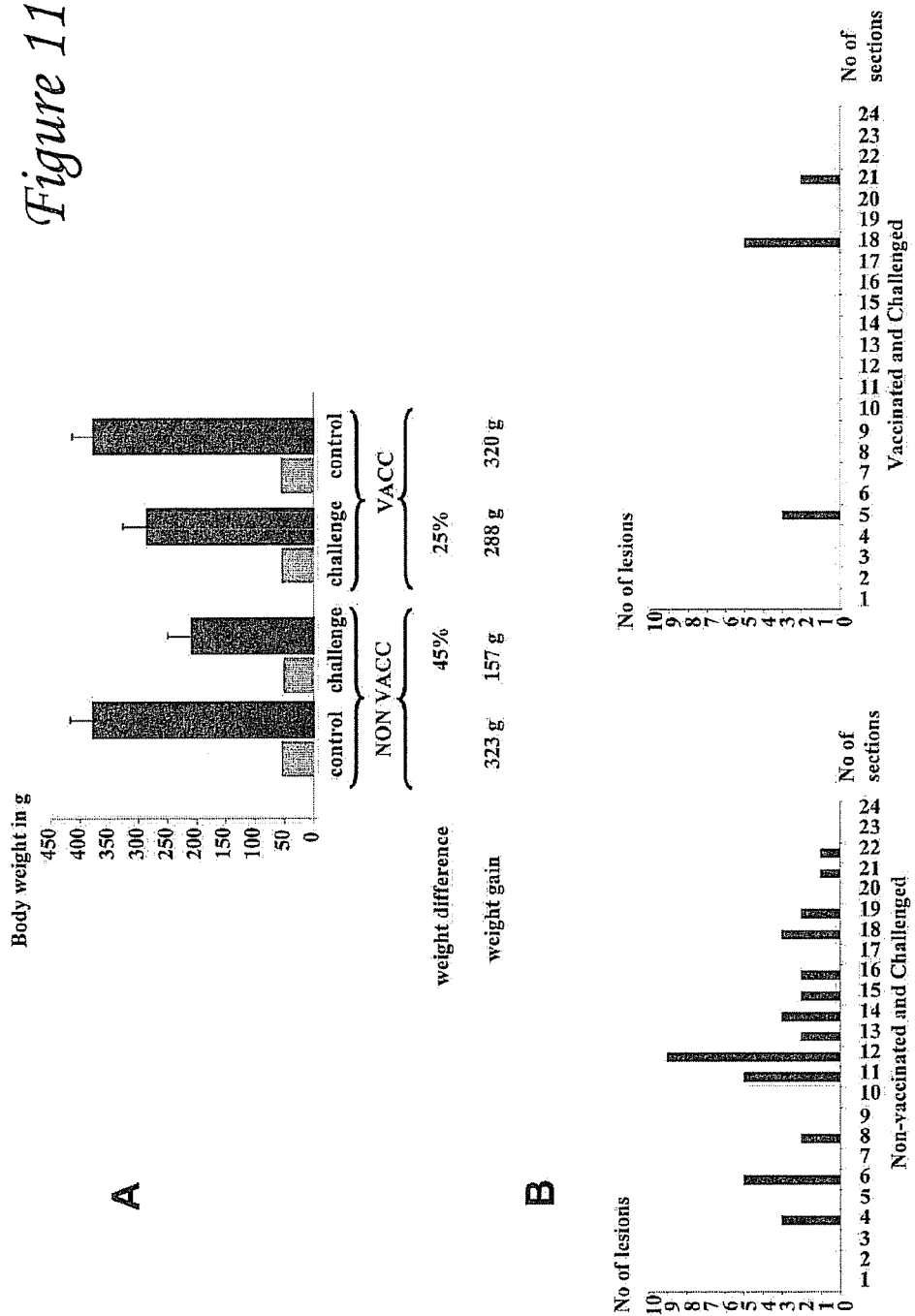
FIGS. 11A-11B. Three vaccinations with the recombinant astrovirus capsid protein decreases enteropathic lesions in the gut and mitigates weight depression in the offspring.
Figure 13:
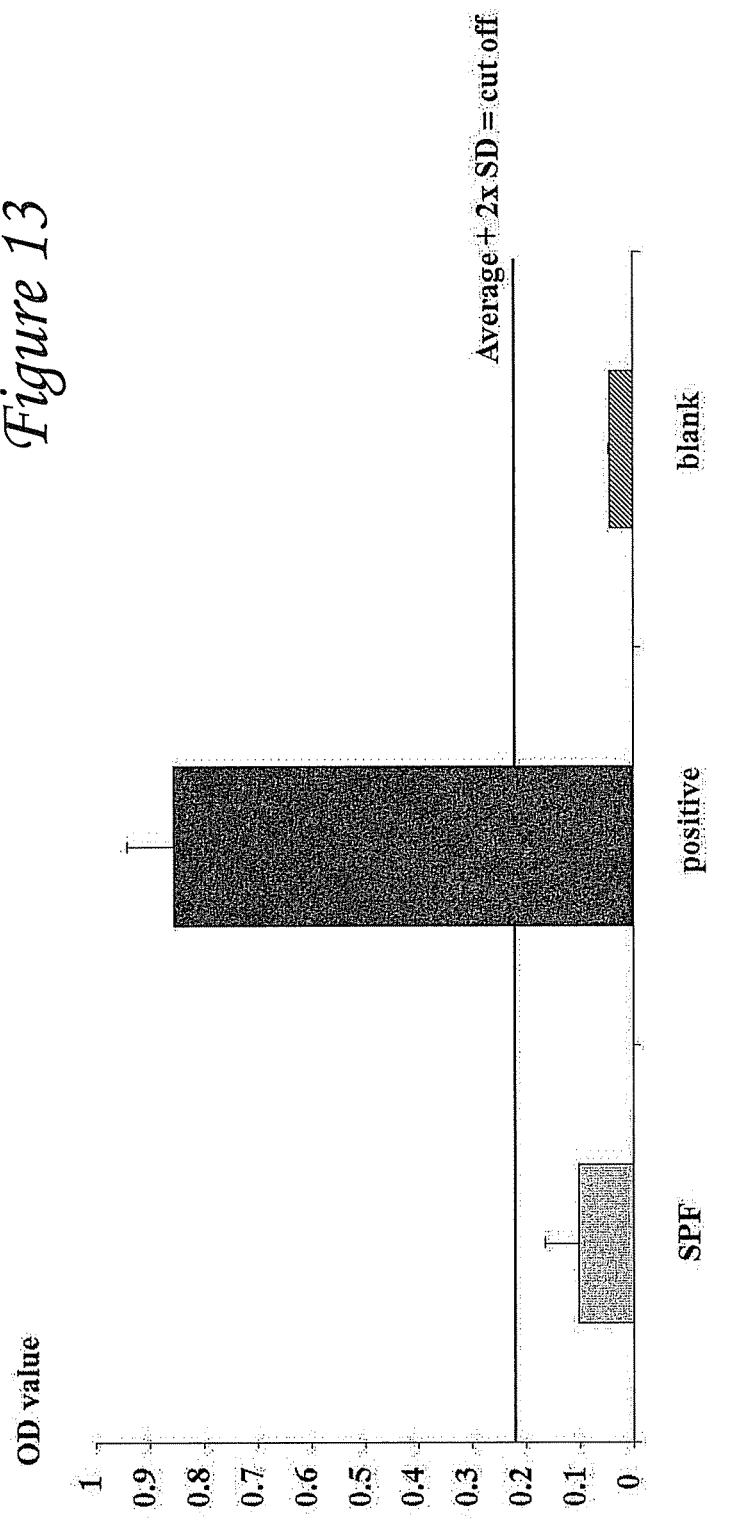
FIG. 13. Determination of the cut off value for the astrovirus antigen ELISA. Sera from eighty SPF chickens (SPF) and five SPF chickens vaccinated with the recombinant antigen (positive) were used in a dilution of 1:100 in the indirect ELISA. No serum was used for measuring the reaction for the conjugate with the antigen. For the determination of the cut off value the double standard deviation was added to the average of the OD value.
Figure 14A:
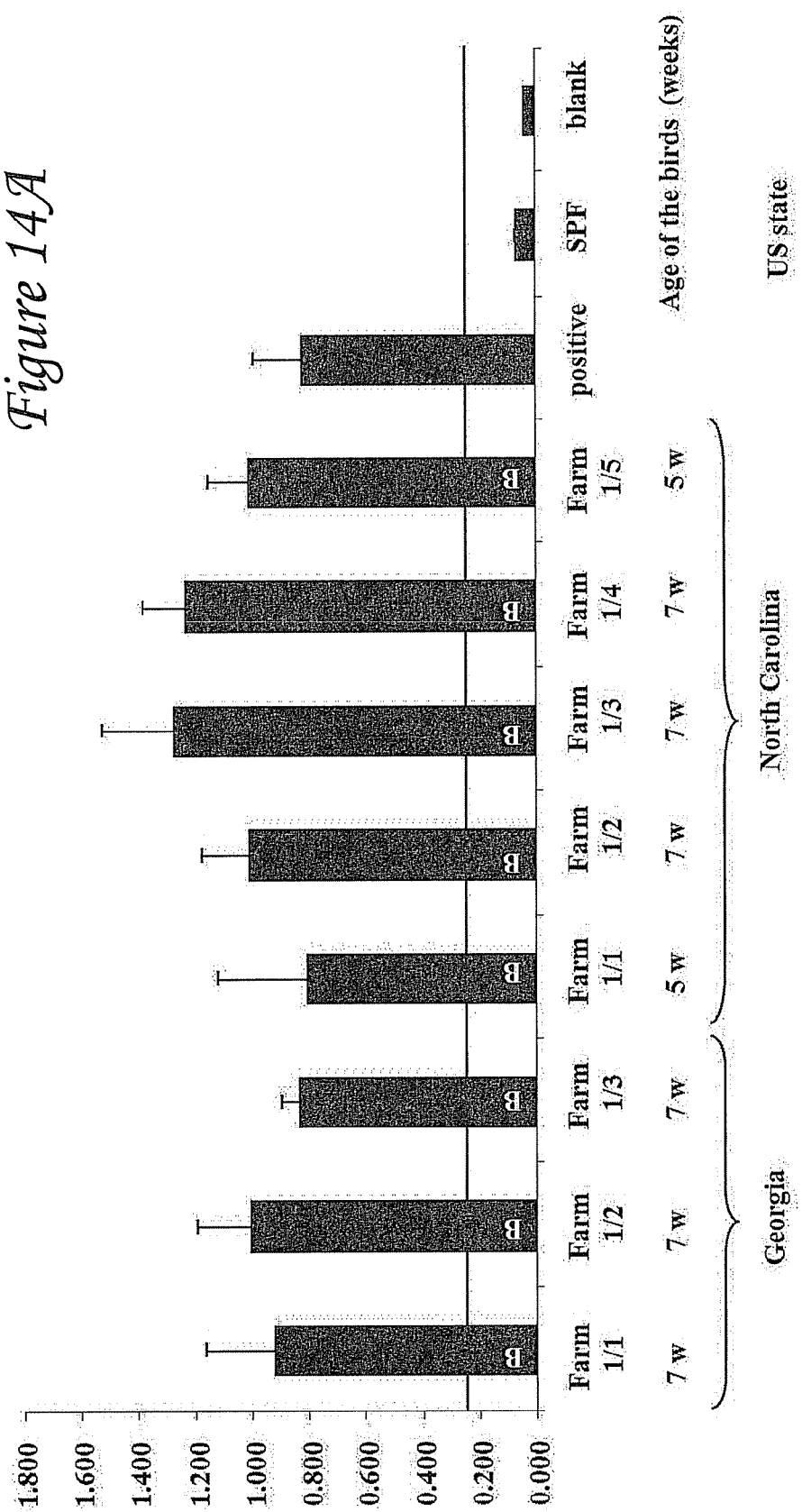
Figure 14B:
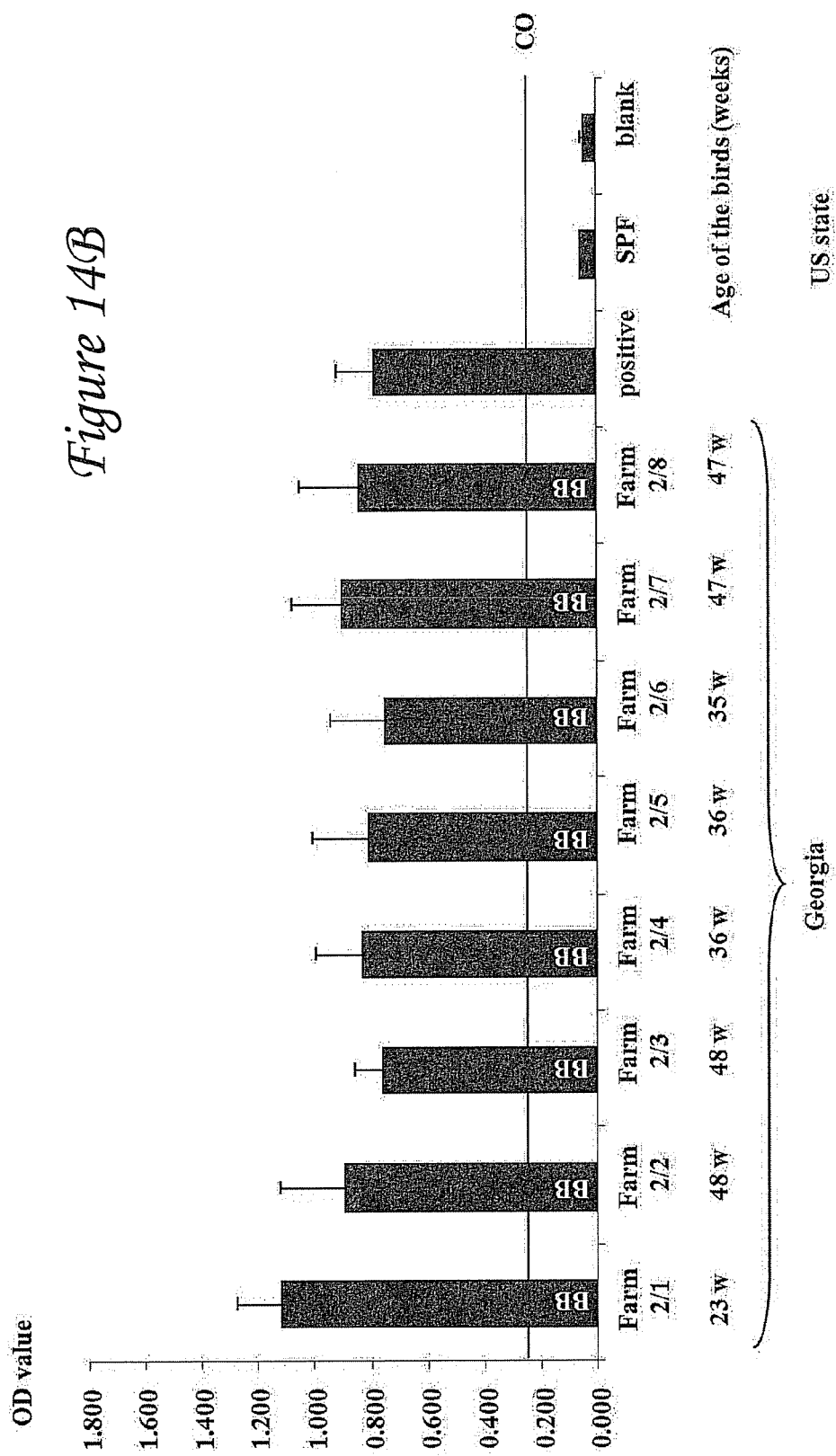
Figure 14C:
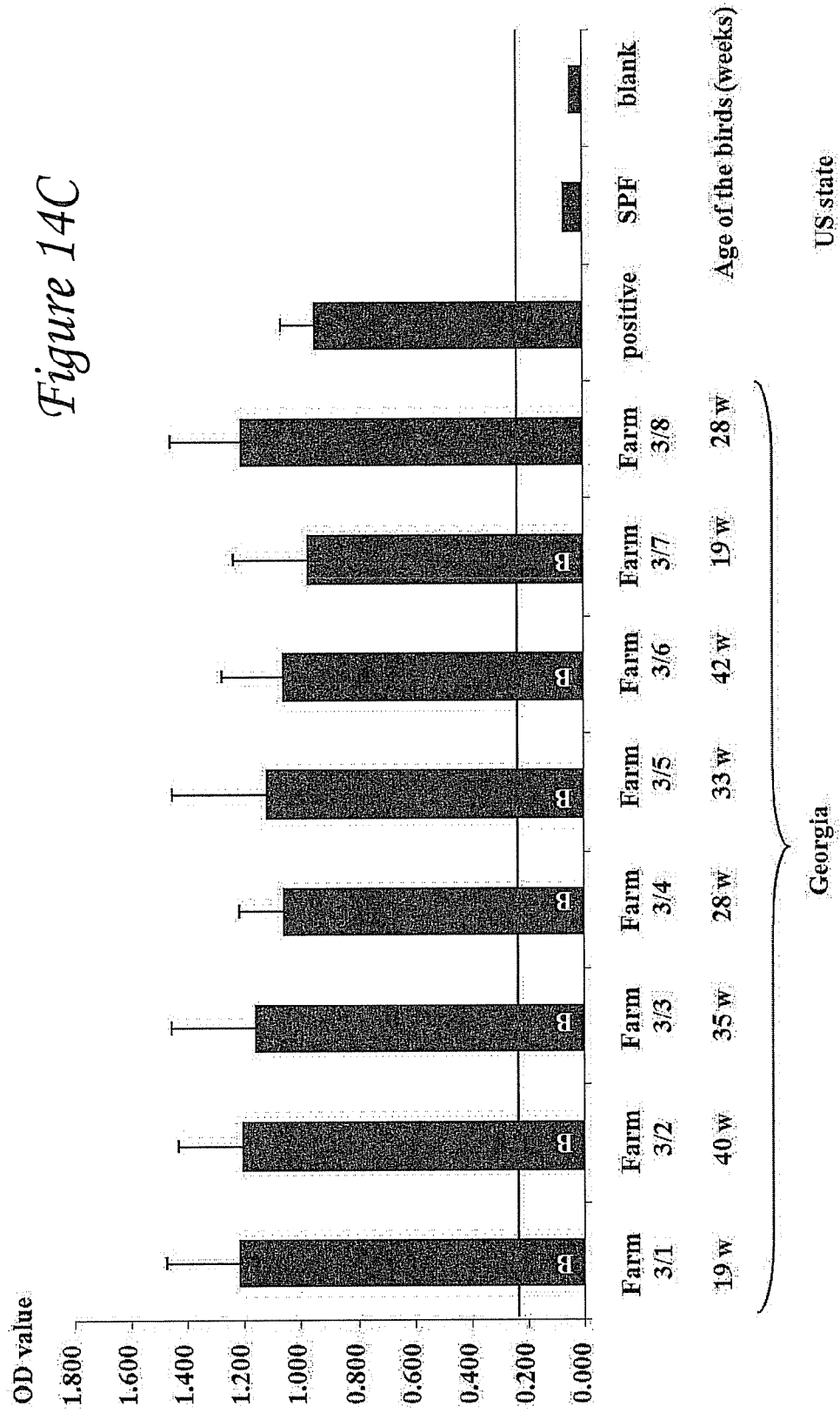
Figure 14E:
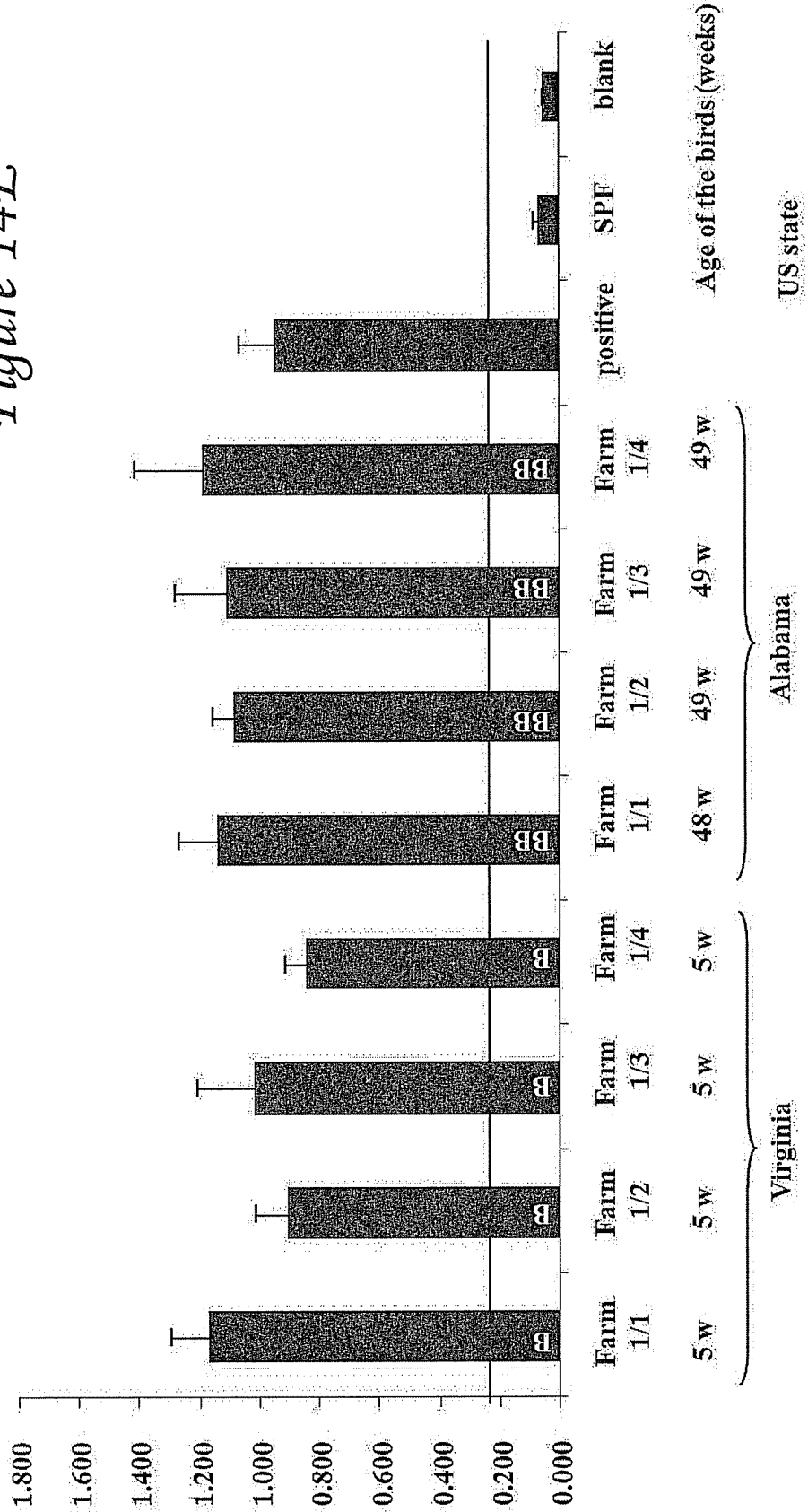
Figure 14F:
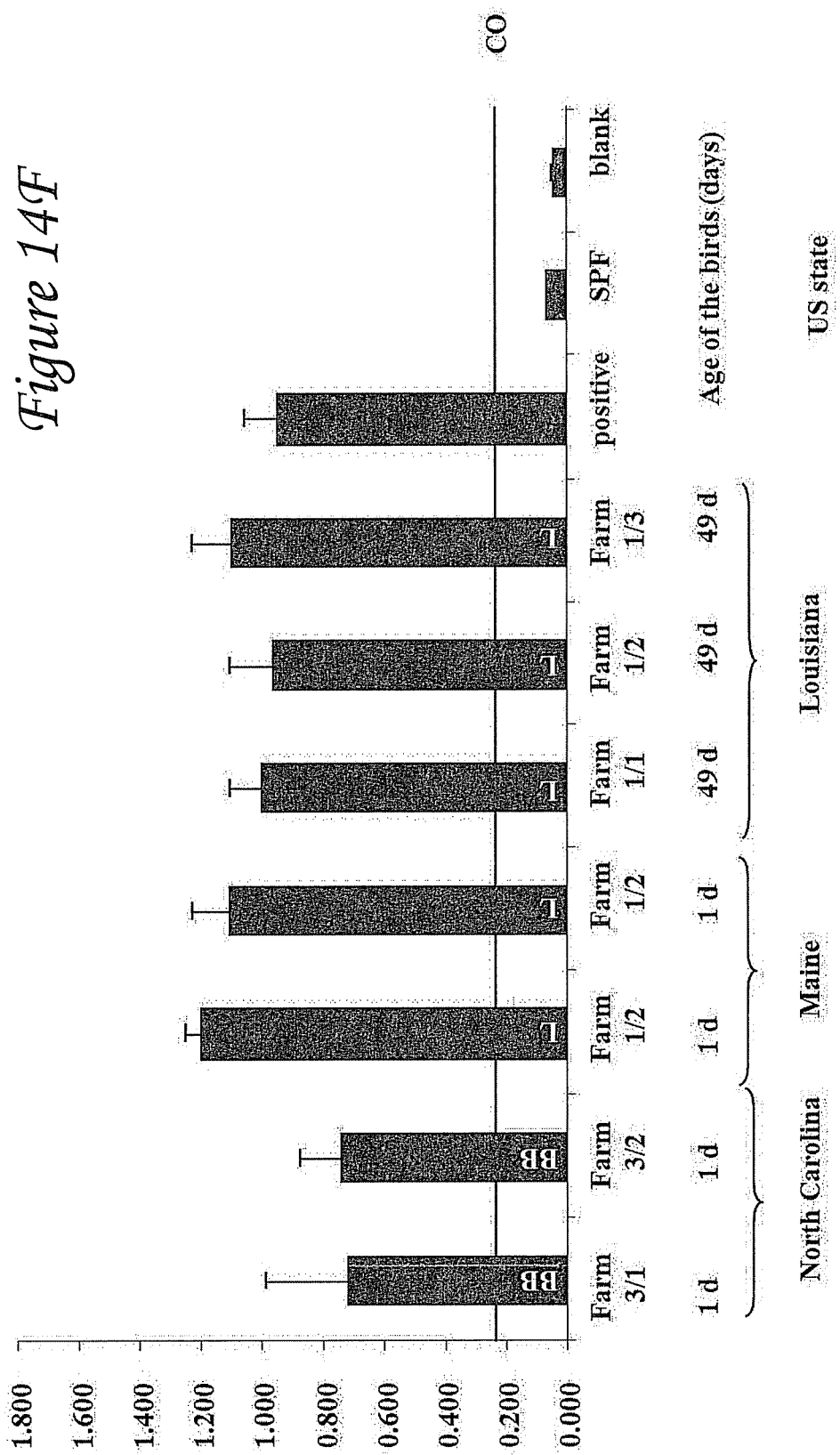
Figure 14G:
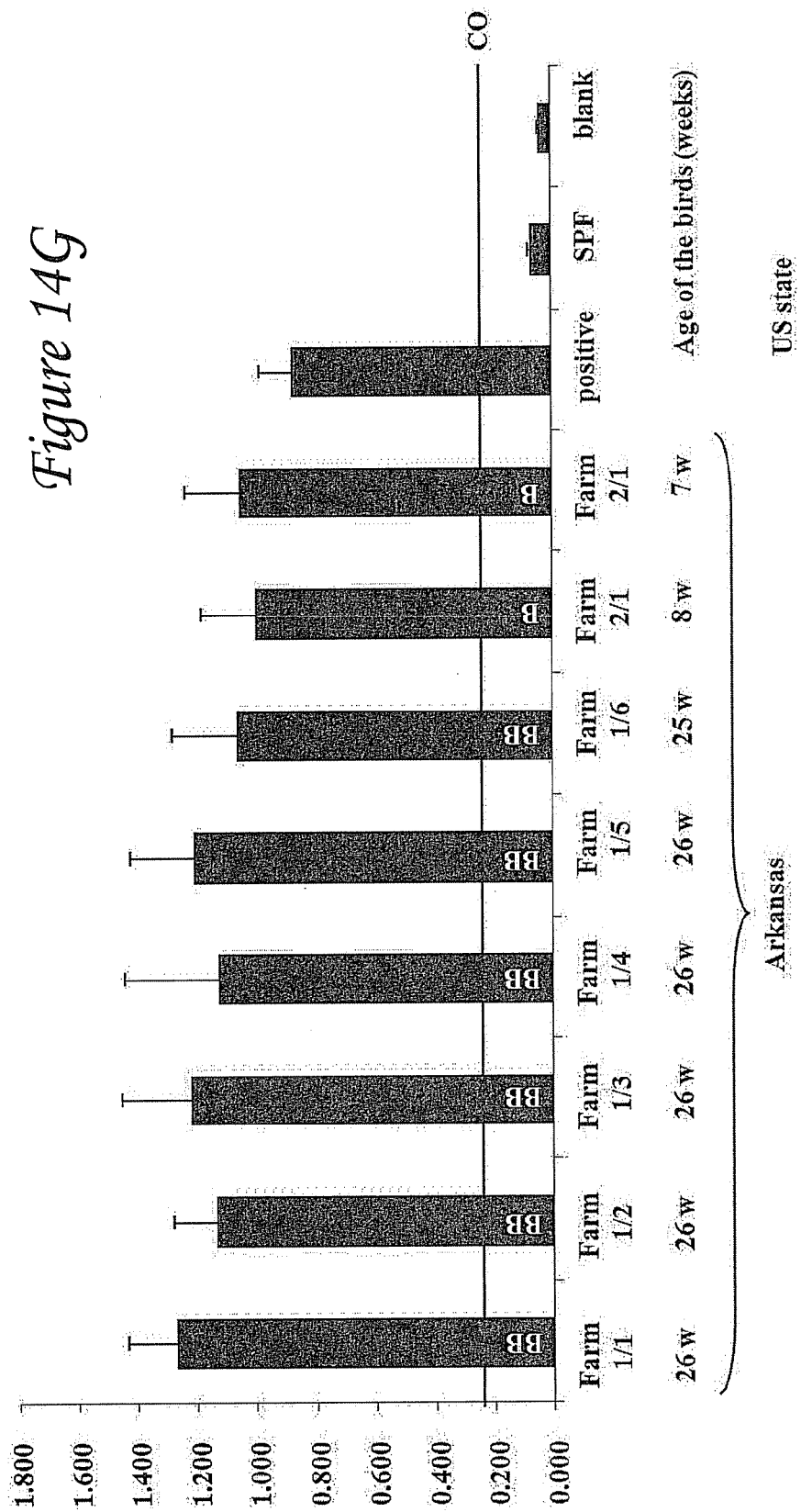
Figure 14I:
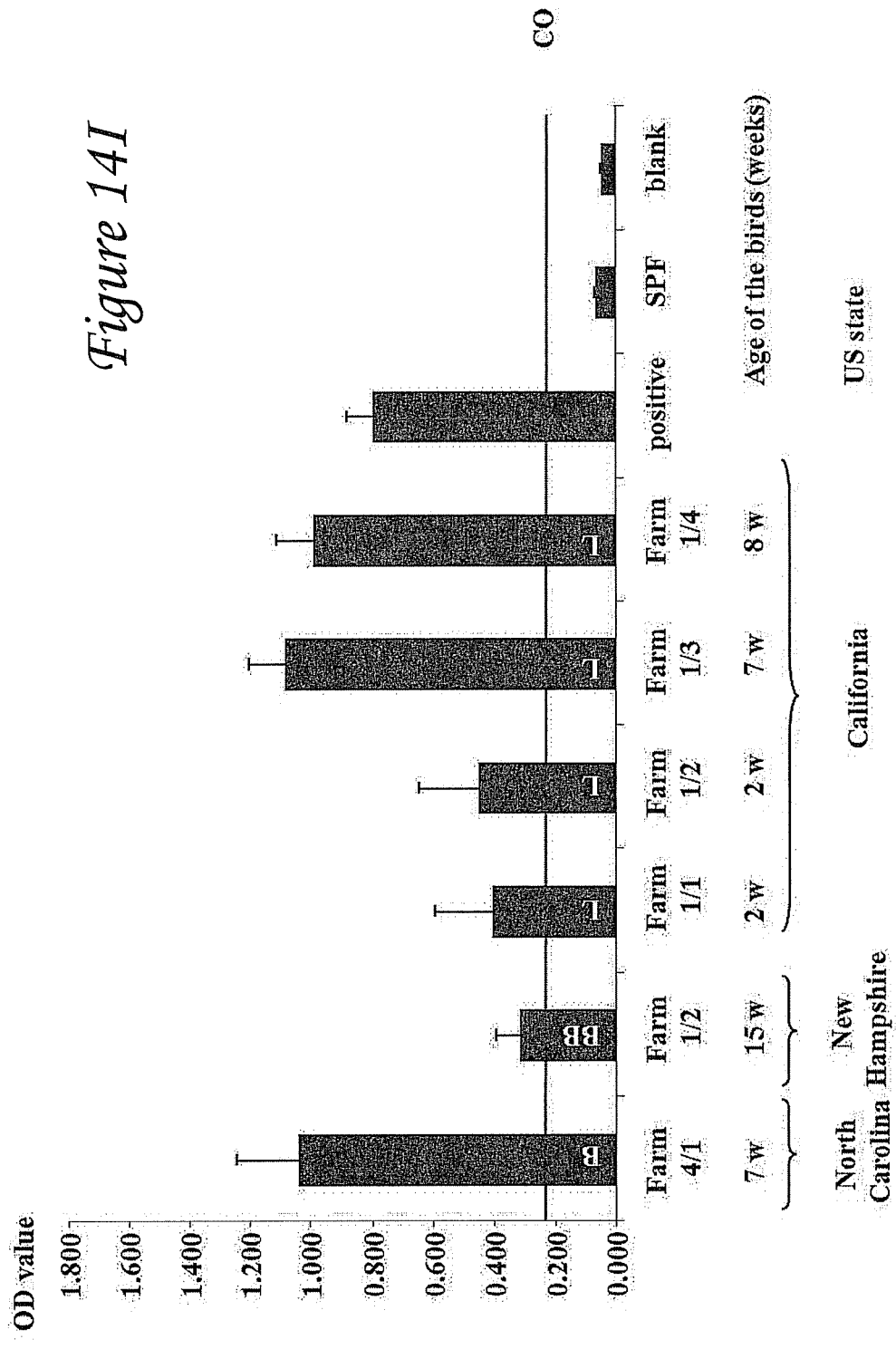

To obtain a more objective picture we calculated the average weight gain. To this end we calculated for each group the average weight at day one and day 12 and subtracted the average weight of day one from the average weight of day 12. The chickens of the vaccinated/challenged group gained on average 94 g more weight during the 12 days period of the experiment in comparison to the progeny of the challenged/non-vaccinated group. Histological examination of the duodenal loop indicated that vaccination of breeder hens with the recombinant protein mitigated the number of affected guts as well as the severity of the lesions (FIG. 9B). In both non-challenged control groups no lesions in the gut typical of RSS were found. In addition, the average size of the lesions was smaller in the vaccinated/challenged group (FIG. 10) in comparison to the challenged/non-vaccinated group. To confirm the results a second experiment was performed using the same parameter as in the previous experiment. The average weight difference between challenged and the non-challenged group was 45% of the progeny from the non-vaccinated breeder hens (FIG. 11A). Again, the progeny of the vaccinated group which was challenged showed only 25% weight difference to the non-challenged hatch mates. The calculation of the weight gain showed clearly that vaccinated broiler chickens gained 83% more weight (288 grams (g)) than the non-vaccinated broiler chickens (157 g). The evaluation of the histological lesions showed that only three sections out of 24 sections showed cystic enteropathy to a low degree in the group of vaccinated and challenged chicken. In contrast, in the duodenal loop of the non-vaccinated/challenged chickens more (13/24) and to a higher degree cystic lesions in the gut were observed (FIG. 11B).

Discussion

RSS in chickens is an important problem in the poultry industry especially in the broiler production. To date, the etiological agent has not been described, likely due to the fact that the agent, or several agents, can not be isolated in cultural systems such as cell culture or embryonated eggs. To develop and subsequently test a vaccine candidate an appropriate challenge model needs to be in place. Since no agent was isolated initially an approach was applied which resembled possible field condition. The approach using non treated and/or filtered gut content to reproduce the disease has been described before (Nili et al., 2007, *Comp Clin Pathol;* 16:161-6; Montgomery et al., 1997, *Avian Dis;* 41:80-92; and Songserm et al., 2000, *Avian Dis;* 44:556-67). The experimental animal model system used in this example resulted in typical signs for RSS such as growth retardation, and cystic lesions in the gut as observed during necropsy and by histopathology. The results obtained during the experiments using gut content of non-clinical diseased chickens versus the gut content of clinical diseased chickens indicate that an infectious agent induced the weight depression. With the present example, a 0.22 μm filtrate induced a significant reduction in weight and the presence of gut lesions, indicating a viral etiology. But it needed to be mentioned that the body weight in the group inoculated with the unfiltered gut content also showed a difference in weight in comparison to the group inoculated with the filtrate. These results are in agreement with Nili et al. ((Nili et al., 2007, *Comp Clin Pathol;* 16:161-6) and suggest that the presence of infectious agents other than viruses might also play a role in the severity of the disease. The presence of both, gut lesions and reduction in body weight, after treatment of the filtrate with chloroform supported the hypothesis that the agent(s) responsible for RSS are non-enveloped viruses.

Based on the description that a small round virus might play an important role in the genesis of RSS, with this example, the genomic sequence of a picornavirus was amplified. The use of a combination of degenerated primers and primers containing sequences of conserved regions based on nucleotide sequences of picornaviral RdRP resulted in the discovery of a sequence of a new, undescribed astrovirus. The closest relative amino acid sequence was a turkey astrovirus 2 sequence whereas the nucleotide sequence showed no similarities to any sequences present in the NCBI database.

Several attempts in primary chicken liver cells and primary chicken kidney cells failed to isolate a virus which reacted with the anti-capsid protein serum from chickens (ck-Cap+) in immunofluorescence. Thus, the baculovirus-vector approach was chosen to develop a vaccine. The expression of viral proteins using recombinant baculoviruses for the use in vaccines has been shown for several viral antigens, e.g. human paramyxovirus 3 (van Wyke Coelingh et al., 1987, *Virology*; 160:465-72), dengue virus (Zhang et al., 1988, *J Virol*; 62:3027-31), West Nile virus (Bonafé et al., 2009, *Vaccine*; 27:213-22), and influenza A virus (Mahmood et al., 2008, *Vaccine*; 26:5393-9). The presented example showed clearly that the purified protein induces an immune response in broiler breeders. In addition, field sera obtained from 20 breeder flocks (layers and broiler, 10 sera per flock) from different states in the 625 USA (GA, DE, AL) were investigated for the presence of antibodies against the recombinant protein using the indirect ELISA. The results also indicated that this virus or an antigenic related virus was present in the field.

Due to the prime/boost scheme the level of antibodies were elevated in the vaccinated birds whereas the level of antibodies declined in the non vaccinated group. After the third vaccination the antibody level in the breeder hens was further elevated but with a lower standard deviation. A similar behavior of the antibody levels was observed in the appropriate serum samples of the progeny. This might explain the results after the challenge experiments. Infected chickens obtained after the second vaccination of the breeder hens showed no difference in weight gain to their nonvaccinated/challenged control chickens. The only observed difference was that a lower number of chickens of the vaccinated hens showed gut lesions in comparison to the chickens of the nonvaccinated controls. These results can be interpreted that the antibody level was not sufficient to provide protection from retarded growth of the chickens. After the third vaccination the challenged offspring showed a further elevated antibody titer and both, the presence of gut lesions and the differences in result was confirmed by a second experiment performed 14 day later. These results showed that a certain level of antibodies needs to be present to induce a partial protection against the differences in weight gain and gut lesions. Cystic lesions in the intestine are an important characteristic of the disease, since the cystic lesions in the small intestine were always present in the infected group but not in the controls. In conclusion the recombinant astrovirus capsid protein provided partial protection to the offspring of breeder hens three times vaccinated with a recombinant astrovirus capsid protein. This is the first report for a vaccine candidate able to induce partial protection against RSS in chickens.

The results of this example can now also be found in Sellers et al., *Vaccine*, 2010 Feb. 3; 28(5):1253-63. Epub 2009 Nov. 24.

Example 2

Preparation of Vaccine Under Industrial Conditions

Antigen and Vaccine Preparation.

Sf9 cells were infected in suspension culture with a multiplicity of infection of 1 with the recombinant astrovirus capsid protein encoding baculovirus. Three days after infection the cell will be harvested and centrifuged at 2000×g for 20 minutes at 4° C. The supernatant will be discarded and the cells will be incubated with lysis buffer as described by Letzel et al. (Letzel et al., 2007, J Gen Virol; 88:2824-2833). The supernatant was obtained after centrifugation (17000×g for 45 minutes at 4° C.) and was processed by continuous diafiltration on a Quixstand concentrating unit in a horizontal flow hood using and 30,000 MWCO hollow fiber membrane. The filtration was performed with six liters of PBS. Next the recombinant baculovirus was inactivated applying a treatment with beta-Propiolactone (Sigma) for 72 hours at 4° C. at a final concentration of 0.1%. The obtained inactivated lysate was tested for the presence of infectious virus, as described below. To obtain a sufficient antigenic mass for vaccination the proteins in the lysate were 11.7-fold concentrated with Amicon Ultra-15 Centrifugal Filter Units-30 k (Millipore). The lysate was used to formulate water-in-oil emulsion vaccine using an adjuvant provided by Merial. Using this approach 300 ml of an experimental vaccine was produced.

Testing for Inactivation of the Recombinant Virus.

The initial sample before any treatment (S0) and the final inactivated sample before vaccine formulation (SF) were tested for the presence and the titer of infectious virus using a 10-fold titration in Sf 9 cells. The cells were incubated for 7 days at 28° C. The samples were subsequently passaged five times. Each passage was analyzed for the presence of infectious virus by transfer of 100 ul of cell culture supernatant to 100 ul fresh diluted Sf9 cells ($10^5$/ml). The cells were incubated for three days. The cells were fixed with ice-cold (−20° C.) ethanol for 10 minutes. The fixed cells were tested for the presence of infectious baculovirus by using an anti-baculovirus specific monoclonal antibody (Mouse Anti-AcV5 Monoclonal Antibody, Clone ACV5 antibody; Sigma Aldrich) and a goat anti-mouse FITC-conjugate (Jackson ImmunoResearch).

Example 3

Vaccine Application Under Semi-Field Conditions

With this example commercial broiler breeders will be vaccinated with a vaccine prepared as in Example 2 above under industrial conditions to determine if sufficient maternal derived antibodies are induced to provide protection to the offspring under challenge conditions similar to the condition which are prevalent in the field.

Vaccination of Breeder Hens.

Six week old commercial broiler breeder hens (BH) and rooster will be housed in floor pens. At seven weeks of age the birds will be bled by puncture of the brachial vein to obtain serum samples. The serum samples will be analyzed for the presence of antibodies which are specific for the recombinant astrovirus capsid protein by an indirect ELISA. At eleven weeks of age the broiler breeder hens will be subcutaneously vaccinated in the neck using one ml of the experimental vaccine (BH-Vac). One group of breeder hens and the rooster will serve as non-vaccinated control (BH-Con). Four weeks after vaccination serum samples will be obtained as described above. The next subcutaneous vaccination will be performed at an age of 18 weeks (booster vaccination). Four weeks, and every subsequent four weeks after booster vaccination serum samples will be obtained as described above and analyzed for the presence of antibodies which are specific for the recombinant astrovirus capsid protein by an indirect ELISA. This will result in data regarding the dynamic level of antibodies in the breeders over time. Starting with 24 weeks the eggs will be collected and stored at 4° C. until use. The eggs will be incubated to hatch the offspring of the vaccinated broiler hens and the offspring of the appropriate non-vaccinated controls.

The offspring will be challenged in a colony house-floor challenge model. Serum samples from one-day-old broiler chicken from the offspring of BH-Vac and BH-Con will be monitored for the presence of antibodies raised against the recombinant protein.

Colony House Floor Challenge Model.

Chicken litter will be collected and transported from a farm with clinical signs of RSS to experimental isolation houses (colony houses, CH). The chicken litter will distributed onto the floor of a colony house with an approximate area of 10 m² (CH-RSS+). In parallel, fresh wood shavings will distributed onto the floor of another colony house (negative control, CH-RSS-neg). In each house, 150 one-day-old broiler chickens from a commercial hatchery will be raised. Water and feed will be provided ad libitum. Twelve days after placing the birds in the colony houses, the birds will be removed and humanely euthanized with $CO_2$. The body weights of all birds will be recorded. Once the difference in weight gain between the RSS+ and RSS control group reached 40% to 50% the hatched offspring of the BH-Vac and BH-Con will be placed either on litter of the CH-RSS+ or on fresh wood shavings of CH-RSS-neg. Twelve days after placing the birds in the colony houses, the birds will be removed and humanely euthanized with $CO_2$. The body weights of all birds will be recorded and necropsy will be performed, the small intestine removed, tissue samples from the duodenal loop harvested and fixed in neutral buffered formalin for subsequent histological examination.

Example 4

Field Study

This example will determine if the vaccine prepared under industrial conditions induces sufficient maternal derived antibodies in vaccinated commercial broiler breeders to provide protection to the offspring under field conditions.

Antigen and Vaccine Preparation.

Vaccine will be prepared as described in Example 2. The production of this vaccine will result in a batch of approximately 80,000 vaccine doses for a field experiment. Testing for inactivation of the recombinant virus will be as described in Example 2.

Vaccination of Breeder Hens Under Field Conditions with an Experimental Vaccine.

Breeder hens of one house (approximately 39,000 breeder hens) of one company will be subcutaneously vaccinated with the experimental vaccine at 11 weeks and 18 weeks of age under production conditions. The remaining breeder hens of the same complex will serve as control. Serum samples from both groups (20 per flock) will be collected before vaccination, four weeks after each vaccination and every four weeks after the last vaccination. The eggs of the vaccinated hens will be separately hatched and placed in separate broiler production houses on a farm with a history of RSS. The performance of the broiler offspring of the vaccinated hens will be compared with the performance of the broiler offspring of the non-vaccinated hens in the other houses based on weight gain, feed conversion rate, mortality, and condemnation rate at the processing plant. Serum samples from one-day-old broiler chicken resulting from the offspring of vaccinated and non-vaccinated broiler breeder hens will be monitored for the presence of antibodies raised against the recombinant protein.

Example 5

Indirect ELISA

Validation of the indirect ELISA. ELISA as performed as described in Example 1. To further validate the ELISA, sera from eighty one-day-old specific pathogens free (SPF) chickens (Sunrise Farms, Catskill, N.Y.) were taken. To this end 100 SPF chickens eggs (Sunrise Farms, Catskill, N.Y.) were incubated until hatch at the Poultry Diagnostic and Research Center (PDRC, University of Georgia, Athens, Ga., USA). The eighty hatched one-day-old chickens were exsanguinated and the serum was obtained. Serum samples were incubated at 56° C. for 30 min prior use. As positive control chicken sera obtained from SPF chicken (Sunrise Farms, Catskill, N.Y.) vaccinated with the recombinant protein (example 1, page 29) were used. The serum samples were used in a dilution of 1:100 in the indirect ELISA using the purified capsid protein of the new chicken astrovirus as antigen bound on the plate. The results of the ELISA showed that the SPF sera resulted in an average OD value of 0.102 with a standard deviation of 0.059 (FIG. 13). The use of the chicken sera which have been generated against the purified recombinant chicken astrovirus capsid protein resulted in an average OD value of 0.855 with a standard deviation of 0.085. The cut off value was determined with average OD value of the SPF serum and the double value of the standard deviation was added which resulted in a value of 0.22.

Analysis of presence of antibodies in field sera directed against the capsid protein of the new chicken astrovirus. Next, serum samples were analyzed in the indirect ELISA which has been submitted to the PDRC for serological investigation of a variety of other avian diseases. Per flock, eight serum samples were included in the investigation. The average of the OD values and the appropriate standard deviation are shown (FIGS. 14A-14I). The serum samples were from chicken flocks from a number of eleven different US states (Georgia, North Carolina, South Carolina, Alabama, Arkansas, Louisiana, Virginia, Maine, Indiana, New Hampshire, California). The age of the birds varied from one-day-old chickens up to 49 weeks. Serum samples from broiler breeders, broiler, and layer were included in this study. The names of the appropriate farms were coded to protect their identity. The data show clearly that antibodies are present already one day after hatch (FIG. 14F) irrespective whether these birds were either layer type or meat type chicken (broiler). Furthermore it was observed that the virus is widespread in the US since investigated serum samples from each state showed an OD value clearly above the ELISA cut off. No correlation between age and level of the OD value was observed which indicates that the virus is constantly present in the chickens flock. The variation between plates is rather low since the OD values for both, the positive and negative sera were comparable between the plates.

Example 6

Development of Diagnostic Assay for the Detection of Viral RNA

Materials and Methods

To investigate whether viral RNA specific for the new chickens astrovirus is present in samples submitted for diagnostic purposes, a diagnostic reverse transcription-polymerase chain reaction (RT-PCR) was established. First, based on the obtained nucleotide sequence encoding for the capsid protein of the new chicken astrovirus oligonucleotides were delineated. The forward primer (CAP-DIAFP, 5'-GATAAG-GCTGGGCCGCAGAAGAAGAGG-3') (SEQ ID NO:18) and reverse primer (CAP-DIARP, 5'-ACAAATTTAACAA-CACACCGCTG-3') (SEQ ID NO:19) were located in the 5'-region of the capsid protein coding sequence. CAP-DIAFP is located from nucleotide 7-30, while the oligonucleotide sequence for primer CAP-DIARP is reverse-complementary to nucleotides 412-434 of the SEQ ID NO:2. Gut samples from either experimental or diagnostic cases were transferred into Lysing Matrix D tubes (MP Biomedicals, Solon, Ohio) containing 500 ul of sterile phosphate buffered saline (PBS). The samples were homogenized twice using the Fastprep®-24 (MP Biomedicals, Solon, Ohio) at a setting of 4.0 M/S for 20 seconds (s). Following one cycle of freeze/thaw at −80° C., the homogenized samples were centrifuged for 20 minutes (min) at 16000×g at 4° C. 200 ul of this supernatant were used for the purification of RNA using the RNeasy Plus Mini Kit (Qiagen Science, Maryland, USA). 5 ul of the obtained RNA was used in the RT-PCR using the primer pair CAP-DIAFP/CAP-DIARP and the SuperScript™ III One-Step RT-PCR System with Platinum® Taq (Invitrogen, Carlsbad, Calif., USA) following the instructions of the manufacturer. The reaction products were separated on a 1.5% agarose gel. For validation of the assay the obtained RT-PCR products were cloned and sequenced. To this end the RT-PCR fragment were gel eluted after separation on the agarose gel using the QIAquick Gel Extraction Kit (Qiagen) and cloned into the cloning plasmid pCR2.1 using the TOPO TA cloning kit (Invitrogen) following the instructions of the manufacturer. Plasmids containing an insert were sequenced using standard primer (M13, M13R) and the BigDye® Terminator v3.1 Cycle Sequencing Kit (Applied Biosystems, Foster City, Calif., USA). The sequences were analyzed using DNAstar software (DNAstar Inc, Madison, Wis., USA).

Results

Figure 15:
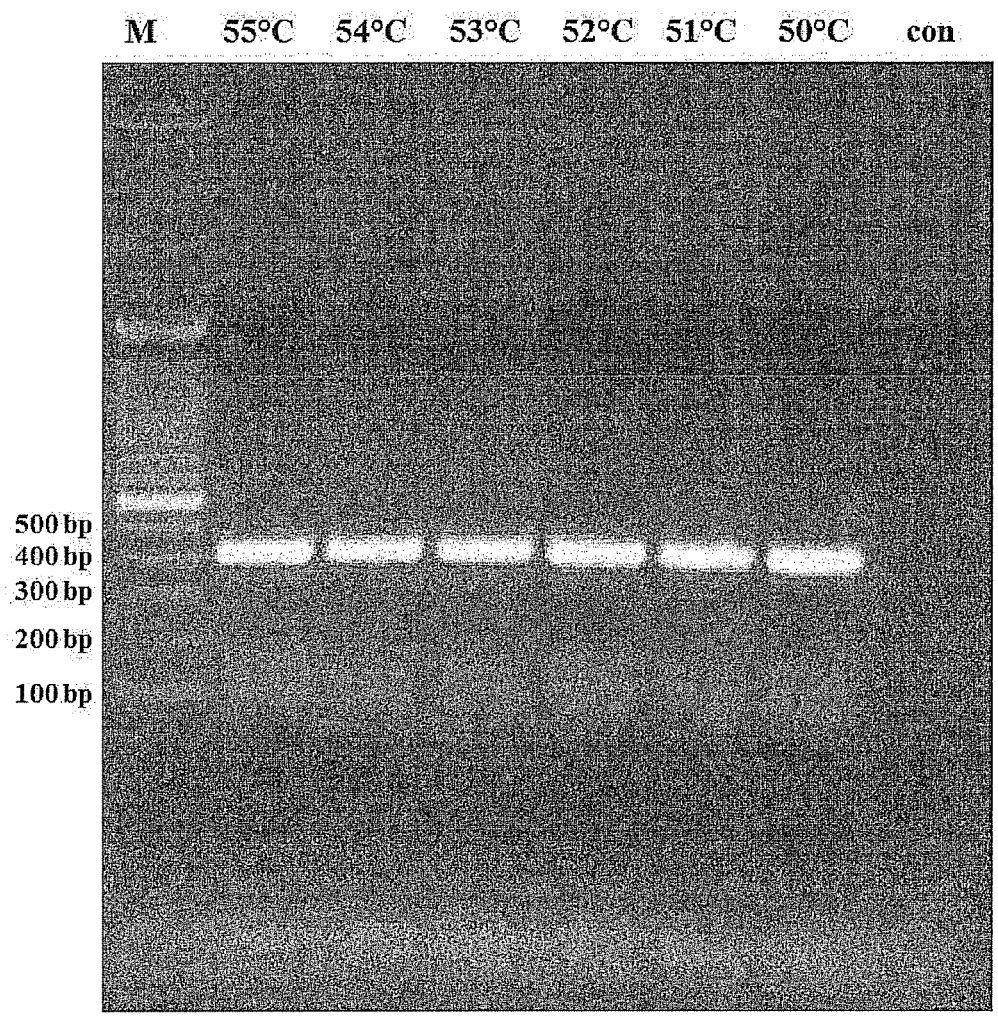
Figure 16:
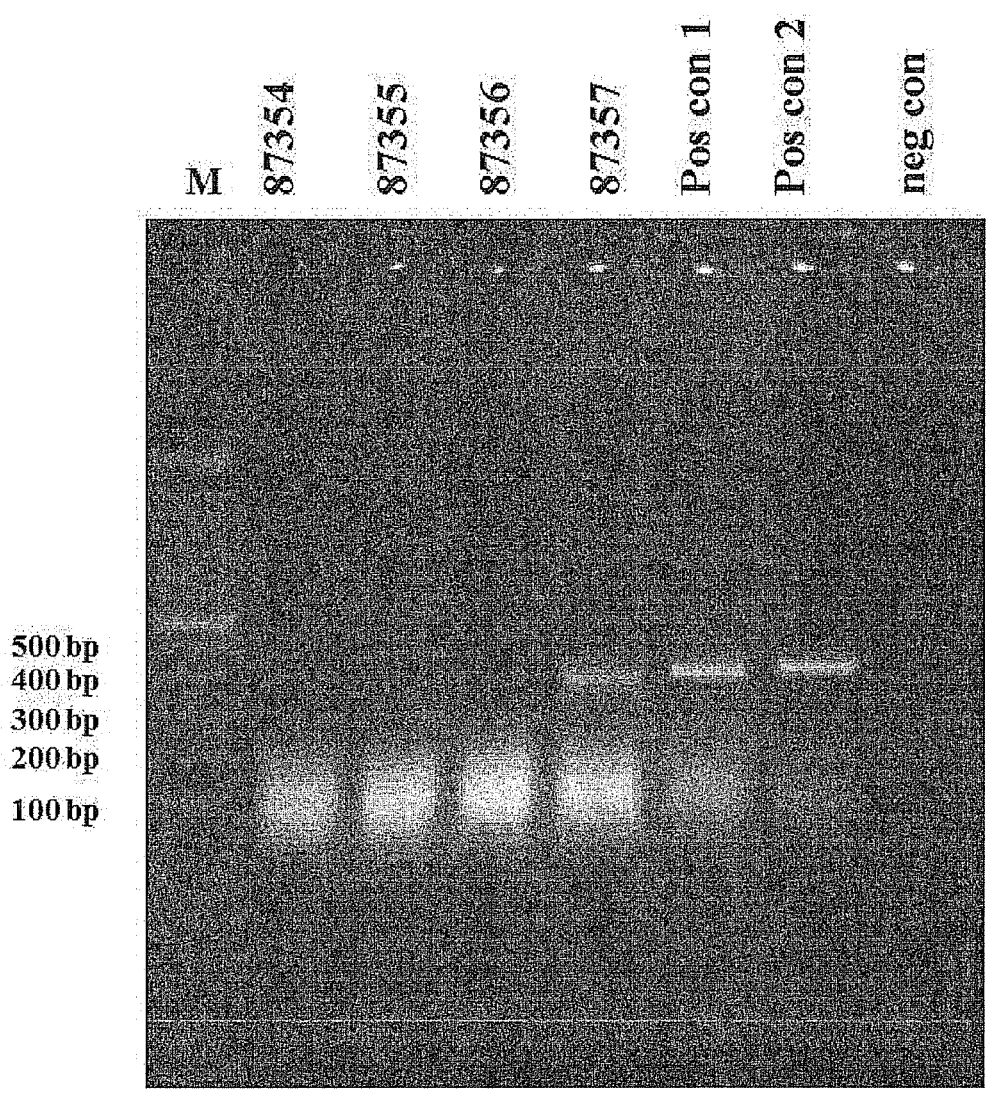
FIG. 16. Reverse transcription-polymerase chain reaction (RT-PCR) of diagnostic samples. RNA was purified from diagnostic gut samples (87354, 87355, 87356, and 87357), a gut sample from experiment 1 (pos control 1 and pos control 2). Positive control 2 was purified using a fully automated sample preparation machine (QIAcube, QIAgen, Hilden, Germany) using also the RNeasy Plus Mini Kit. RT-PCR was performed using astrovirus specific primer. The reactions products were separated on a 1.5% agarose gel. As negative control (neg con) a in parallel treated PBS sample was used. An 100 bp DNA ladder was used as marker (M).

Gut samples, obtained as described in Example 1, were used for the development of the RT-PCT assay. RNA from gut material of RSS-exposed chicken was purified, the RNA was extracted and used for RT-PCR using an temperature gradient for the annealing step for the PCR amplification ranging from 50° C. to 55° C. The expected size of the fragment was 428 base pairs and the length of the obtained showed the approximate length (FIG. 15). The negative control (here a PBS control) showed no PCR fragment indicating that during purification and subsequent handling no spill over of occurred. The signal after amplification of the RT-PCR fragment was not significant different between the different annealing temperatures, thus 52° C. was used for subsequent experiments. In order to confirm identify of the amplified RT-PCR fragment, the fragment was gel eluted and cloned into the pCR2.1 cloning vector. Three plasmids were sequenced and the consensus sequence was compared with the sequence of SEQ ID NO:2. The nucleotide sequence of the obtained fragment was 95% to the sequence of SEQ ID NO:2. In next experiments, gut samples from diagnostic submissions were used where the clinical signs were diarrhea of 14 day old broiler chickens from a complex in Alabama (FIG. 16). The diagnostic identifiers were 87354-87357. Each sample represented one chicken house of a broiler complex located in Alabama. The RT-PCR was performed as described above using the gut sample from Example 1 as positive control (pos con 1). The second positive control was an RNA preparation obtained by using the same purification kit in an automatic purification system (QIAcube, Qiagen, Hilden, Germany). The gel showed that in samples 87354 and 87355 a faint band was amplified. Sample 87356 remained negative, as well as the negative control. The RNA obtained from sample 87357 resulted in a strong signal comparable to both of the positive control samples. The obtained RT-PCR fragment was cloned into the cloning vector pCR2.1 and three plasmids were sequenced. The obtained consensus sequence showed a similarity of 90% to the sequence of SEQ ID NO:2 indicating a close relationship to the capsid protein encoding sequence.

Example 7

Establishment of a Polyclonal Serum and its Use for Diagnostics

Materials and Methods

Generation of a polyclonal serum from a rabbit specific for the new chicken astrovirus. For the generation of antiserum specific for the capsid protein of the new chicken astrovirus, a rabbit was repeatedly immunized at the Polyclonal Antibody Production Service facility (University of Georgia, Athens, Ga.) with the fraction containing the purified capsid protein of the new chicken astrovirus. This fraction was obtained using procedures as described in the previous examples. The resulting serum was named r-anti-CapCkAstv serum.

Cells. For the isolation of virus initially several cell lines were used: Cells of the chicken fibroblast cell line DF-1 (Himley et al, 1998), Madin-Darby canine kidney cells (MDCK cells, CRL-2285; ATCC, Manassas, Va.), a cell line derived from kidneys of African green monkeys (Vero cells, CRL-1587; ATCC), baby hamster kidney cell line 21 (BHK-21 cells, CCL-10, ATCC), and chicken primary hepatocellular carcinoma epithelial cells (LMH cells, CRL-2117, ATCC). All cells were grown in Dulbecco's modified Eagles's medium with 4.5 g/liter glucose (DMEM-4.5; Thermo Scientific, Waltham, Mass.) supplemented with 10% fetal bovine serum (FBS; Mediatech, Manassas, Va.). All cells except the LMH cells were cultivated in a humidified atmosphere at 37° C. with 5% CO2. The LMH cells were incubated in a humidified atmosphere at 39° C. with 5% CO2.

Cell culture passage. Gut material from either RSS affected chicken, as described in Example 1, or samples from diagnostic submissions were centrifuged at 3500×g for 20 min in a 50 ml centrifuge tube. The supernatant was taken and transferred to 2 ml reaction tubes and centrifuged again at 16000×g for 20 min. This supernatant was filtered first through a 0.45 micron filter (Whatman International Ltd, Florham Park, N.J., USA) followed by a filtration step through an 0.22 micron filter (Whatman International Ltd). 100 ul of the filtrate were incubated with 1 volume of chicken serum specific for chicken rotavirus and chicken reovirus (Charles River Laboratories International, Inc., Wilmington, Mass., USA) for one hour at 37° C. The mixture was added to cell cultures grown in 6-well-plates for one hour at the appropriate temperatures. Now the supernatant was removed and cell culture medium was added. The cell culture plates were incubated for until a cytopathic effect (CPE) was visible caused either by a possible virus or until the cells degenerated. The cells were freeze/thawed once and the supernatant was used for either a subsequent passage on cells or for infection of cells later used for indirect immunofluorescence.

Indirect immunofluorescence. LMH cells grown in 96 well cell culture plates were incubated with cell culture supernatants obtained from the passage on LMH cells for one hour at 39° C. In a next step the supernatant was removed and replaced with cell culture medium. The cells were incubated for three days (d), the supernatant removed and the cells were rinsed once with phosphate buffered saline (PBS). In the next step ice-cold 96% ethanol was added, incubated for 10 minutes (min) at room temperature (RT), and the ethanol was removed. The fixed cells were air dried and the r-anti-CapCk-Astv serum was added in a dilution in PBS of 1:100. The serum dilution was incubated for 30 minutes at RT, the cells washed three times with PBS, and the goat anti-rabbit FITC conjugate (Jackson Immunoresearch, West Grove, Pa., USA) diluted 1:200 in PBS was added. After an additional incubation for 30 min at RT the cells were rinsed again three times with PBS and finally overlaid with an antifading solution consisting of 2.5 g 1.4 Diazobicyclo (2.2.2.)-oktan (Sigma-Aldrich) solubilized in a solution containing 90% glycerol and 10% PBS. The fluorescence was documented using an inverted Zeiss microscope Axiovert 40 CFL (Zeiss GmbH, Jena, Germany).

Results

Rabbit serum can be used for identification of new chicken astrovirus. Experiments using the gut sample from Example 1 resulted in the isolation of a new chicken astrovirus. The indirect immunofluorescence using cell culture supernatant of passage resulted in a positive signal in LMH cells. All other cell lines (MDCK, BHK21, Vero, DF1) did not result in a positive immunofluorescence, even after five subsequent passages. This result indicates that LMH cells incubated at 39° C. can be used for the isolation of the new chicken astrovirus and that the r-anti-CapCkAstv serum can be used for the identification of a positive virus isolation.

In this example, gut samples from 39 diagnostic submissions were used for virus isolation as described in the material and method section. The inoculated LMH cells were incubated for 5 days, the cells were freeze/thawed and a second passage was performed which was also incubate for five days. After each passage LMH cells grown in 96 well plates were inoculated with 100 ul of the appropriate passage, incubated for three days and the cells were tested for the presence of virus by indirect immunofluorescence using the r-anti-CapCkAstv serum. Twenty nine cases resulted in a positive immunofluorescence either after passage 1 or 2. This indicated that the r-anti-CapCkAstv serum can be used for diagnostics for the identification of the presence of the new chicken astrovirus in submitted samples.

The complete disclosure of all patents, patent applications, and publications, and electronically available material (including, for instance, nucleotide sequence submissions in, e.g., GENBANK and RefSeq, and amino acid sequence submissions in, e.g., SwissProt, PIR, PRF, PDB, and translations from annotated coding regions in GENBANK and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. All headings are for the convenience of the reader and should not be used to limit the meaning of the text that follows the heading, unless so specified.

SEQUENCE LISTING FREE TEXT

SEQ ID NO:1 Nucleotide sequence of chicken astrovirus capsid (runting stunting) ORF.
SEQ ID NO:2 Deduced amino acid sequence of the runting stunting ORF.
SEQ ID NO:3-19 Synthetic oligonucleotide primers.

What is claimed is:

1. A polypeptide comprising an amino acid sequence with at least about 95% sequence identity to the amino acid sequence of SEQ ID NO:2, or a truncation thereof, wherein a truncation thereof comprises the removal of one, two, three, four, five, six, seven, eight, nine, or ten amino acids from the amino terminus of the polypeptide and/or the removal of one, two, three, four, five, six, seven, eight, nine, or ten amino acids from the carboxy terminus of the polypeptide.

2. The polypeptide of claim 1, the polypeptide comprising an amino acid sequence of SEQ ID NO:2, or a truncation thereof, wherein a truncation thereof comprises the removal of one, two, three, four, five, six, seven, eight, nine, or ten amino acids from the amino terminus of the polypeptide and/or the removal of one, two, three, four, five, six, seven, eight, nine, or ten amino acids from the carboxy terminus of the polypeptide.

3. An isolated polynucleotide sequence encoding a polypeptide of claim 1, wherein the isolated polynucleotide is a cDNA.

4. The isolated polynucleotide sequence of claim 3, the isolated polynucleotide sequence comprising SEQ ID NO:1.

5. A recombinant vector construct comprising a polynucleotide sequence encoding a polypeptide of claim 1 and a heterologous vector sequence.

6. An immunological composition for raising antibodies in poultry, the composition comprising the polypeptide of claim 1.

7. The composition of claim 6, further comprising an adjuvant.

8. The composition of claim 6, further comprising an antigenic determinant from one or more additional pathogens infectious to poultry.

9. A diagnostic kit comprising a polypeptide of claim 1.

10. A method of detecting exposure to runting-stunting syndrome (RSS) in a bird, the method comprising determining that an antisera sample obtained from the bird specifically binds to a polypeptide of claim 1.

11. A method of producing anti-RSS antibodies in poultry, the method comprising administering a polypeptide of claim 1.

12. An isolated astrovirus capsid polypeptide, the astrovirus capsid polypeptide comprising a polypeptide of claim 1.

13. A polypeptide comprising at least 75 consecutive amino acids of SEQ ID NO:2 or at least 75 consecutive amino acids of residues 1 to 743 of SEQ ID NO:2.

14. An immunological composition for raising antibodies in poultry, the composition comprising the polypeptide of claim 13.

15. The composition of claim 14, further comprising an antigenic determinant from one or more additional pathogens infectious to poultry.

16. A method of detecting a runting stunting syndrome (RSS) in a bird, the method comprising determining that an antisera sample obtained from the bird specifically binds to a polypeptide of claim 13.

17. A method of producing anti-RSS antibodies in poultry, the method comprising administering a polypeptide of claim 13.

18. An isolated polynucleotide sequence encoding a polypeptide of claim 13, wherein the isolated polynucleotide is a cDNA.

19. A diagnostic kit comprising a polypeptide of claim 13.

20. An isolated astrovirus capsid polypeptide, the astrovirus capsid polypeptide comprising an amino acid sequence with at least about 95% sequence identity to the amino acid sequence of SEQ ID NO:2.

* * * * *